United States Patent [19]
Nemeth et al.

[11] Patent Number: 6,001,884
[45] Date of Patent: Dec. 14, 1999

[54] CALCIUM RECEPTOR-ACTIVE MOLECULES

[75] Inventors: Edward F. Nemeth; Bradford C. Van Wagenen, both of Salt Lake City; Manuel F. Balandrin, Sandy; Eric G. Delmar; Scott T. Moe, both of Salt Lake City, all of Utah

[73] Assignee: NPS Pharmaceuticals, Inc., Salt Lake City, Utah

[21] Appl. No.: 08/469,204

[22] Filed: Jun. 6, 1995

Related U.S. Application Data

[63] Continuation-in-part of application No. 08/353,784, Dec. 8, 1994, which is a continuation-in-part of application No. PCT/US94/12177, Oct. 21, 1994, and a continuation-in-part of application No. 08/292,827, Aug. 19, 1994, abandoned, and a continuation-in-part of application No. 08/141,248, Oct. 22, 1993, abandoned, and a continuation-in-part of application No. 08/009,389, Feb. 23, 1993, abandoned, which is a continuation-in-part of application No. 08/017,127, Feb. 12, 1993, abandoned, which is a continuation-in-part of application No. 07/934,161, Aug. 21, 1992, abandoned, which is a continuation-in-part of application No. 07/834,044, Feb. 11, 1992, abandoned, which is a continuation-in-part of application No. 07/749,451, Aug. 23, 1991, abandoned.

[51] Int. Cl.$^6$ ..................................................... A01N 35/00
[52] U.S. Cl. .......................... 514/699; 564/387; 564/389; 564/390; 564/392; 564/655
[58] Field of Search ..................................... 564/387, 389, 564/390, 392, 164; 514/655, 319, 415, 418, 466, 524, 546, 620; 546/305, 306; 548/484, 491; 549/443; 558/422; 560/138

[56] References Cited

U.S. PATENT DOCUMENTS

| | | |
|---|---|---|
| 2,276,618 | 3/1942 | Kulz et al. . |
| 2,930,731 | 3/1960 | Heinzelmann et al. ................. 514/555 |
| 2,949,359 | 8/1960 | Blout et al. .............................. 430/441 |
| 3,202,711 | 8/1965 | Fruhstorfer et al. . |
| 3,262,977 | 7/1966 | Harsanyi et al. . |
| 3,493,662 | 2/1970 | Duerr et al. ............................. 514/654 |
| 3,536,712 | 10/1970 | Keck et al. . |
| 3,689,524 | 9/1972 | Jack et al. . |
| 3,842,067 | 10/1974 | Sarantakis . |
| 4,000,197 | 12/1976 | Barfknecht et al. . |
| 4,014,937 | 3/1977 | Richardson . |
| 4,098,890 | 7/1978 | Molloy . |
| 4,242,355 | 12/1980 | Nedelec et al. . |
| 4,289,787 | 9/1981 | Molloy et al. . |
| 4,360,511 | 11/1982 | Baldwin et al. . |
| 4,391,826 | 7/1983 | Mills et al. . |
| 4,487,965 | 12/1984 | Himmele et al. . |
| 4,587,253 | 5/1986 | Halczenko et al. . |
| 4,591,605 | 5/1986 | Ray . |
| 4,608,391 | 8/1986 | Ginos et al. . |
| 4,609,494 | 9/1986 | Baldwin . |
| 4,647,446 | 3/1987 | Sargent et al. . |
| 4,661,635 | 4/1987 | Carson . |
| 4,675,321 | 6/1987 | Baldwin . |
| 4,677,101 | 6/1987 | Claremon et al. . |
| 4,728,660 | 3/1988 | Haynes et al. . |
| 4,769,483 | 9/1988 | Lombardi et al. . |
| 4,797,411 | 1/1989 | Crugnola et al. . |
| 4,808,718 | 2/1989 | Hartman et al. . |
| 4,839,369 | 6/1989 | Youssefyeh et al. . |
| 4,916,145 | 4/1990 | Tilley et al. . |
| 4,925,664 | 5/1990 | Jackson et al. . |
| 4,925,873 | 5/1990 | Freidhoff . |
| 4,967,003 | 10/1990 | Rentzea et al. . |
| 4,987,071 | 1/1991 | Cech et al. . |
| 4,988,730 | 1/1991 | Korbonits et al. . |
| 4,992,378 | 2/1991 | Kelly et al. . |
| 5,001,251 | 3/1991 | MacManus et al. . |
| 5,011,834 | 4/1991 | Weber et al. . |
| 5,021,599 | 6/1991 | Beer et al. . |
| 5,030,576 | 7/1991 | Dull et al. . |
| 5,034,514 | 7/1991 | Nitecki et al. . |
| 5,045,466 | 9/1991 | Morrison . |
| 5,053,337 | 10/1991 | Weinshank et al. . |
| 5,064,657 | 11/1991 | Jackson et al. . |
| 5,073,648 | 12/1991 | Hagishita et al. ....................... 564/374 |
| 5,075,338 | 12/1991 | Knoll et al. ............................. 514/654 |
| 5,082,837 | 1/1992 | Palfreyman et al. . |
| 5,298,660 | 3/1994 | Yoneyoshi et al. ..................... 564/302 |
| 5,334,628 | 8/1994 | Maeda et al. . |

(List continued on next page.)

FOREIGN PATENT DOCUMENTS

| | | |
|---|---|---|
| 621300 | 3/1962 | Belgium . |
| 1065857 | 4/1991 | China . |
| 217009 | 7/1984 | Czech Rep. . |
| 0005848 | 12/1979 | European Pat. Off. . |
| 0007204 | 1/1980 | European Pat. Off. . |
| 0009702 | 4/1980 | European Pat. Off. . |
| 0015505 | 9/1980 | European Pat. Off. . |
| 0408284 | 1/1981 | European Pat. Off. . |
| 0023385 | 2/1981 | European Pat. Off. . |
| 044 158 A1 | 1/1982 | European Pat. Off. . |

(List continued on next page.)

OTHER PUBLICATIONS

Takenaka, et al., J. Chem. Soc. Perkin Trans 2:EN; 95–99 (1978), "Induced Circular Dichroism of Chiral Amine–Benzoylbenzoic Acid Systems".

Lavanchy, Archives Des Sciences (Geneva), 11, 252–255 (1958).

Walker, et al., J. Med. Chem., 9(4), 624–30 (1966), "Synthesis of Varied Heterocyclic and Substituted Aryl Alkyl Secondary Amiones, relaed Schiff Bases, and Amides".

Giovambattista, et al., Ciencia e invest. (Buenos Aires) 14, 34–5 (1968), "Investigaciones Recientes".

(List continued on next page.)

*Primary Examiner*—Richard L. Raymond
*Attorney, Agent, or Firm*—Lyon & Lyon LLP

[57] ABSTRACT

The present invention features molecules which can modulate one or activities of an inorganic ion receptor. Preferably, the molecule can mimic or block the effect of extracellular $Ca^{2+}$ on a calcium receptor. The preferred use of such molecules is to treat diseases or disorders by altering inorganic ion receptor activity, preferably calcium receptor activity.

44 Claims, 90 Drawing Sheets

U.S. PATENT DOCUMENTS

| | | | |
|---|---|---|---|
| 5,403,861 | 4/1995 | Goldin et al. | 514/634 |
| 5,504,253 | 4/1996 | Van Wagenen et al. | 564/374 |
| 5,510,519 | 4/1996 | Yoneyoshi et al. | 562/401 |
| 5,633,404 | 5/1997 | Van Wagenen et al. | 564/182 |

FOREIGN PATENT DOCUMENTS

| | | |
|---|---|---|
| 0092787 | 11/1983 | European Pat. Off. . |
| 0101069 | 2/1984 | European Pat. Off. . |
| 0200101 | 12/1986 | European Pat. Off. . |
| 0253327 | 1/1988 | European Pat. Off. . |
| 0270376 | 6/1988 | European Pat. Off. . |
| 0289287 | 11/1988 | European Pat. Off. . |
| 0309100 | 3/1989 | European Pat. Off. . |
| 0384740 | 8/1990 | European Pat. Off. . |
| 0395357 | 10/1990 | European Pat. Off. . |
| 0455510 | 5/1991 | European Pat. Off. . |
| 0443606 | 8/1991 | European Pat. Off. . |
| 0224163 | 10/1991 | European Pat. Off. . |
| 0508307 | 10/1992 | European Pat. Off. . |
| 1231690 | 12/1967 | Germany . |
| 2541184 | 4/1976 | Germany . |
| 2825961 | 1/1980 | Germany . |
| 53-90272 | 8/1978 | Japan . |
| 59-50358 | 3/1984 | Japan . |
| 2200658 | 8/1990 | Japan . |
| 1079091 | 8/1967 | United Kingdom . |
| 1109924 | 4/1968 | United Kingdom . |
| 1448437 | 2/1974 | United Kingdom . |
| 1464209 | 2/1977 | United Kingdom . |
| 2113089 | 8/1983 | United Kingdom . |
| 2213818 | 8/1989 | United Kingdom . |
| 8204052 | 11/1982 | WIPO . |
| 8906135 | 7/1989 | WIPO . |
| 8909834 | 10/1989 | WIPO . |
| 9100853 | 1/1991 | WIPO . |
| 9109594 | 7/1991 | WIPO . |
| 9113077 | 9/1991 | WIPO . |
| 9207829 | 5/1992 | WIPO . |
| 9214709 | 9/1992 | WIPO . |
| 9304373 | 3/1993 | WIPO . |
| 9310073 | 5/1993 | WIPO . |
| 9313052 | 7/1993 | WIPO . |
| 9315044 | 8/1993 | WIPO . |
| 9418959 | 9/1994 | WIPO . |
| 9511221 | 4/1995 | WIPO . |
| 9518134 | 7/1995 | WIPO . |
| 9521815 | 8/1995 | WIPO . |

OTHER PUBLICATIONS

West. et al., J. Am. Pharm. Assoc. 46. 58–61 (1957). "A pharmacological Study of a Series of Aralkylamines".

Majewski et al., "1,3–Dioxan–50 ones: synthesis, deprotonation, and reactions of their lithium enolates," *Can. J. Chem.* 73:1616–1625 (1995).

Majewski et al., "Synthesis of Butenolides via Enantioselective Deprotonation of Protected 4–Hydroxycyclohexanone," *Tetrahedron Asymmetry* 6:1837–1840 (1995).

Merck Index, 11th Edition, Monograph No. 2993, p. 475 (1989).

Polniaszek and Kaufman, "Steroselective Nucleophilic Additions to the Carbon–Nitrogen Double Bond. 2. Chiral Iminium Ions Derived from "Second Generation" Chiral Amines," *J. Am. Chem. Soc.* 111:4859–4863 (1989).

Abe et al., "Molecular Characterization of a Novel Metabotropic Glutamate Receptor mGluR5 Coupled to Inositol Phosphate/$Ca^{2+}$ Signal Transduction," *J. Biol. Chem.*, 267:13361–13368 (1992).

Barney et al., "A Convenient Synthesis of Hindered Amines and α–Trifluoromethylamines from Ketones," *Tetrahedron Letters*, 31:5547–5550 (1990).

Batra and Alenfall, "Effects of Diverse Categories of Drugs on Human Colon Tumour Cell Proliferation," *Anticancer Research* 11:1221–1224 (1991).

Becalski et al., "Catalytic asymmetric hydorgenation of imines. Use of rhodium(l)/phosphine comploexes and characterization of rhodium(l)/imine complexes," *Chemical Abstracts*, 116:558 at Abstract No. 14742U (1992).

Bertz et al., "Asymmetric Induction with Amidocuprates," *J. Org. Chem.* 51:4953–4959 (1986).

Bringmann et al., "Enantiomerically Pure–N–boc Protected β–Keto–γ–Amino Acid Esters from Simple Keto Precursors: A Novel, Stereocontrolled Approach to Statine Derivatives with Any Desired Configuration," *Synlett* pp. 253–255 (May 1990).

Bringmann et al., "The Enantioselective Synthesis of Optically Active, Benzene Nucleus–Substituted 1–Phenylethylamines from the Corresponding Acetophenones," *Liebigs Ann. Chem.* pp. 795–805 (1990).

Brown, "Extracellular $Ca^{2+}$ Sensing, Regulation of Parathyroid Cell Function and Role of $Ca^{2+}$ and Other Ions as Extracellular (First) Messengers," *Physiological Reviews* 71:371–411 (1991).

Brown et al, "Cloning and characterization of an extracellular $Ca^{2+}$ sensing receptor from bovine parathryoid," *Nature* 366:575–580 (1993).

Brown et al., "A Comparison of the Effects of Divalent and Trivalent Cations on Parathyroid Hormone Release, 3',5'–Cyclic–Adenosine Monophosphate Accumulation, and the Levels of Inositol Phosphates in Bovine Parathyroid Cells," *Endocrinology* 127:1064–1071 (1990).

Brown et al., "High Extracellular $Ca^{2+}$ and $Mg^{2+}$ Stimulate Accumulation of Inositol Phosphates in Bovine Parathyroid Cells," *FEBS Letters* 218:113–118 (1987).

Brown et al., "Neomycin Mimics the Effects of High Extracellular Calcium Concentrations on Parathyroid Function in Dispersed Bovine Parathyroid Cells," *Endocrinology*, 128:3047–3054 (1991).

Brown et al., "Polyarginine, Polylysine, and Protamine Mimic the Effects of High Extracellular Calcium Concentrations on Dispersed Bovine Parathyroid Cells," *J. Bone and Mineral Res.*, 6:1217–1225 (1991).

Capuano et al., "Characterization of the Human Calcium Receptor Gene," *J. Bone and Mineral Research* 9(1):S145 at 98 (1994).

*Chemical Abstracts Formula Index*, vol. 110 p. 537F (1989).

*Chemical Abstracts Formula Index*, vol. 110 p. 1793F (1989).

Chen et al., "Injection of Bovine Parathyroid Poly(A)$^+$ RNA into Xenopus Oocytes Confers Sensitivity to High Extracellular Calcium," *J. Bone Min. Res.* 9:293–300 (1994).

Chen and Brown, "The Diltiazem Analog TA–3090 Mimics the Actions of High Extracellular $Ca^{2+}$ on Parathyroid Function in Dispersed Bovine Parathyroid Cells," *J. Bone and Mineral Res.*, 5:581–587 (1990).

Clifton et al., "Arylethanolamines derived from salicylamide with alpha– and beta–adrenoceptor blocking activities. Preparation of labetalol, its enantiomers and related salicylamides," *J. Med. Chem.* 25:670–679 (1982).

Danks, "Reaction of Hydride Transfer Reducing Agents with (1–heterodiene) tricarbonyliron(0) Complexes and the Synthesis of Saturated Amines and Alcohols," *Tetrahedron Lett.* 35:4177–4178 (1994).

Davies and Ichihara, "Asymmetric Synthesis of R–β–Amino Butanoic Acid and S–β–Tyrosine: Homochiral Lithium Amide Equivalents for Michael Additions to α,β–Unsaturated Esters," *Tetrahedron: Asymmetry* 2:183–186 (1991).

Dottavio–Martin and Ravel, "Radiolabeling of Proteins by Reductive Alkylation with [$^{14}$C]Formaldehyde and Sodium Cyanoborohydride," *Analytical Biochem.*, 87:562–565 (1978).

Duelfer et al., "Synthesis of 14C–dilevalol," *J. Labelled Compd. Radiopharm* 25:855–863 (1988).

Fox et al., "A First Generation Calcimimetic Compound (NPS R–568) That Acts on the Parathyroid Cell Calcium Receptor: A Novel Therapeutic Approach for Hyperparathyroidism," *J. Bone and Mineral Research* 8(1):S181 at 260 (1993).

Fox et al., "NPS R–568 Inhibits Parathyroid Hormone Secretion and Stimulates Calcitonin Secretion in Hyperparathyroid Rats with Chronic Renal Failure," *J. American Society of Nephrology* 4:719 at 69P (1993).

Fox et al., "NPS R–568 Acts on Calcium Receptors to Inhibit Parathyroid Hormone and Stimulate Calcitonin Secretion: A Novel Therapeutic Approach for Hyperparathyroidisum," *J. American Society of Nephrology* 4:719 at 120P (1993).

Fox et al., "Parathyroid Gland Calcium Receptor Gene Expression is Unaffected by Chronic Renal Failure or Low Dietary Calcium in Rats," *J. Am. Soc. Nephrology* 5:879 at 90P (1994).

Fox et al., "Physiologically Relevant PTH Levels are Anabolic on Bone in Ovariectomized Rats," *Bone* 16:194S at 434 (1995).

Fox et al., "Prevention of Hypocalcemia Prolongs the Plasma Parathyroid Hormone and Calcitonin Responses to the Calcimimetic Compound NPS R–568 in Rats," *J. Bone Min. Res.* 9(1):S409 at C396 (1994).

Fuji et al., "Endothelin as an Autocrine Factor in the Regulation of Parathyroid Cells," *Proc. Natl. Acad. Sci. USA* 88:4235–4239 (1991).

Fuleihan et al., "Effects of the Lectin Concanavalin–A on the Regulation of Second Messengers and Parathyroid Hormone Release by Extracellular $Ca^{2+}$ in Bovine Parathyroid Cells," *Endocrinology* 128:2931–2936 (1991).

Fuleihan and Brown, "Effect on the Lectin Concanavalin–A on Calcium–Regulated Adenosine 3', 5'–Monophosphate Accumulation in Bovine Parathyroid Cells," *Endocrinology* 126:1996–2002 (1990).

Garrett et al., "Cloning and Expression of a G–Protein––Coupled Calcium Receptor From a Human Parathyroid Adenoma," *J. Bone and Mineral Research* 8(1):S148 at 125 (1993).

Garrett et al., "Expression of the Parathyroid Calcium Receptor Gene in C–Cells," *J. Bone Min. Res.* 9(1):S409 at C398 (1994).

Hammerland et al., "Mechanism of Action of the Calcimimetic Compounds NPS R–467 and NPS R–568 in Xenopus Oocytes Expressing a Bovine Parathyroid Cell Calcium Receptor," *J. Bone and Mineral Research* 8(1):S133 at 65 (1993).

Hawkins et al., "The Effects of High Extracellular $Ca^{2+}$ and $Mg^{2+}$ Concentrations on the Levels of Inositol 1,3,4,5–Tetrakisphosphate in Bovine Parathyroid Cells," *Endocrinology* 124:838–844 (1989).

Harootunian et al., "Effects of Calcitonin and Extracellular Calcium on Cytosolic Levels of Cyclic AMP and $Ca^{2+}$ in Rabbit Osteoclasts," *J. Bone and Mineral Research* 9(1):S246 at B66 (1994).

Heath et al., "Inhibition of Human Parathyroid Hormone Secretion In Vivo by NPS R–568, a Calcimimetic Drug that Targets the Parathyroid Cell–Surface Calcium Receptor," *Bone* 16:85S at 23 (1995).

Holtje et al., "Conformational Analysis on Calcium Channel Active Diphenylalkylamines, Diphenylbutylpiperidines, Phenylalkylamines, and Perhexiline," *Quantitative Structure: Activity Relationships* 8:259–265 (1989).

Hung et al., "Coupling of the Porcine Calcitonin Receptor to Cytosolic $Ca^{2+}$ and cAMP Levels in Xenopus Oocytes," *J. Bone and Mineral Research* 9(1):S410 at C400 (1994).

Jasys et al., "The Total Synthesis of Argiotoxins 636, 659 and 673," *Tetrahedron Letters*, 29:6223–6226 (1988).

Juaristi et al., "Use of N,N$^1$–Dimethylpropyleneura (DMPU) as Solvent in the Efficient Preparation of Enantiomerically Pure Secondary Amines," *Synthesis* pp. 1243–1246 (Dec. 1993).

Katz et al., "Structure–Function Relationships for the Effects of Various Aminoglycoside Antibotics on Dispersed Bovine Parathyroid Cells," *Endocrinology* 131:903–910 (1992).

Kifor et al., "Phorbol Esters Modulate the High $Ca^{2+}$–Stimulated Accumulation of Inositol Phosphates in Bovine Pharathyroid Cells," *Journal of Bone and Mineral Research* 5:1003–1011 (1990).

Kifor and Brown, "Relationship between Diacylglycerol Levels and Extracellular $Ca^{2+}$ in Dispersed Bovine Parathyroid Cells," *Endocrinology* 123:2723–2729 (1988).

Kim et al., "Studies on the Structural Requirements for the Activity of the Skeletal Muscle Dihydropyridine Receptor/ Slow $Ca^{2+}$ Channel," *J. Biol. Chem.* 265:11858–11863 (1990).

Koenig et al., "Polyamines Mediate Androgenic Stimulation of Clacum Fluxes and Membrane Transport in Rat Heart Myocytes," *Circulation Research* 64:415–426 (1989).

Komeyoshi and Kudo, "Optically active amines and their manufacture, intermediates and uses," *Chemical Abstracts* 121:1060 at Abstract No. 230462Y (1994).

Larsson et al., "Paradoxical effects of K$^+$ and D–600 on parathyroid hormone secretion and cytoplasmic $Ca^{2+}$ in normal bovine and pathological human parathyroid cells," *Biochem. Biophys. Acta* 847:263–269 (1985).

Lensink and De Vries, "Disastereoselective hydrogenation and kinetic resolution of imines using rhodium/diphosphine catalyzed hydrogenation," *Tetrahedron: Asymmetry* 4:215–222 (1993).

Lensink and de Vries, "Improving Enantioselectivity by Using a Mono–Sulphonated Diphosphine as Ligand for Homogeneous Imine Hydrogenation," *Tetrahedron:Asymmetry* 3:235–238 (1992).

Leszkovszky et al., "The Pharmacology of Diphenylalkyl Derivatives," *Acta Physiologica Academiae Scientiarum Hungaricae Tomus* 29:283–297 (1966).

Levine, *Pharmacology: Drug Actions and Reactions*, Little Brown and Company, Inc. pp. 192–196 (1990).

Lopez–Barneo and Armstrong, "Depolarizing Response of Rat Parathyroid Cells to Divalent Cations," *J. Gen. Physiol.* 82:269–294 (1983).

Mattson et al., "An Improved Method for Reductive Alkylation of Amines Using Titanium(IV) Isopropoxide and Sodium Cyanoborohydride," *J. Org. Chem.*, 55:2552–2554 (1990).

Mikami et al., "Primary Structure and functional expression of the cardiac dihydropyridine–sensitive calcium channel," *Nature* 340:230–233 (1989).

Mithal et al., "Highly Purified Sheep C–Cells Express an Extraceculluar $Ca^{2+}$ Receptor Similar to that Present in Parathyroid," *J. Bone Min. Res.* 9(1):S282 at B209 (1994).

Muff et al., "Regulation of Hormone Secretion and Cytosolic $Ca^{2+}$ by Extracellular $Ca^{2+}$ in Parathyroid Cells and C–Cell: Role of Voltage–Senstive $Ca^{2+}$ Channels," *Archives of Biochemistry and Biophysics* 265:128–135 (1988).

Nemeth, E., "$Ca^{2+}$ Receptor–Dependent Regulation of Cellular Functions," *News in Physiological Sciences* 10:1–15 (1995).

Nemeth et al., "Screening of compounds with potential action against calcium receptors and their use in therapy of disorders of calcium metabolism," *Chemical Abstracts* 122(1):P1057y (1995).

Nemeth, "Evidence for the Presence of a Novel $Ca^{2+}$–Binding Protein ($Ca^{2+}$ Receptor) on the Surface of Parathyroid Cells," *Calcium–Binding Proteins in Health and Disease*, eds. A.W. Norman, T.C. Vanaman, A.R. Means (San Diego:Academic Press, Inc. 1987) pp. 36–38.

Nemeth, "Regulation of cytosolic calcium by extracellular divalent actions in C–cells and parathyroid cells," *Cell Calcium* 11:323–327 (1990).

Nemeth and Carafoli, "The role of extracellular calcium in the regulation of intracellular calcium and cell function," *Cell Calcium* 11:319–321 (1990).

Nemeth and Scarpa, "Cytosolic $Ca^{2+}$ and the Regulation of Secretion in Parathyroid Cells," *FEBS Letters* 203:15–19 (1986).

Nemeth and Scarpa, "Rapid Mobilization of Cellular $Ca^{2+}$ in Bovine Parathyroid Cells Evoked by Extracellular Divalent Cations–Evidence for a Cell Surface Calcium Receptor," *J. Biol. Chem.* 262(11):5188–5196 (1987).

Nemeth and Scarpa, "Receptor–Dependent Mobilization of Cellular $Ca^{2+}$ and the Regulation of Hormone Secretion in Parathyroid Cells," *Calcium Regulation and Bone Metabolism: Basic and Clinical* 9:167–171 (1987).

Nemeth and Scarpa, "Spermine Evokes the Rapid Mobilization of Cellular $Ca^{2+}$ in Parathyroid Cells," *Calcium–Binding Proteins in Health and Disease*, eds. A.W. Norman, T.C. Vanaman, A.R. Means (San Diego:Academic Press, Inc. 1987) pp. 33–35.

Opie, "Calcium Channel Antagonists Part V: Second–Generation Agents," *Cardiovascular Drugs and Therapy* 2:191–203 (1988).

Racke, "Functional Expression of the Parathyroid Cell Calcium Receptor in Xenopus oocytes," *FEBS Lett.* 333:132–136 (1993).

Racke et al., "Functional Expression of the Parathyroid Cell Calcium Receptor in Xenopus Oocytes," *J. of Bone and Mineral Res.*, Supplement 1, 6(S1):S118 (1991).

Rogers et al., "Calcium Receptor Expression in the Parathryoid Glands of Vitamin D–Deficient Rats is not Regulated by Plasma Caclium and 1,25(OH)$_2$D$_3$," *J. Bone and Mineral Research* 9(1):S409 at C392 (1994).

Rogers et al., "Localization of Calcium Receptor mRNA in Rat Thyroid and Parathyroid Glands Using In Situ Hybridization Histochemistry," *J. Bone and Mineral Research* 9(1):S409 at C390 (1994).

Rogers et al., "The Calcimimetic Compound NPS467 Reduces Plasma Calcium in a Dose–Dependent and Stero–Specific Manner," *J. Bone and Mineral Research* 8(1):S180 at 254 (1993).

Seely et al., "The Calcium Channel Blocker Diltizaem Lowers Serum Parathyroid Hormone Levels in vivo and in vitro," *Journal of clinical Endocrinology and Metabolism*, 68:1007–1012 (1989).

Shoback and Chen, *J. Bone Mineral Res.* 9:293 (1994).

Shoback and Chen, "Injection of Poly (A)$^+$ RNA from Bovine Parathyroid Tissue into Xenopus Oocytes Confers Sensitivity to Extracellular Calcium," *J. of Bone and Mineral Res.*, Supplement 1, 6(S1):S135 (1991).

Steffey and Nemeth, "Extracellular Calcium–Sensing Mechanisms on Osteoclasts and Parathyroid Cells are Pharmacologically Distinct," *J. Bone and Mineral Research* 8(1):S384 at 1071 (1993).

Steffey et al., "Calcimimetics: Structually and Mechanistically Novel Compounds that Inhibit Hormone Secretion From Parathyroid Cells," *J. Bone and Mineral Research* 8(1):S175 at 236 (1993).

Triggle et al., "$Ca^{2+}$ Channel Ligands: Structure–Function Relationships of the 1,4–Dihydropyridines," *Medicinal Research Review*, vol. 9, No. 1, pp. 123–180 (1989).

Van Niel and Pandit, "NADH Models XXI. Steroselective Reduction of Chiral Imines with Hantzsch Ester," *Tetrahedron* 41:6065–6011 (1985).

Zaidi, "Calcium Receptors' on Eukaryotic Cells with Special Reference to the Osteoclast," *Bioscience Reports* 10:493–507 (1990).

Zaidi, "Intracellular calcium in the control of osteoclast function. II. Paradoxical elevation of cytosolic free calcium by verapamil," *Biochem. and Biophys. Res. Communications*, 167:807–812 (1990).

Hashimoto et al., "Highly Diastereoselective Addition of Organometallic Reagents to Chiral Almines Derived from 1–(2–Methoxyphenyl) ethylamine," *Synlett* 9:961–962 (1995).

Majewski and MacKinnon, "Enantioselective deprotonation of protected 4–hydroxycyclohexanones," *Can. J. Chem.* 72(7):1699–1704 (1994).

Wang and Backvall, "Ruthenium–catalysed Transfer Hydrogenation of Imines by Propan–2–ol," *J. Chem. Soc., Chem. Commun.* pp. 980–982 (1992).

Anderson and Santi, "Phenylalanyl Transfer Ribonucleic Acid Synthetase from *Escherichia coli* B. Potent Inhibition by Analogues of N–Benzyl–2–phenylethylamine," *J. Med. Chem.* 19:1270–1275 (1976).

Boyd et al., "Dynamic Sterochemistry of Imines and Derivatives. Part 18. Photosynthesis and Photoracemization of Optically Active Oxaziridines," *J. Chem. Soc. Perkin Trans. I* 4:849–855 (1985).

Fraser et al., "Substitution α to the Nitrogen in Dibenzylamine via Carbanion Intermediates," *Can. J. Chem.* 51:1109–1115 (1973).

Gracheva et al., "Stereodirection of Ketimine Reduction Reactions," *Zhural Organicheskoi Khimii* 9(6):1235–1239 (1973).

Gracheva et al., "The Steroselectivity of the Reactions of Schiff Bases with Organomagnesium Compounds," *Zhural Organicheskoi Khimii* 10(3):557–561 (1974).

Hu et al., "Lithium hydride elimination in the reactions of organolithium compounds with imines: synthesis of secondary amines with branched groups," *C.R. Acad. Sci. Paris Ser. C* 284(4):195–198 (1977).

Hutton et al., "Organic Reagents for the Precipitation of Nitrate Ion. Part I. N–Substituted 1–naphthylmethylamines," *J. Chem. Soc.* (A) 11:1573–1579 (1966).

Joshi and Mehrotra, "Reductive Coupling In Substituted Imines with Aluminium–Amalgam in Moist Ether," *Nat. Acad. Sci. Letters (India)* 3:268–272 (1980).

Ikegami and Yamada, "Chemistry of Sodium Borohydride and Diborane. II. Reduction of Schiff Bases with Diborane in Tetrahydrofuran," *Chem. Pharm. Bull.* 14(12):1389–1399 (1966).

Katritzky et al., "Convenient Preparations of Imines and Symmetrical Secondary Amines Possessing Primary or Secondary Alkyl Groups," *Synthesis* 9:703–708 (1991).

Langlois et al., "Asymmetric synthesis of amines by hydrosilylation of imines catalyzed by a chiral complex of rhodium," *Tetrahedron Lett.* 49:4865–4868 (1973).

Neuvonen and Pihlaja, "Studies on the Benoxazine Series. Part 3—Preparation and $^{13}$C NMR Structural Study of γ Effects of Some N–Substituted 3,4–Dihydro–2H–1,3–benzoxazines," *Magnetic Resonance in Chemistry* 28:239–245 (1990).

Polniaszek and Dillard, "Diastereoselective Addition of Organometallic Reagents to Chiral Immune Ions: Synthesis of (S)–(+)–Cryptostyline I," *Tetrahedron Lett.* 31:797–800 (1990).

Paulsen–Sorman et al., "Cytochrome P–455 nm Complex Formation in the Metabolism of Phenylalkylamines. 8. Stereoselectivity in Metabolic Intermediary Complex Formation with a Series of Chiral 2–Substituted 1–Phenyl–2–aminoethanes," *J. Med. Chem.* 27:342–346 (1984).

Rai and Singh, "Synthesis and reduction of ketimines," *Indian J. Chem. Sect. B* 14B:377–378 (1976).

Schwartz and Hu, "Synthesis of Hindered Secondary Amines via Grignard Reagent Addition to Ketonitrones," *Tetrahedron Lett.* 13:1689–1692 (1992).

Van Dijk and Moed, "Synthesis of β–Phenylethyloamine Derivatives X$^{1*}$ N–(Hydroxy– and Methoxy–Aralkyl) Derivatives," *Recl. Trav. Chim. Pays–Bas* 92:1281–1297 (1973).

Yamaguchi et al., "Asymmetric Reduction with Chiral Reagents from Lithium Aluminum Hydride and (S)–(–)–N–(o–Substituted benzyl)–α–phenylethylamines," *J. Org. Chem.* 42:1578–1581 (1977).

Arjona et al., "Sterochemistry of the reduction of the imino group. IV. Sterochemsitry of the reduction of N–(1–phenylethyl)–1–alkyl–1–arylmethanimines," *An. Quim. Ser. C* 81(1):23–29 (1985).

Freifelder, "Selective Hydrogenolysis. Dehalogenation in the Presence of N–Benzyl Linkage," *J. Org. Chem.* 31(11):3875–3877 (1966).

Grethe et al., "Syntheses in the Isoquinoline Series. Synthesis of 2,3–Dihydro–4(1H)–isoquinolones," *J. Org. Chem.* 33(2):491–494 (1968).

Hiroi et al., "A Highly Efficient and Recyclable Chiral Director for Asymmetric Synthesis of Sulfoxides," *Chemistry Letters* pp. 1595–1598 (1980).

Hiroi et al., "Studies on Chiral Organo–Sulfur Compounds. I. Asymmetric Synthesis of Sulfoxides with Optically Active o–Aminoalkylphenol Derivatives," *Chem. Pharm. Bull.* 31:3471–3485 (1983).

Kametani et al., "Studies on the Synthesis of Heterocyclic Compounds. Part 687. Asymmetric Synthesis of Salsolidine," *J. Chem. Soc. Perkin Trans. 1* pp. 579–581 (1977).

Kang et al., "Rhodium(I)–catalysed Asymmetric hydrogenation of Imines," *J. Chem. Soc. Chem. Commun.* pp. 1466–1467 (1988).

Kienzle et al., "1,5–Dihydroimidazoquinazolinones as blood platelet aggregation inhibitors," *Eur. J. Med. Chem.—Chem. Ther.* 17:547–556 (1982).

Kozlov et al., "Reductive animation of 1–acetylcyclohexene by nitriles," *Vestsi Akad. Navuk BSSR, Ser. Khim. Navuk* pp. 55–58 (1977).

Mori et al., "Formic Acid Reduction. XI. Reduction of Schiff Bases," *Chem. Pharm. Bull.* 19:1722–1727 (1971).

Standridge et al., "Phenylalkylamines with Potential Psychotherapeutic Utility. 1. 2–Amino–1–(2, 5–dimethoxy–4–methylphenyl) butane," *J. Med. Chem.* 19:1400–1404 (1976).

Standridge et al., "Phenylalkylamines with Potential Psychotherapeutic Utility. 2. Nuclear Substituted 2–Amino–1–phenylbutanes," *J. Med. Chem.* 22:154–162 (1980).

NPS 467

NPS R-467

NPS S-467

NPS 568

NPS R-568

NPS S-568

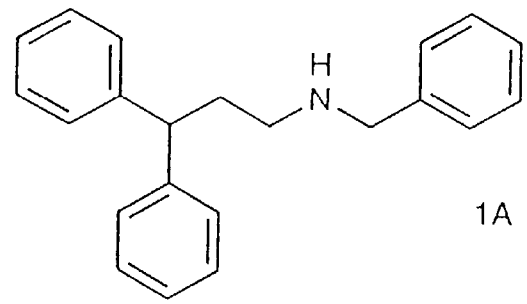
1A
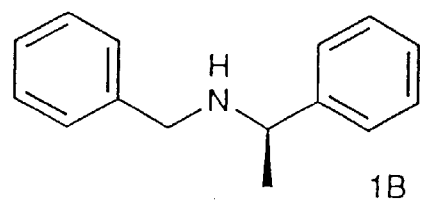
1B
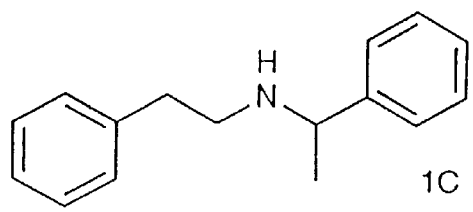
1C
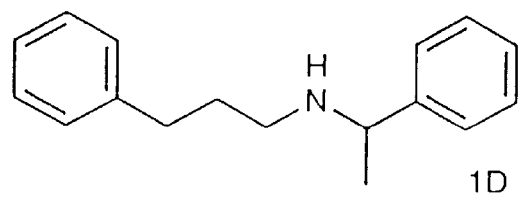
1D
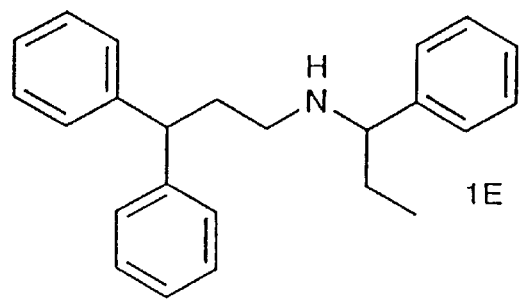
1E
*Fig. 1-2*

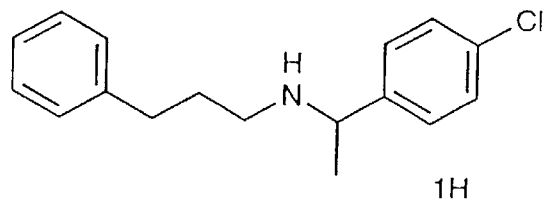
1H
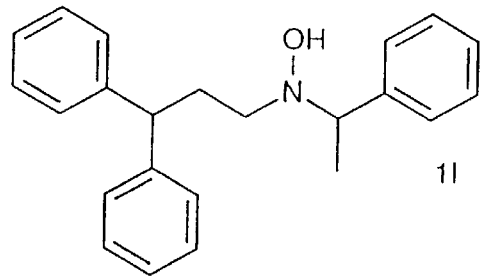
1I
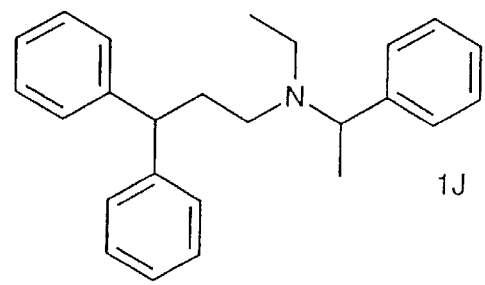
1J
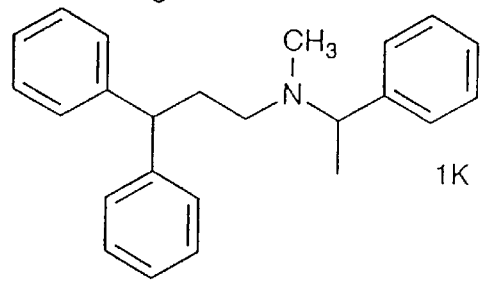
1K
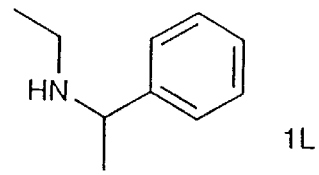
1L
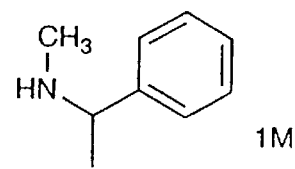
1M
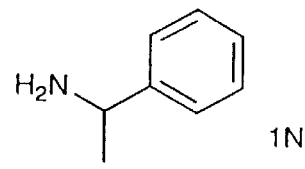
1N
Fig. 1-3

1O

1P

1Q

1R

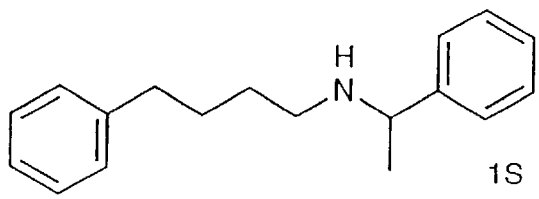
1S
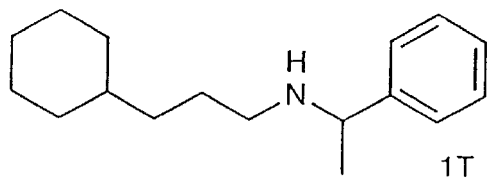
1T
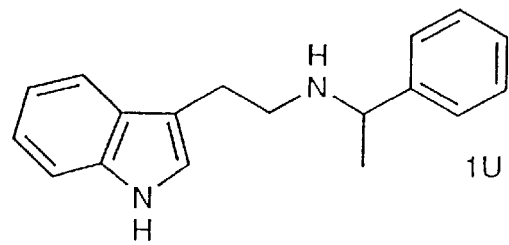
1U
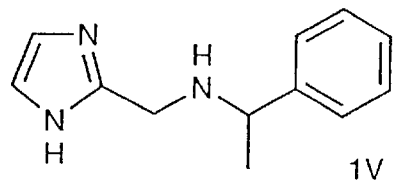
1V
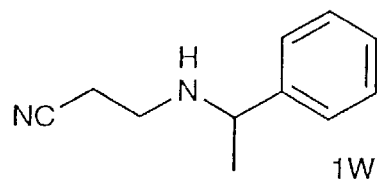
1W
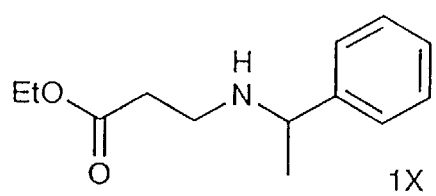
1X
*Fig. 1-5*
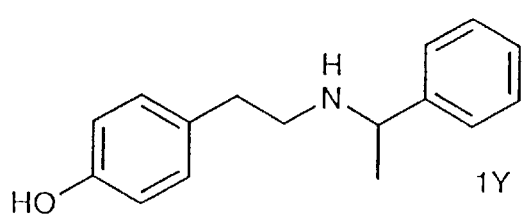
1Y
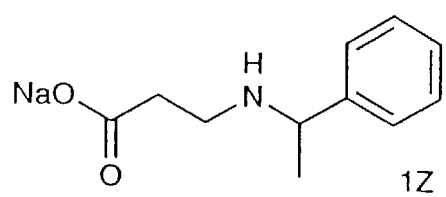
1Z

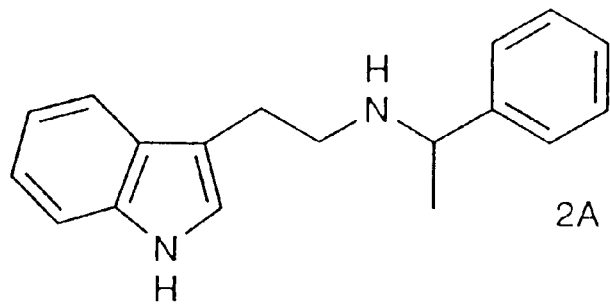
2A
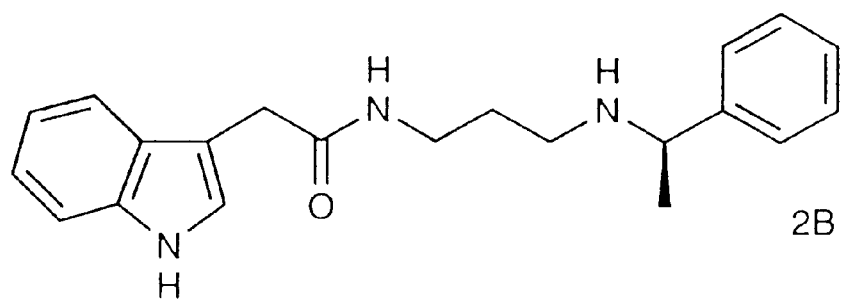
2B
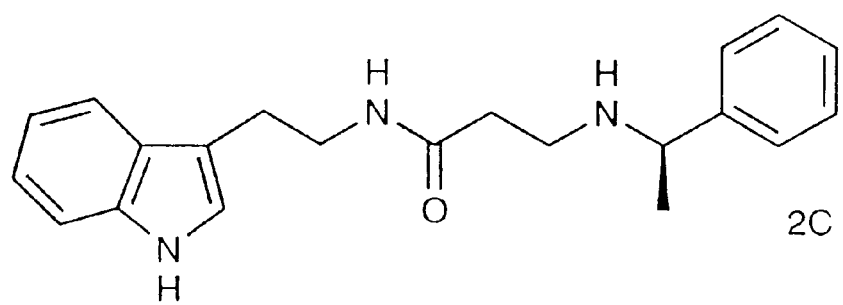
2C
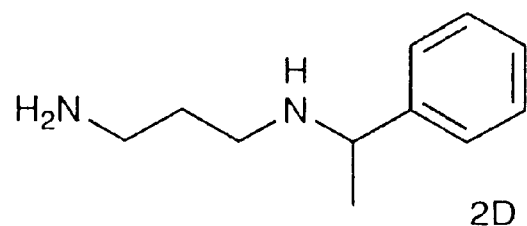
2D
*Fig. 1-6*

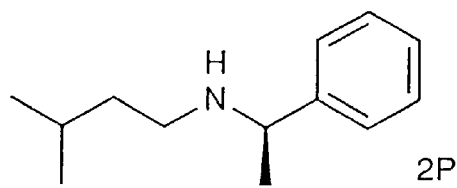
2P
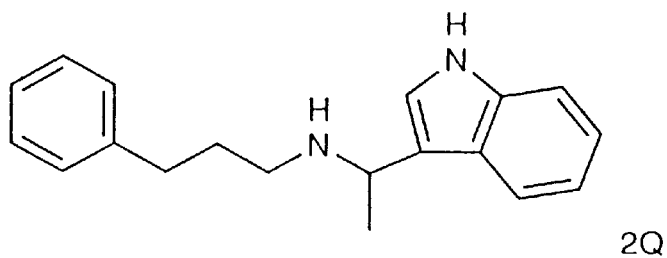
2Q
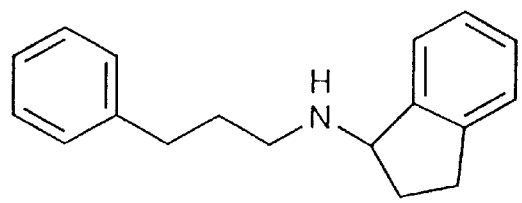
2R
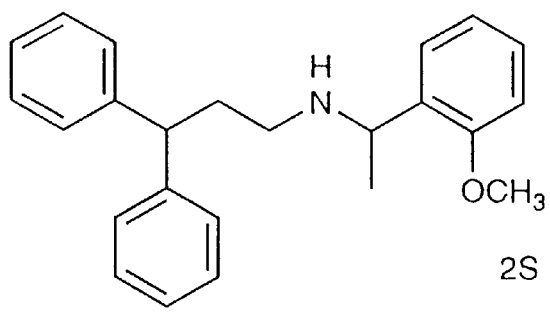
2S
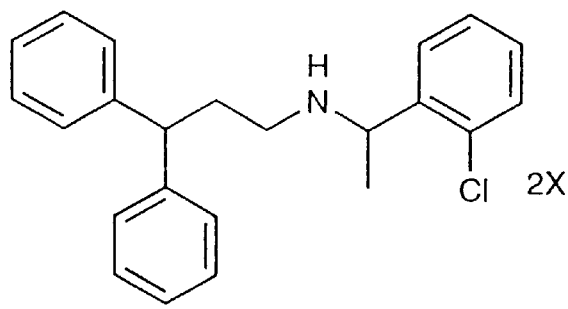
2X
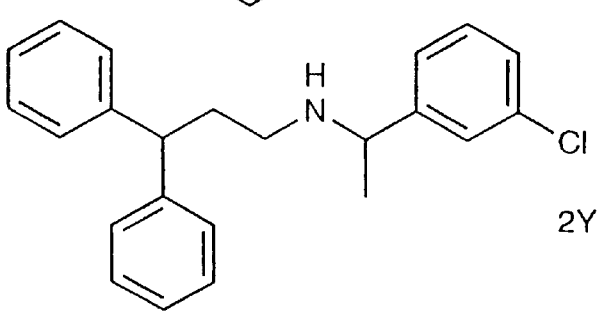
2Y
Fig. 1-9

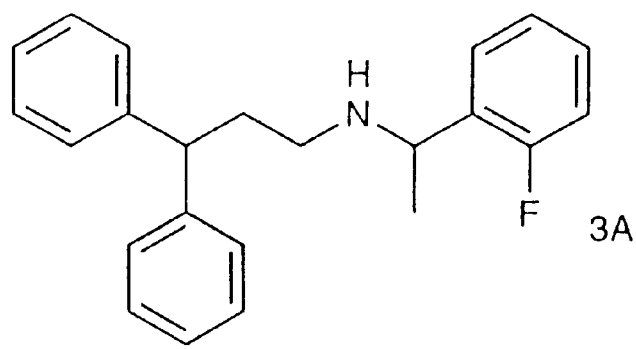
3A
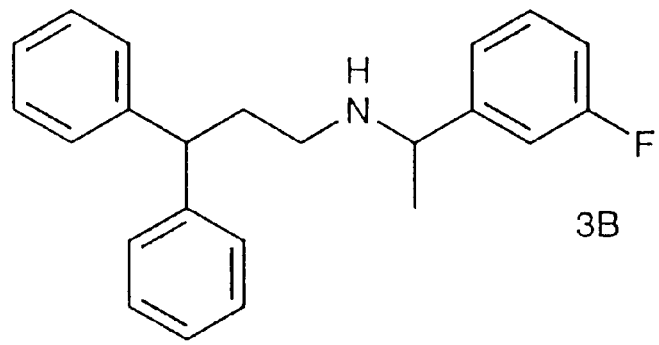
3B
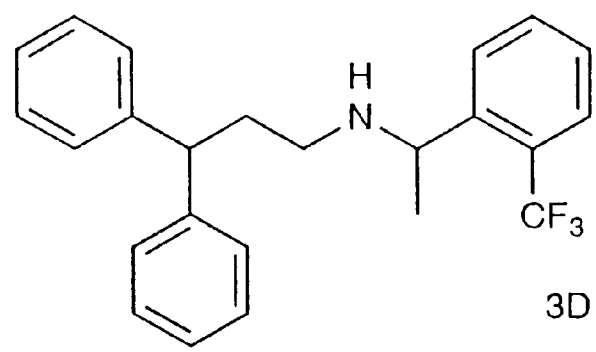
3D
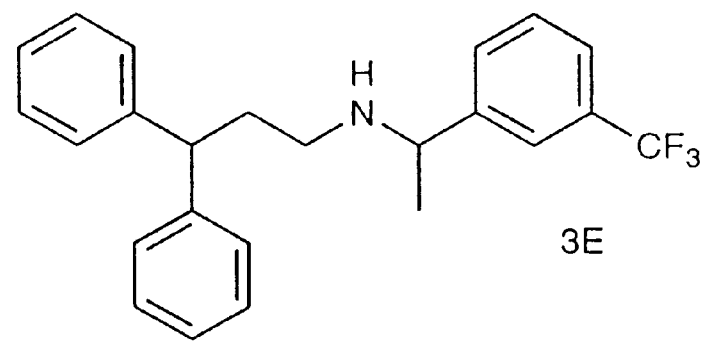
3E
Fig. 1-10

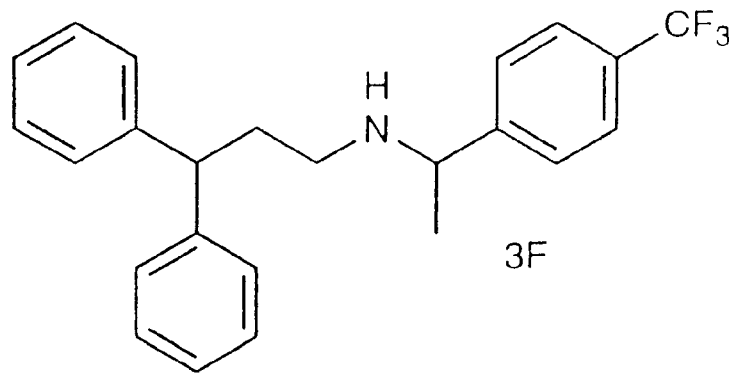
3F
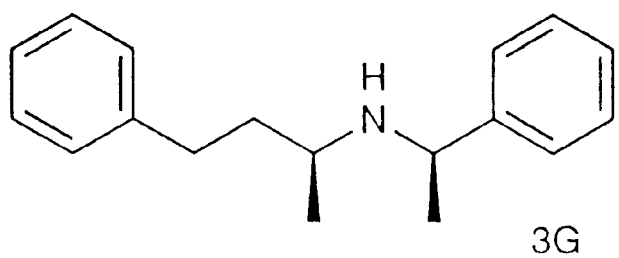
3G
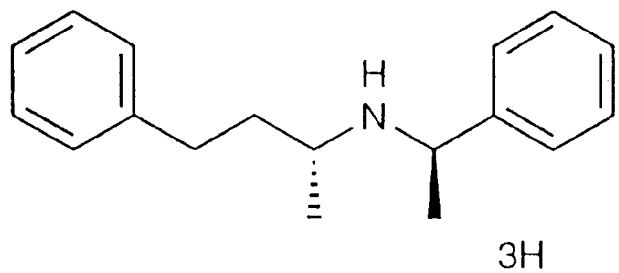
3H
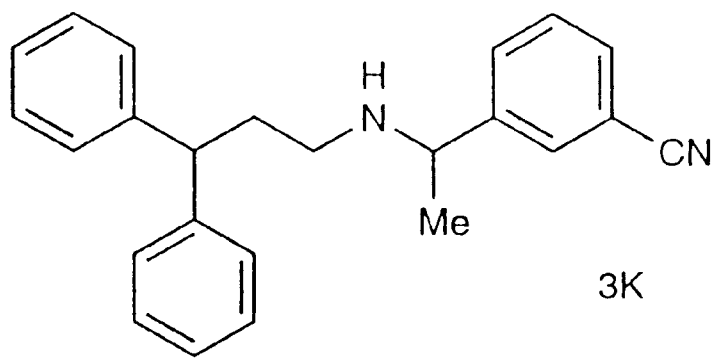
3K
Fig. 1-11

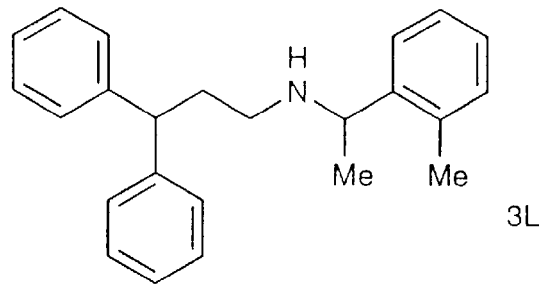
3L
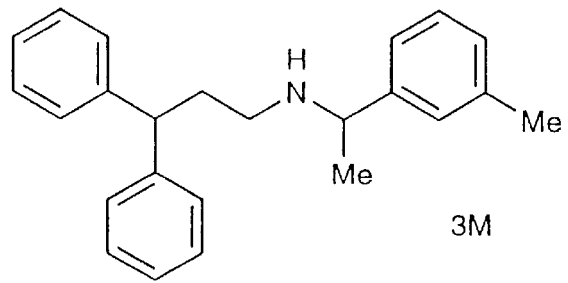
3M
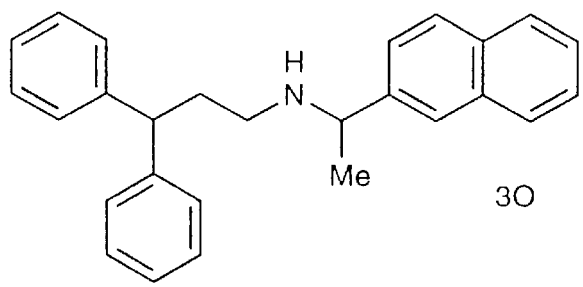
3O
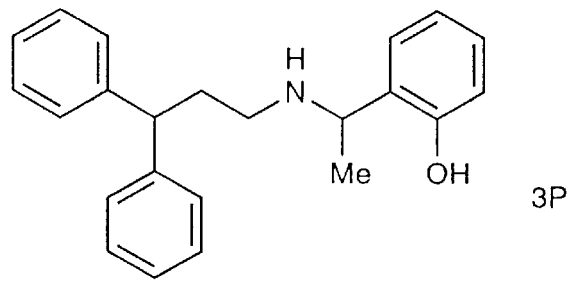
3P
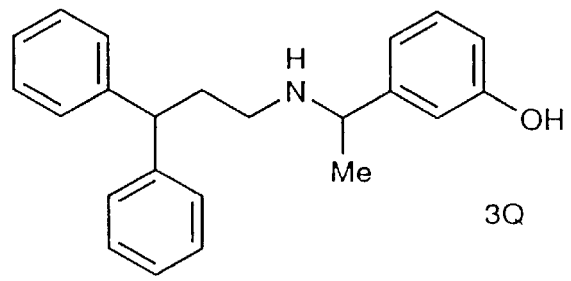
3Q
Fig. 1-12

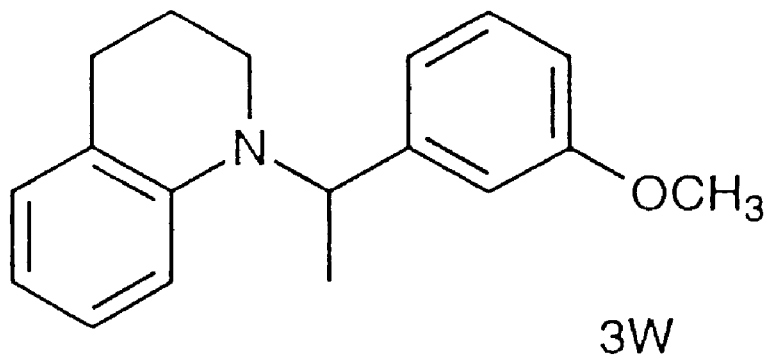
3W
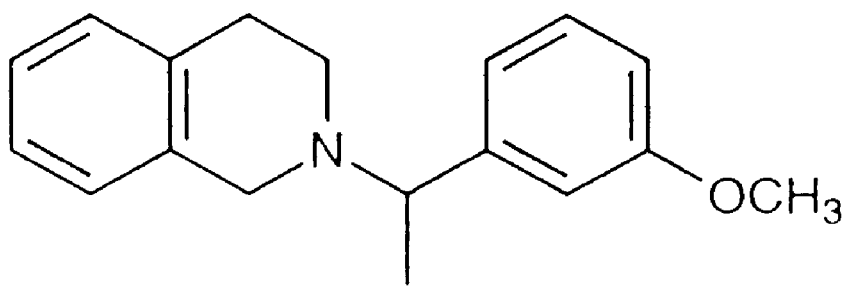
3X
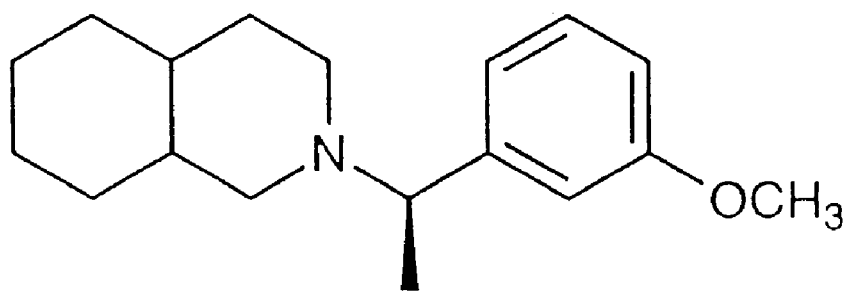
3Y
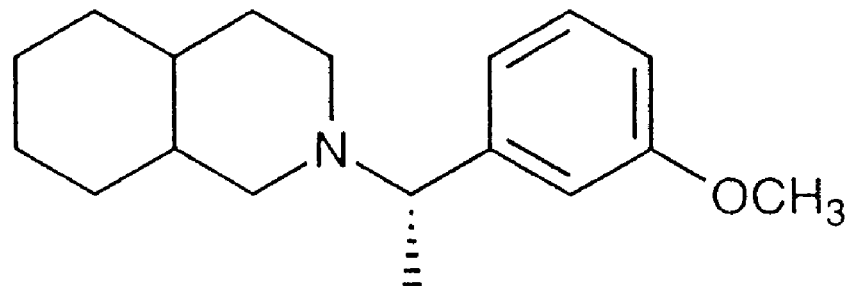
3Z
Fig. 1-14

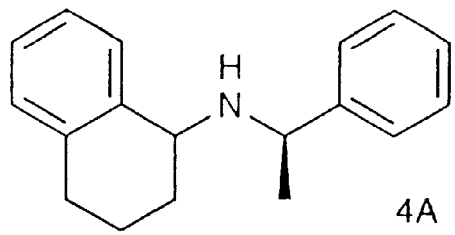
4A
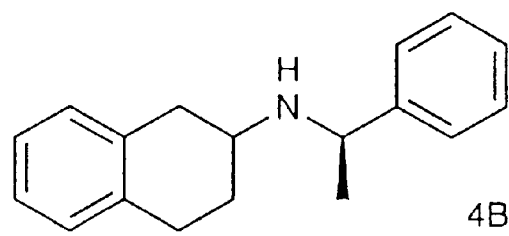
4B
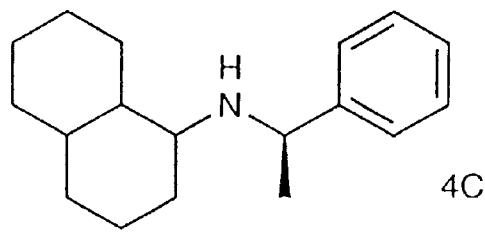
4C
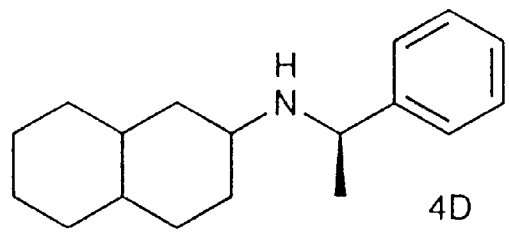
4D
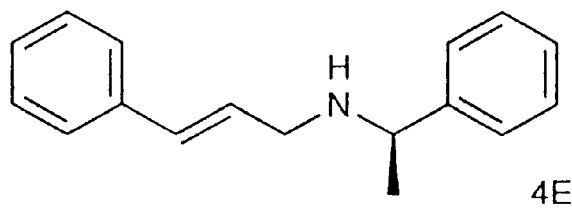
4E
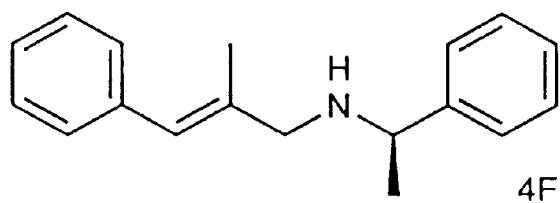
4F
*Fig. 1-15*

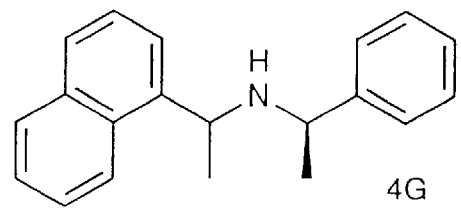
4G
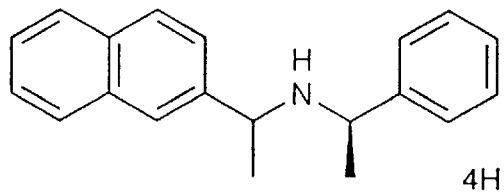
4H
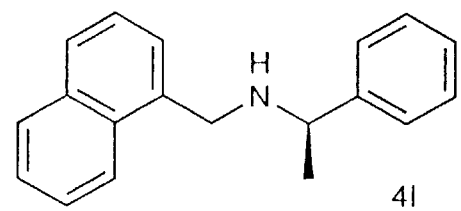
4I
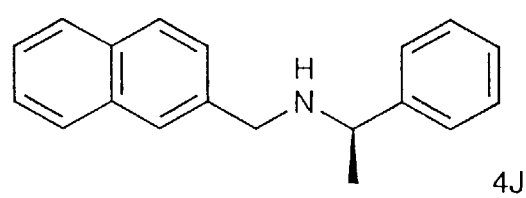
4J
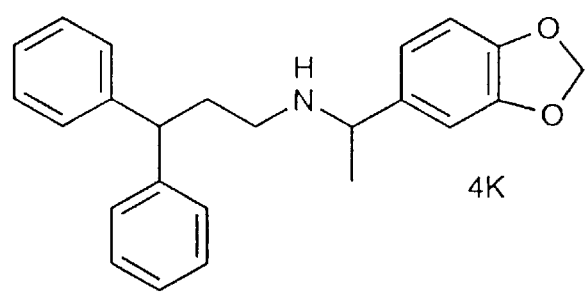
4K
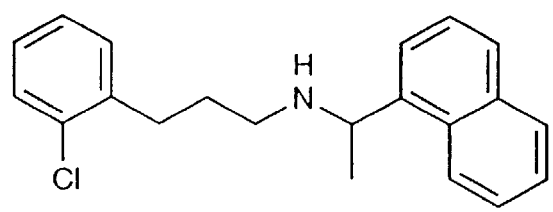
4L
*Fig. 1-16*

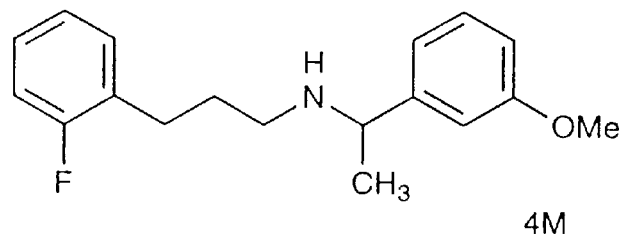
4M
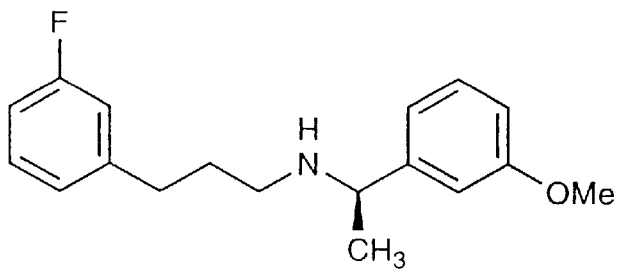
4N
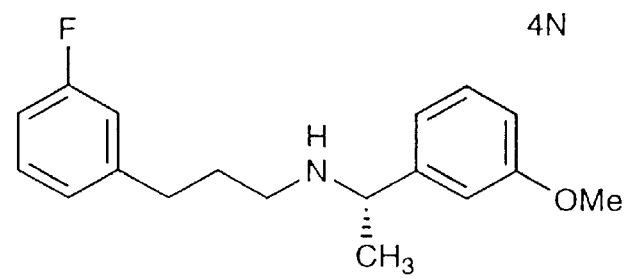
4O
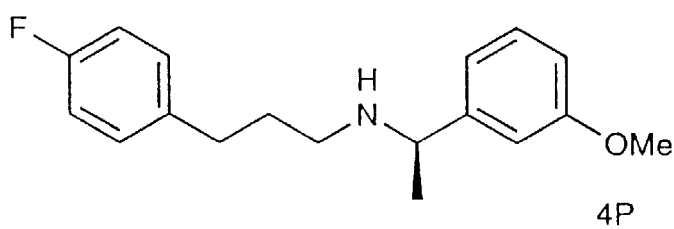
4P
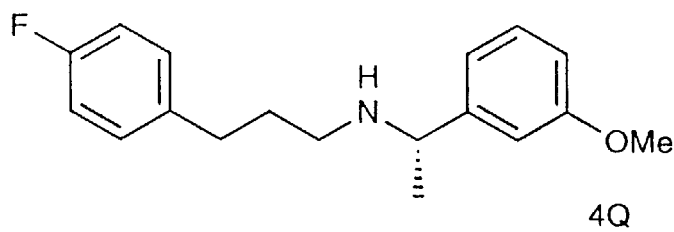
4Q
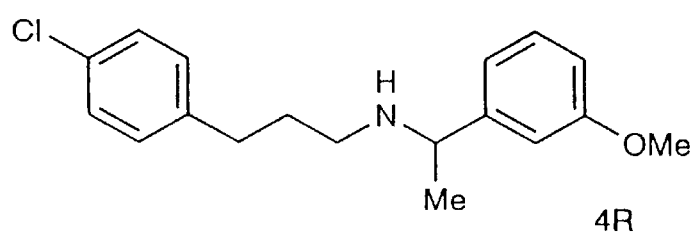
4R
*Fig. 1-17*

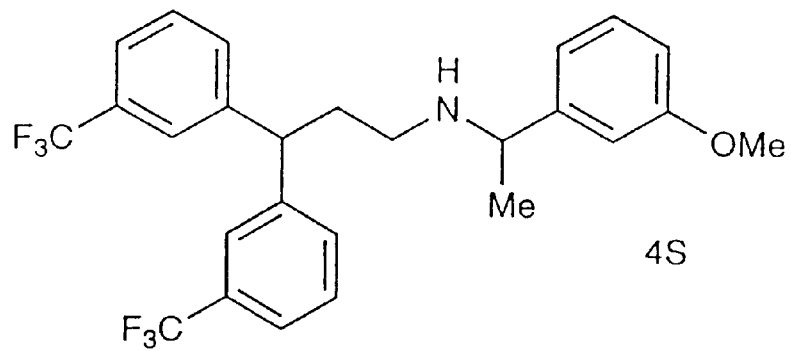
4S
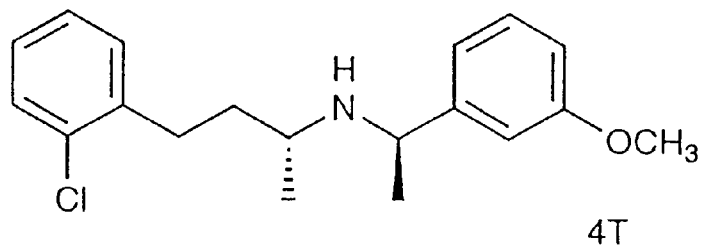
4T
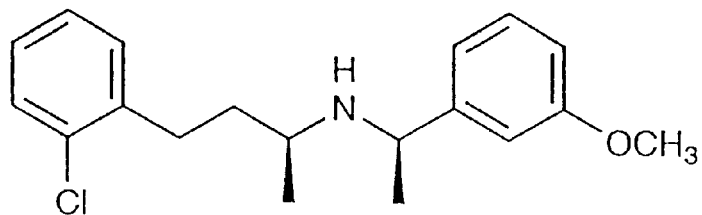
4U
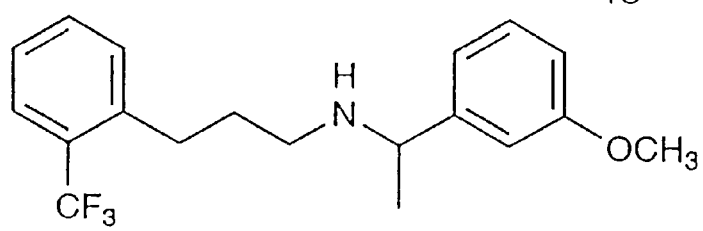
4V
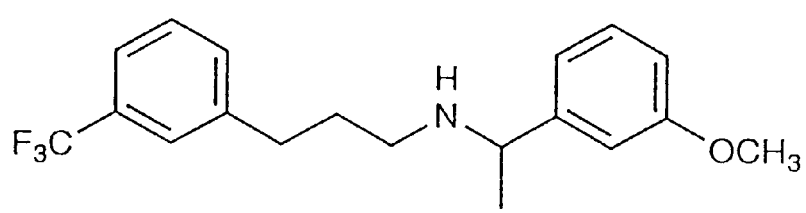
4W
*Fig. 1-18*

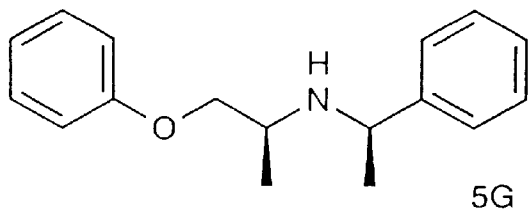
5G
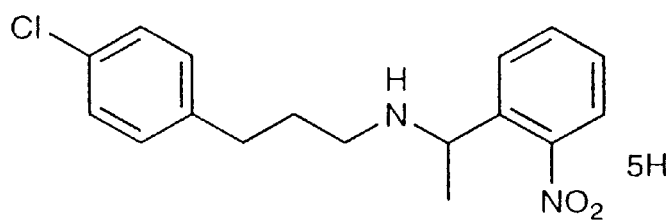
5H
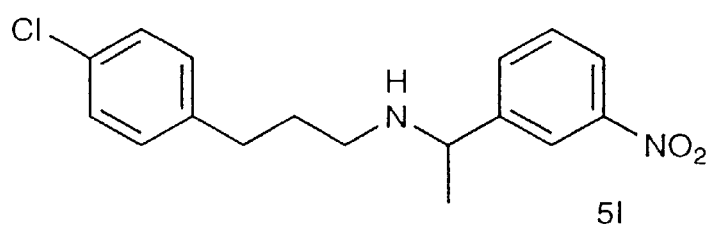
5I
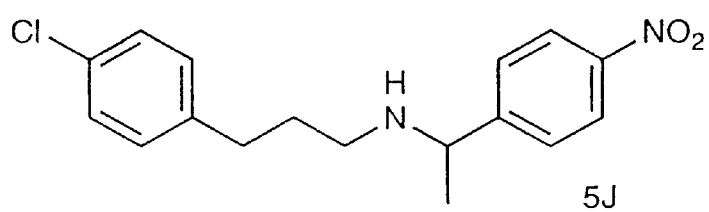
5J
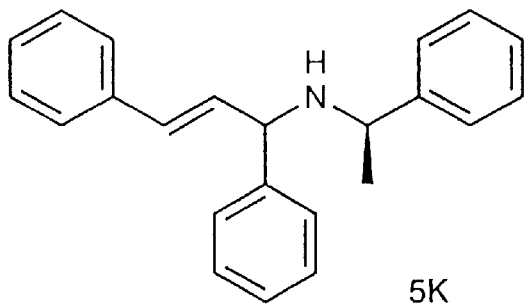
5K
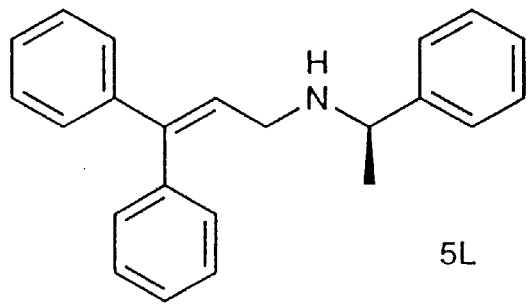
5L
*Fig. 1-21*

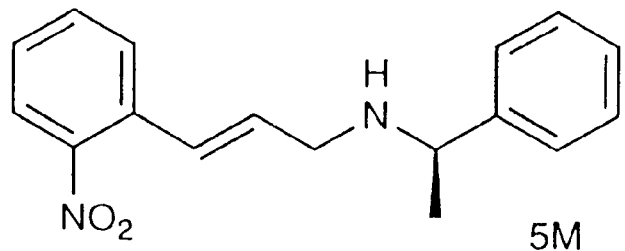
5M
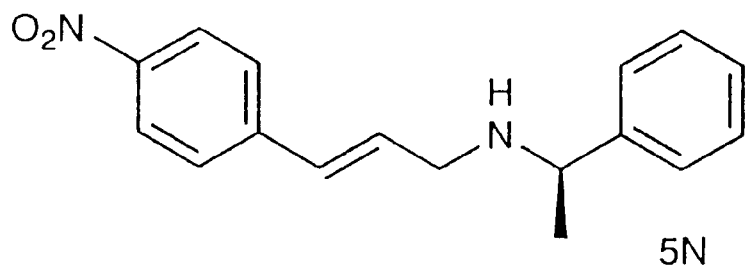
5N
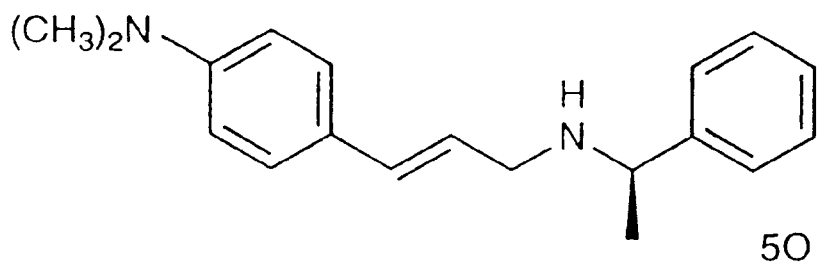
5O
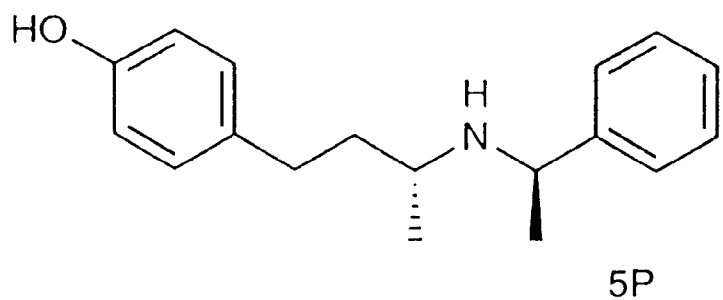
5P
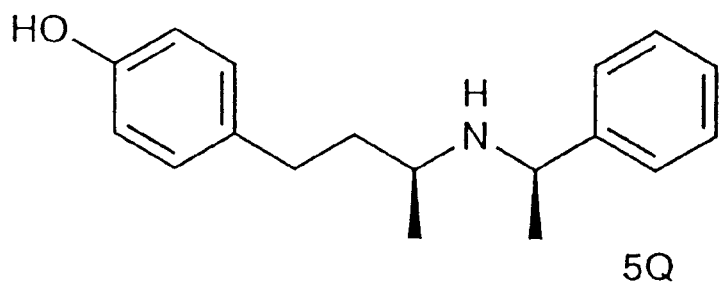
5Q
Fig. 1-22

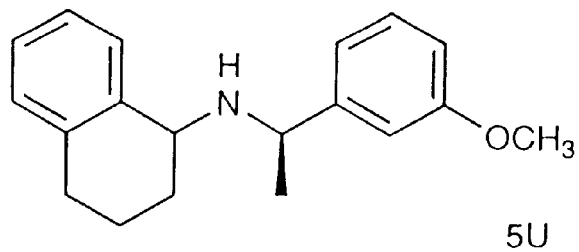
5U
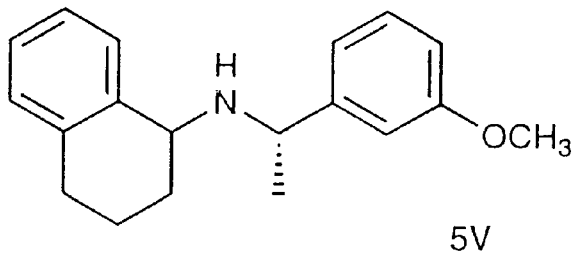
5V
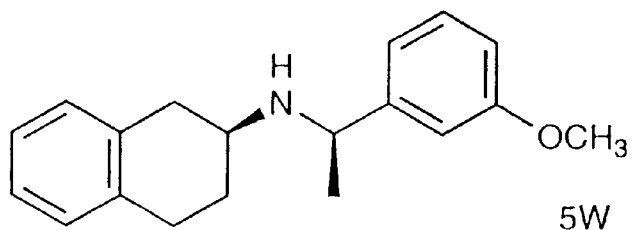
5W
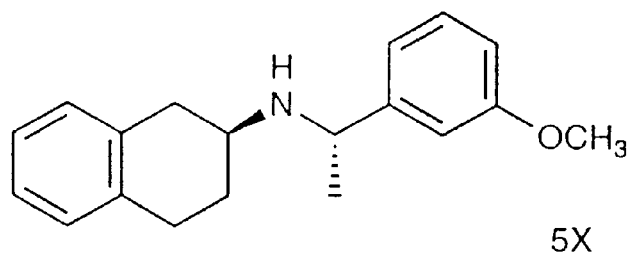
5X
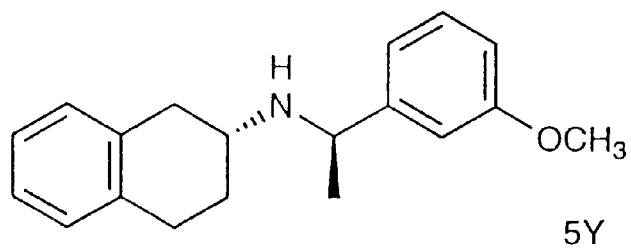
5Y
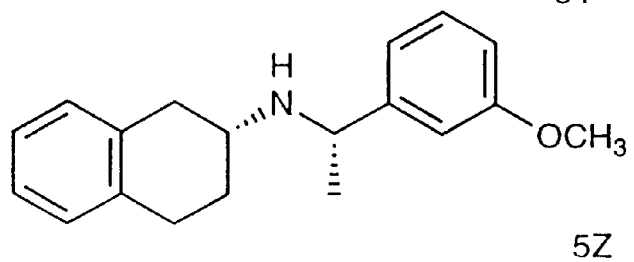
5Z
*Fig. 1-23*

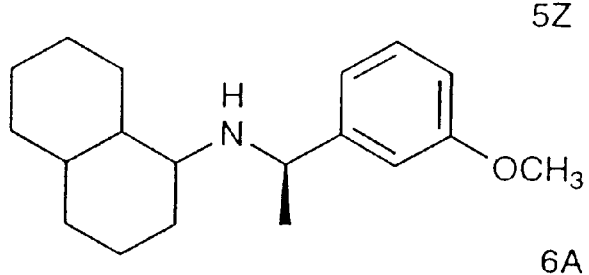
5Z
6A
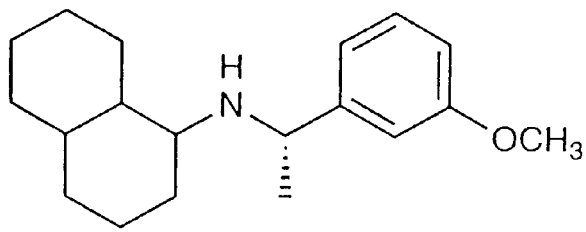
6B
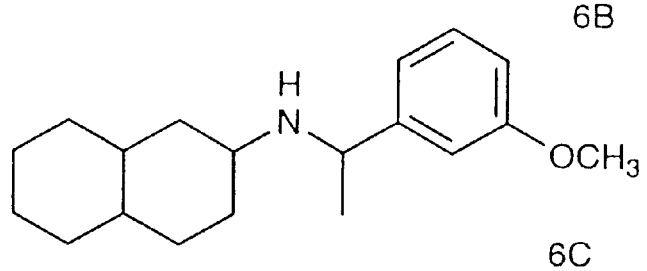
6C
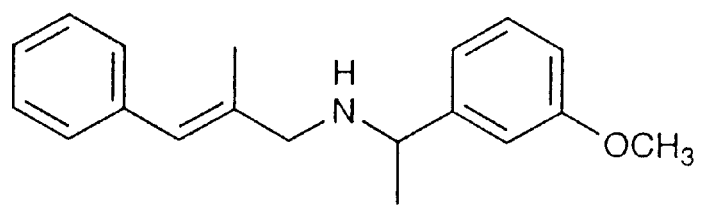
6D
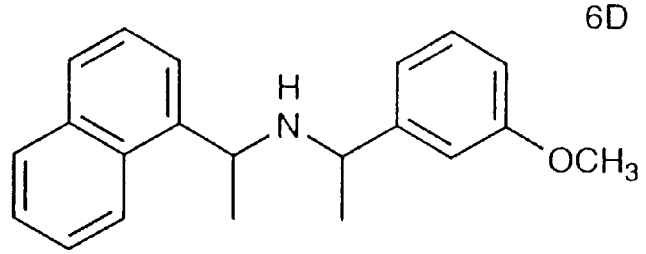
6E
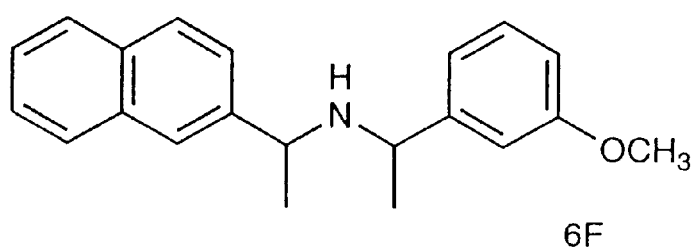
6F
*Fig. 1-24*

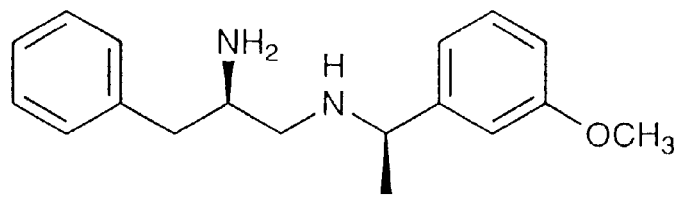
6G
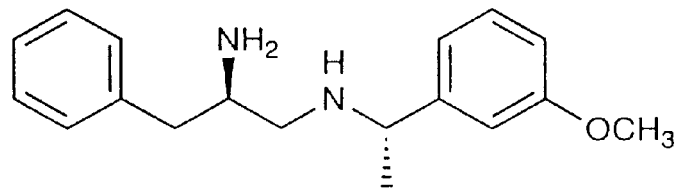
6H
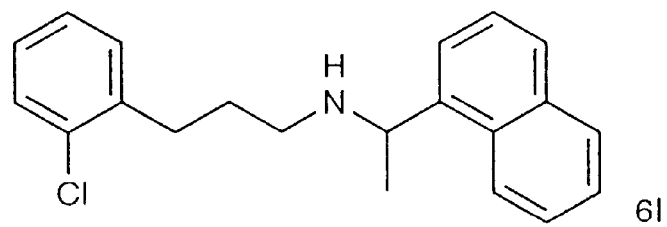
6I
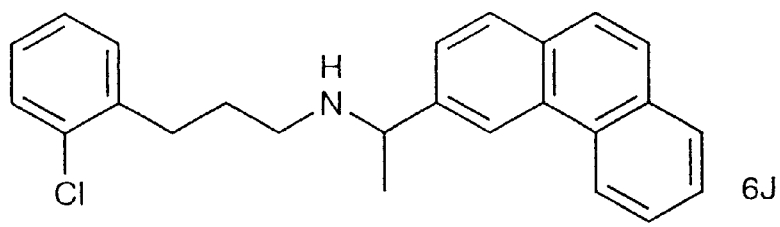
6J
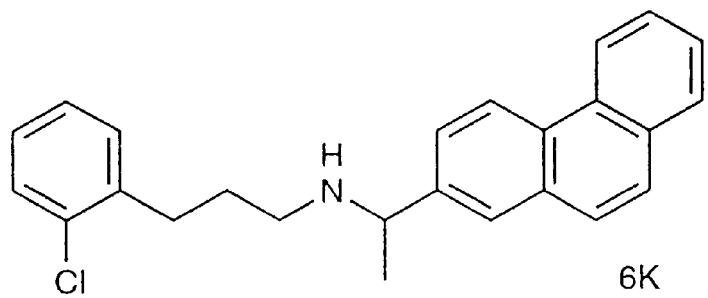
6K
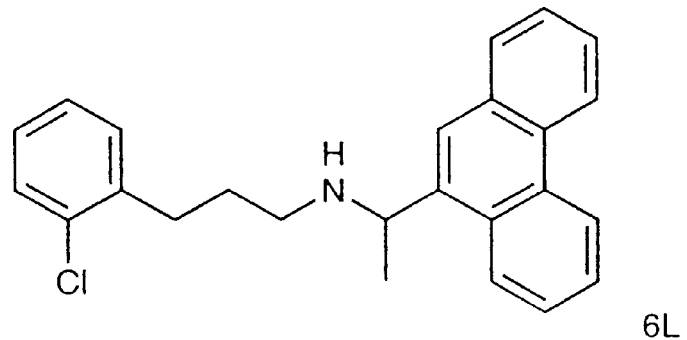
6L
*Fig. 1-25*

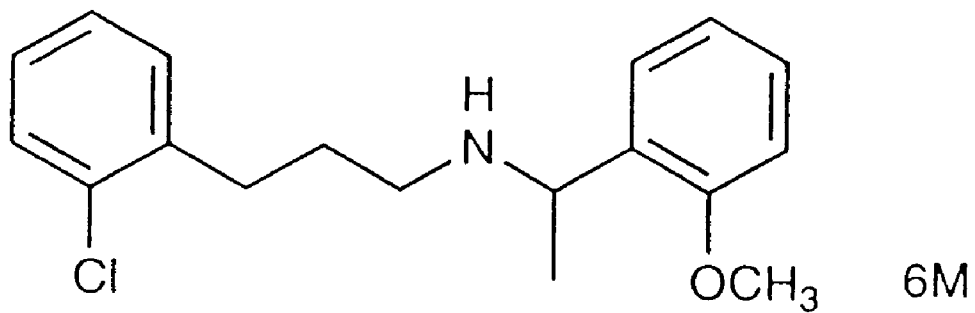
6M
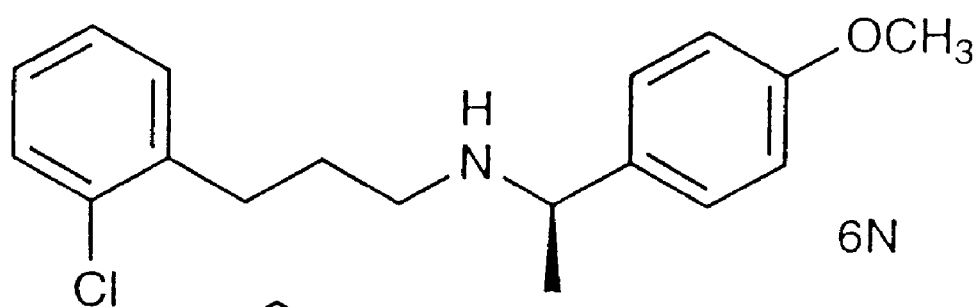
6N
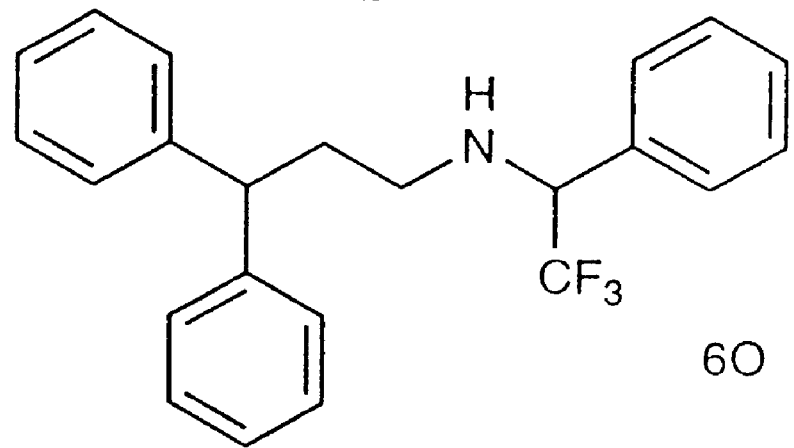
6O
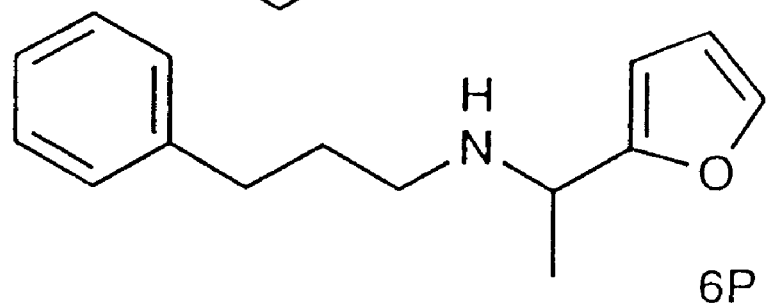
6P
Fig. 1-26

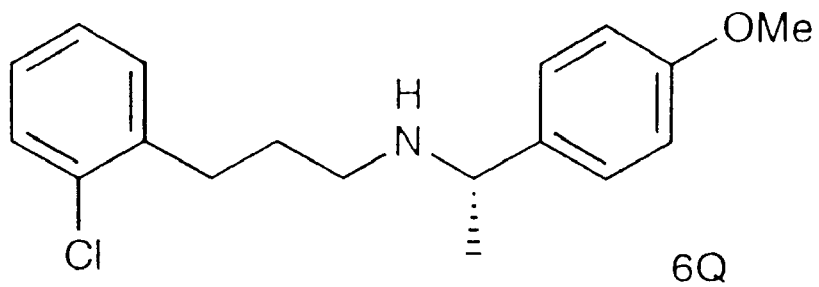
6Q
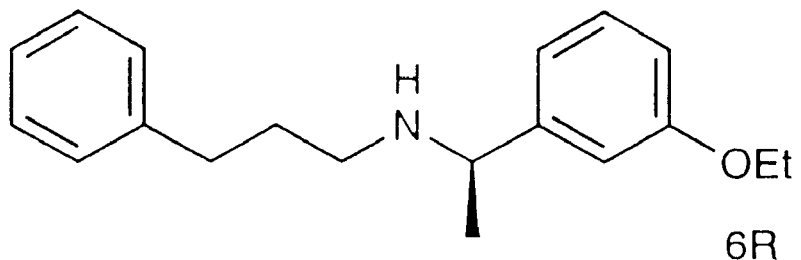
6R
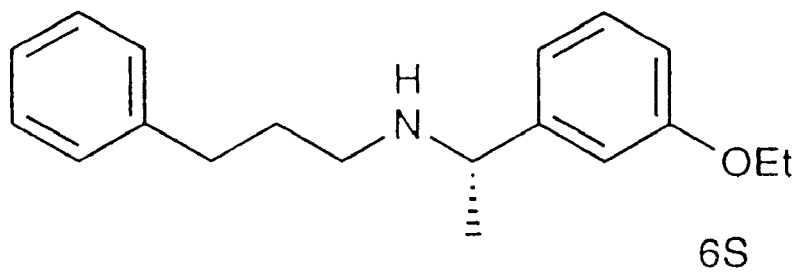
6S
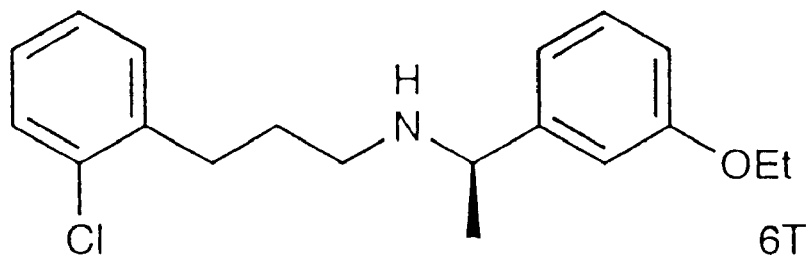
6T
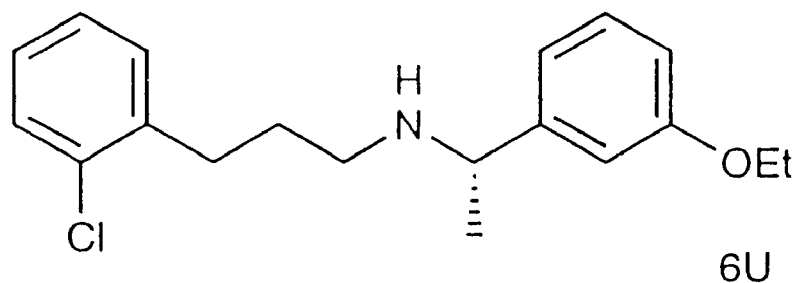
6U
Fig. 1-27

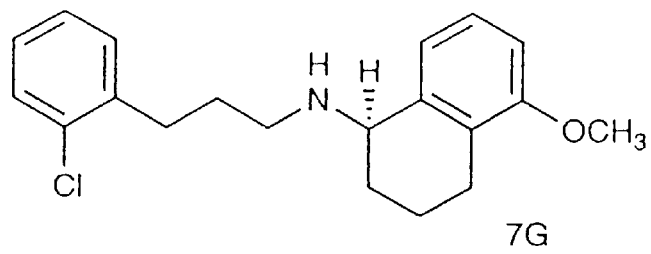
7G
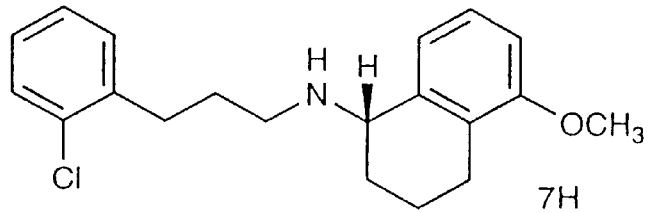
7H
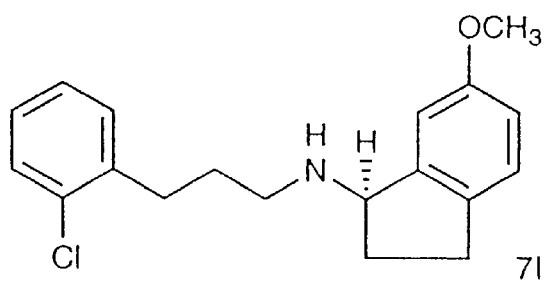
7I
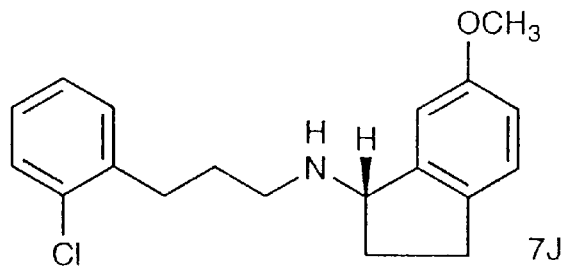
7J
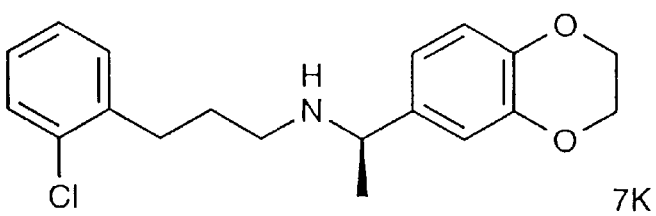
7K
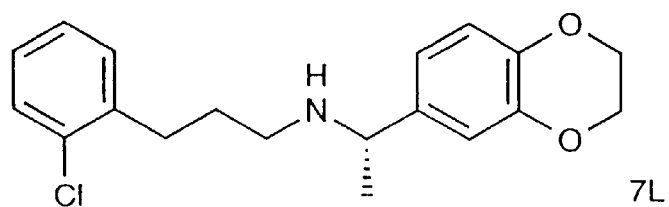
7L
Fig. 1-30

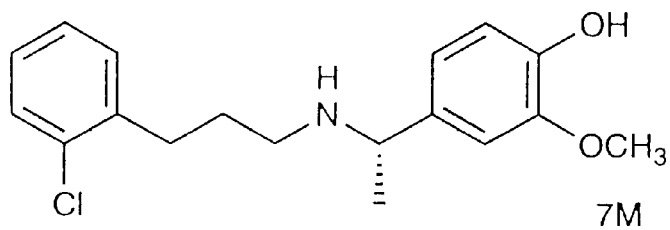
7M
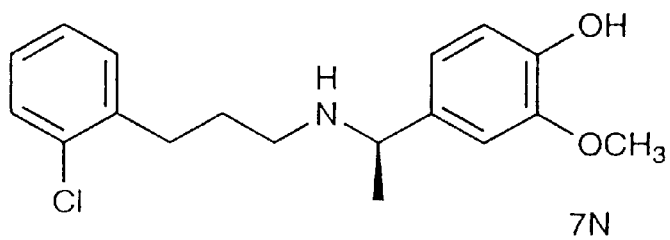
7N
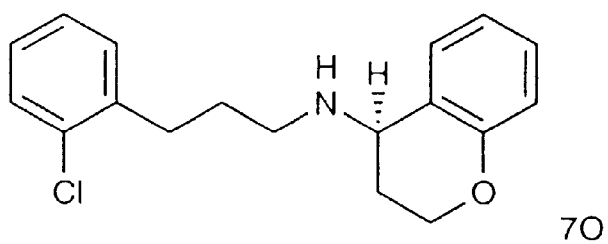
7O
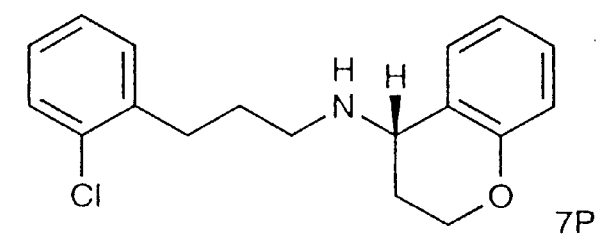
7P
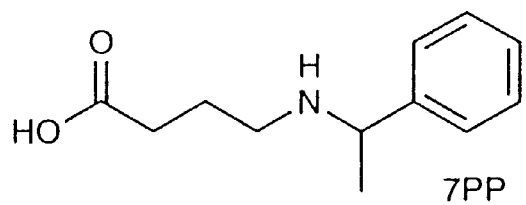
7PP
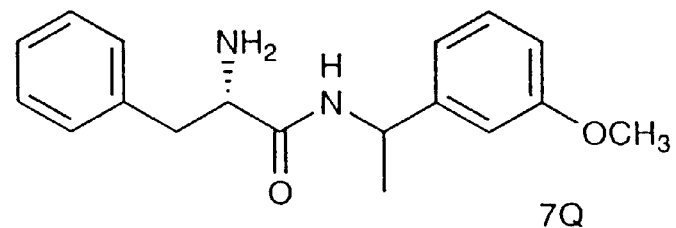
7Q
*Fig. 1-31*

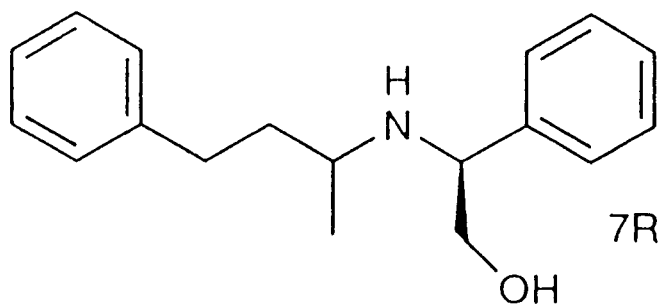
7R
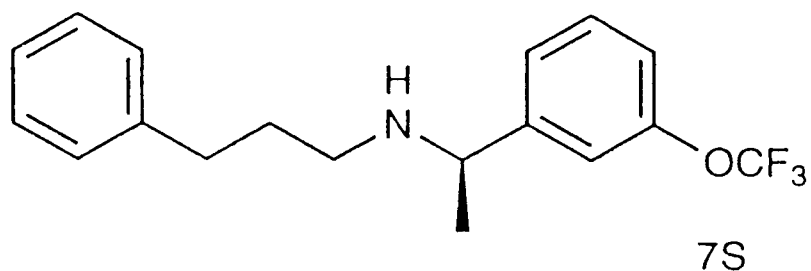
7S
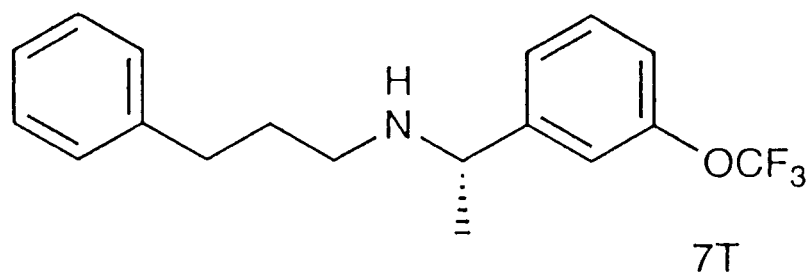
7T
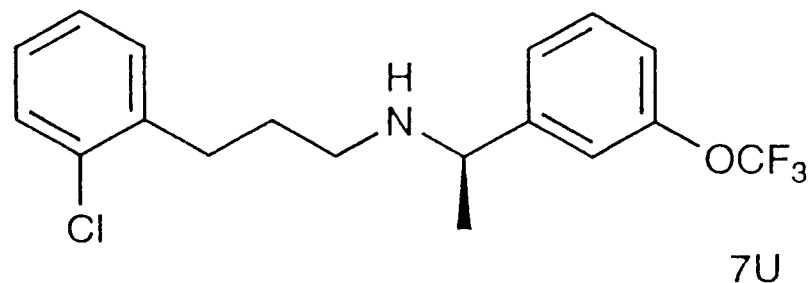
7U
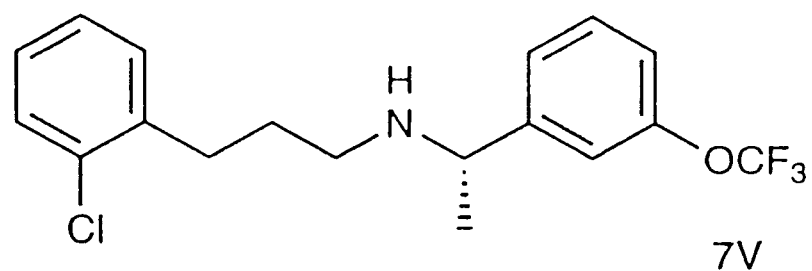
7V
*Fig. 1-32*

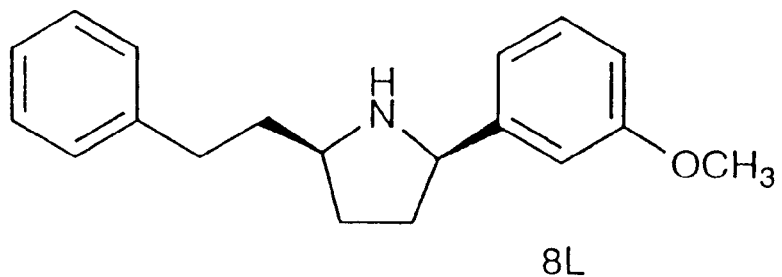
8L
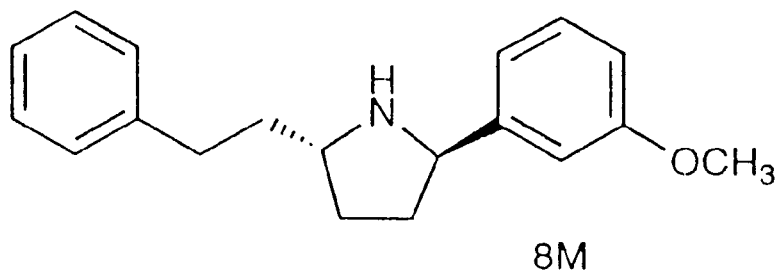
8M
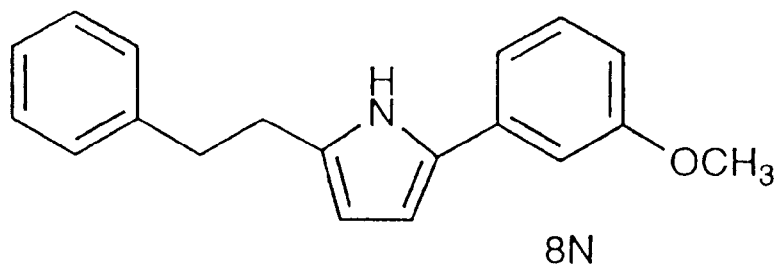
8N
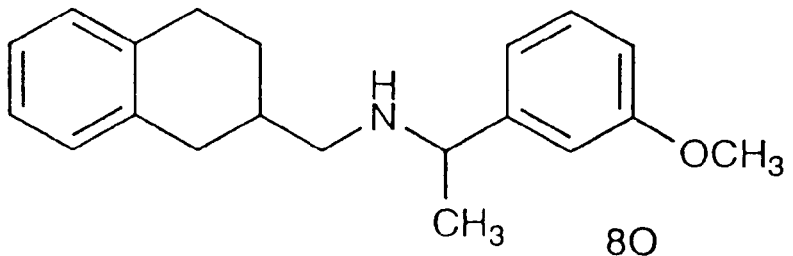
8O
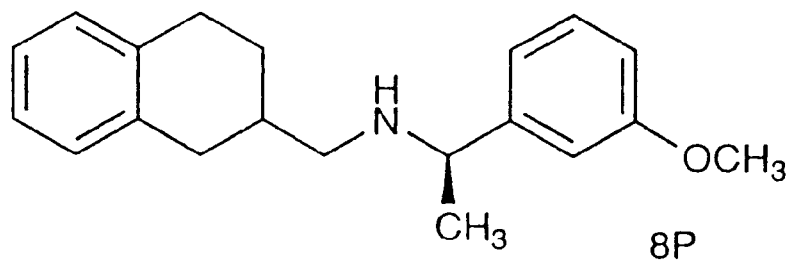
8P
*Fig. 1-36*

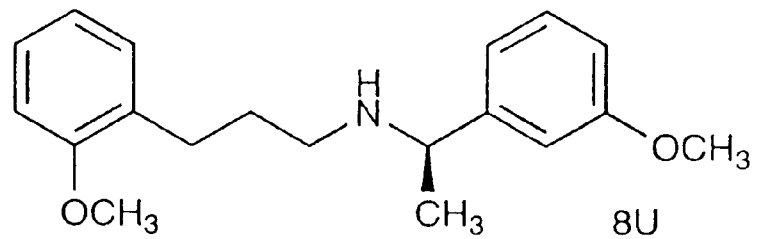
8U
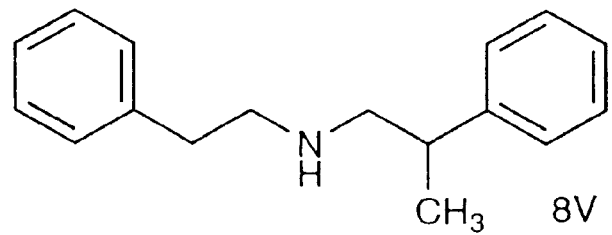
8V
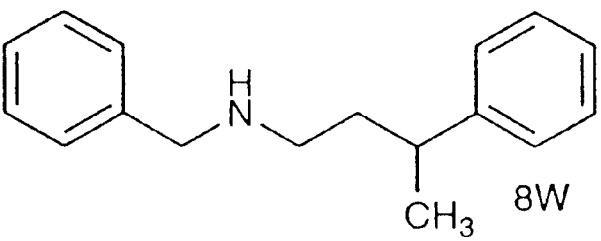
8W
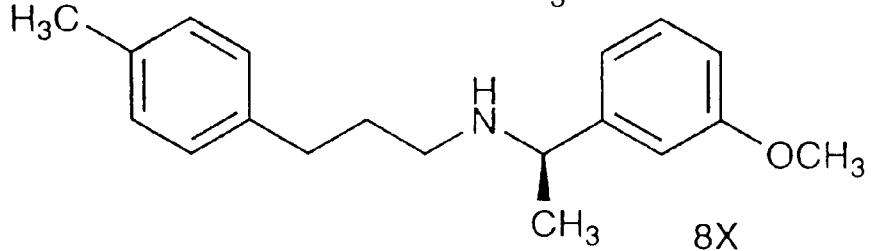
8X
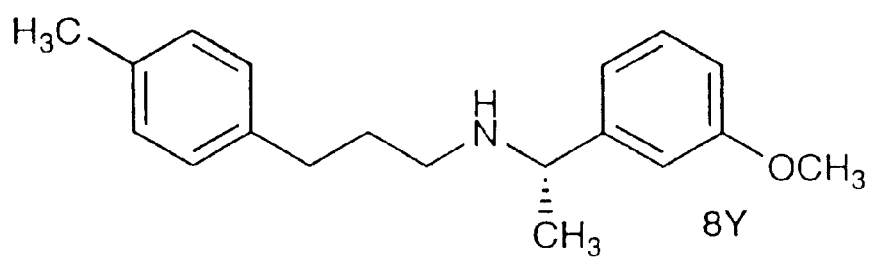
8Y
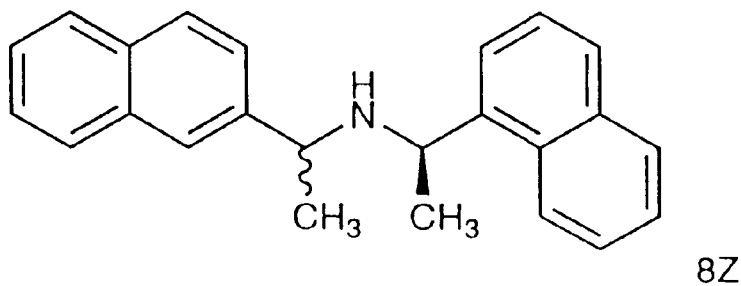
8Z
*Fig. 1-38*

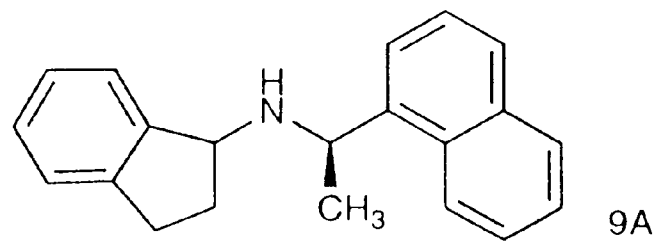
9A
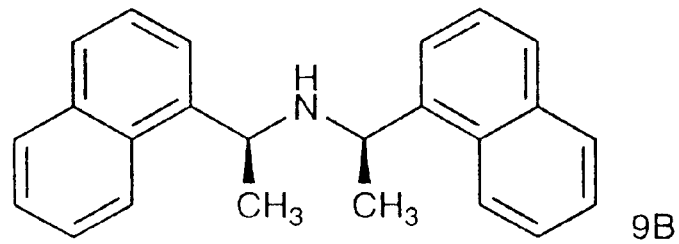
9B
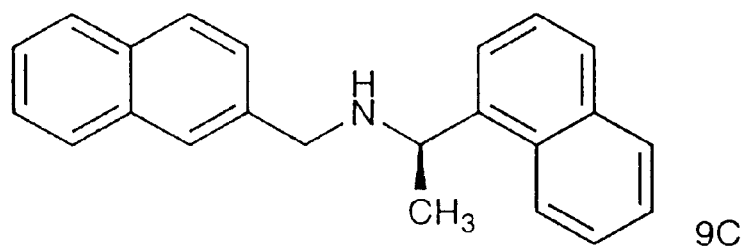
9C
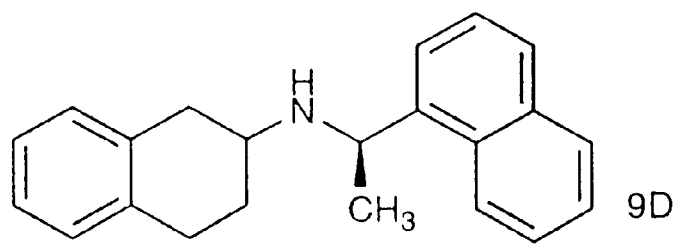
9D
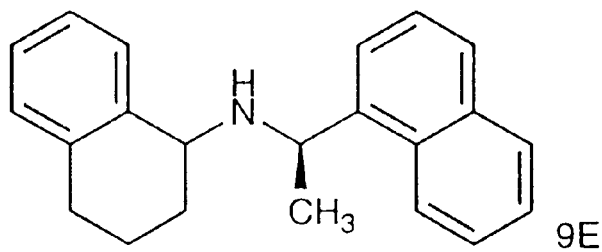
9E
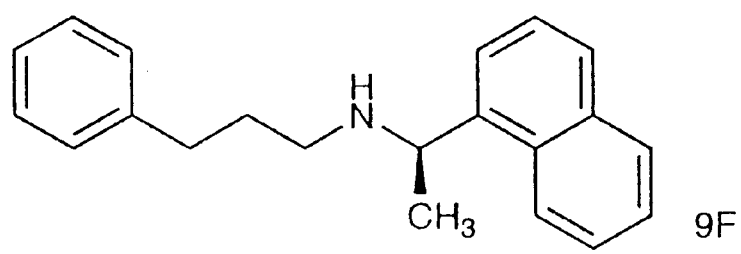
9F
*Fig. 1-39*

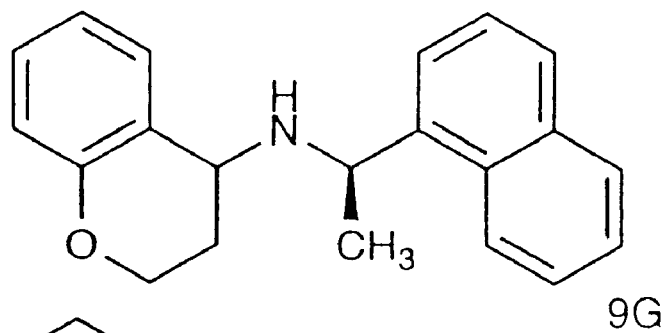
9G
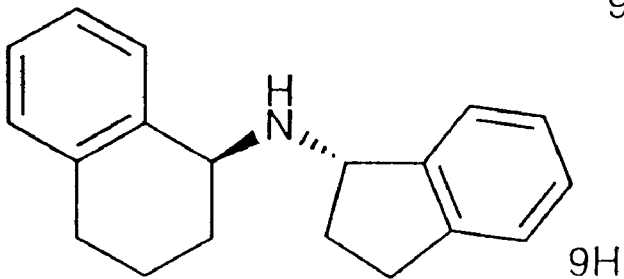
9H
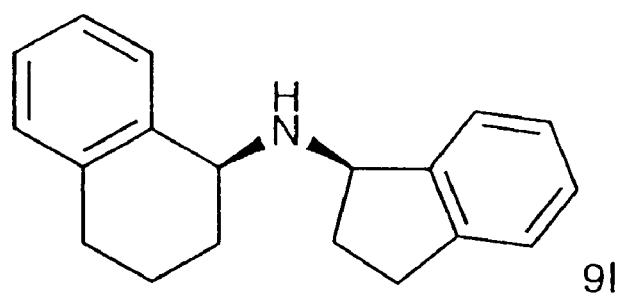
9I
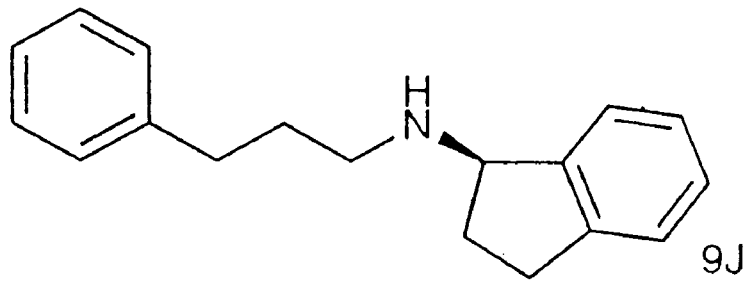
9J
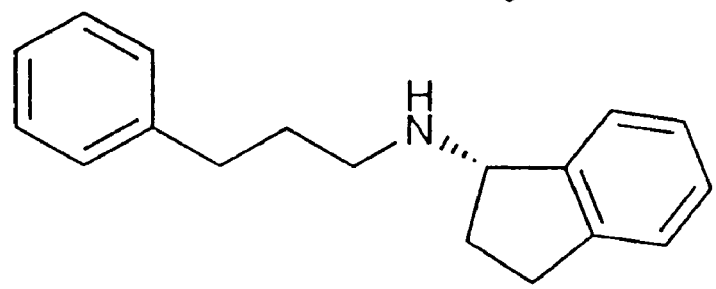
9K
*Fig. 1-40*

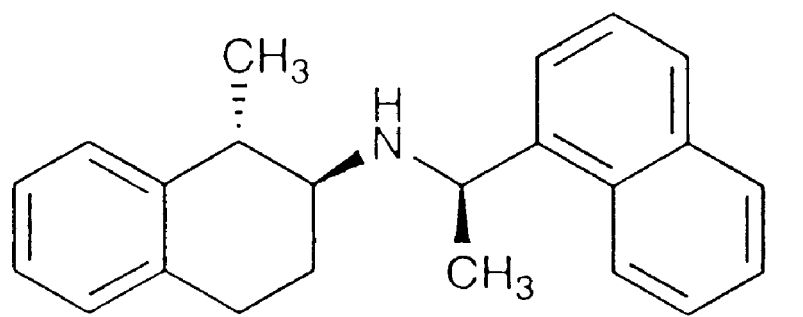
9Q
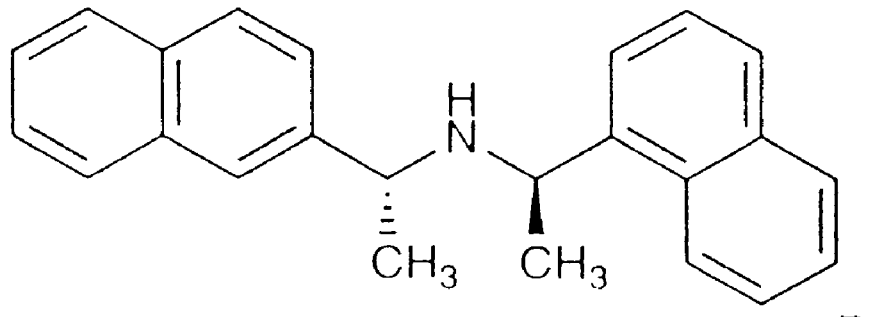
9R
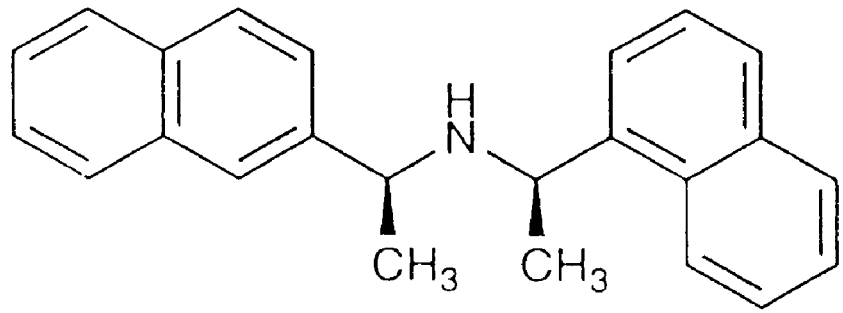
9S
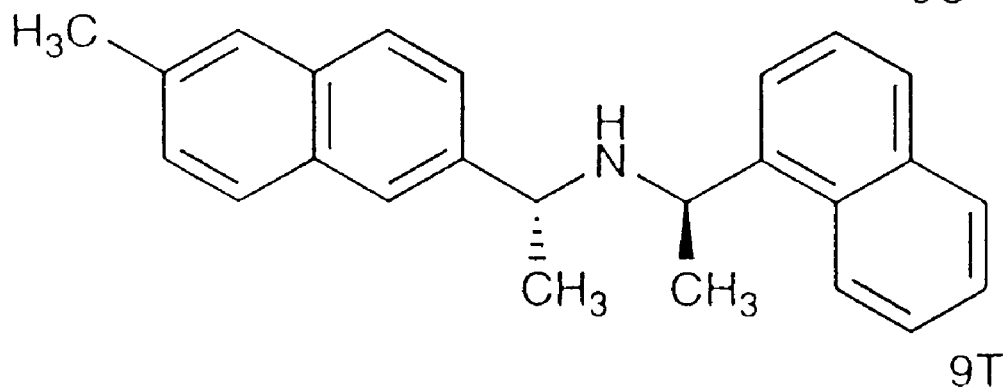
9T
Fig. 1-42

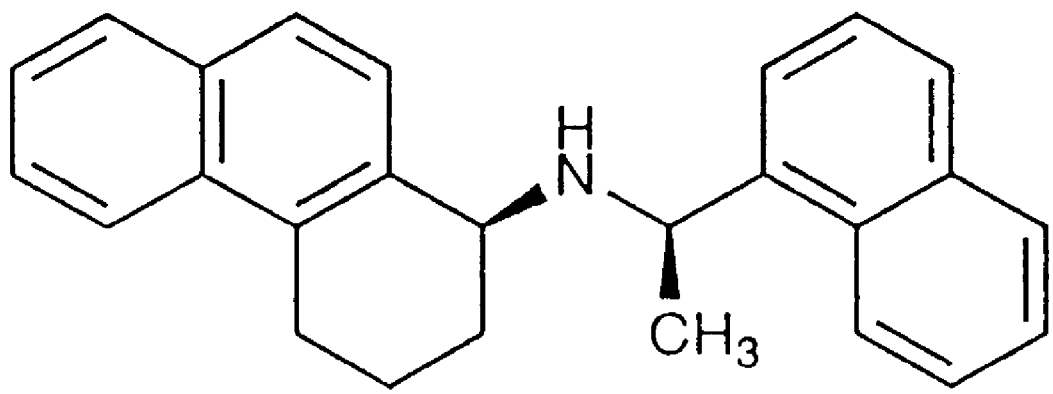
9Y
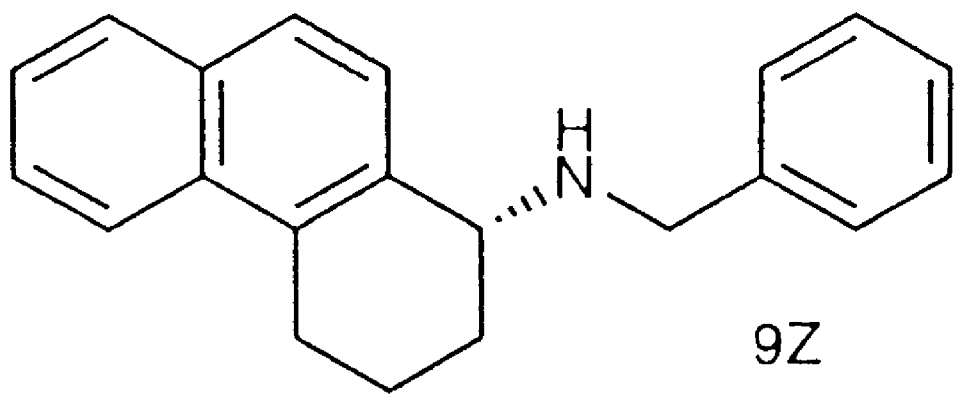
9Z
*Fig. 1-44*

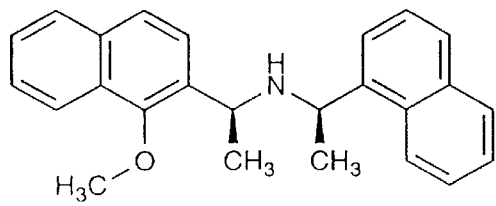
10H
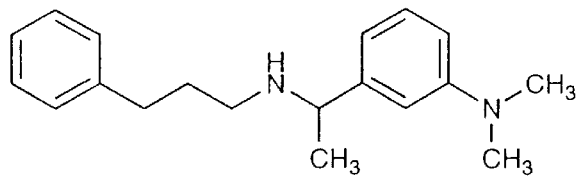
10I
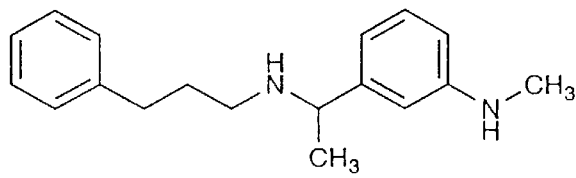
10J
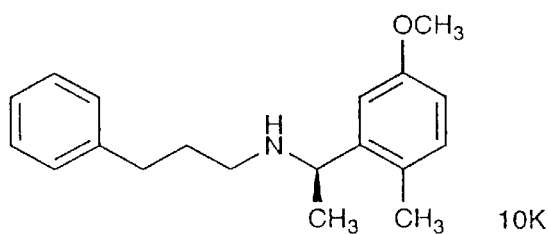
10K
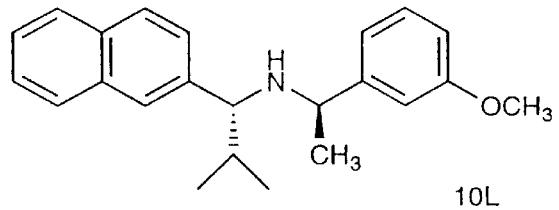
10L
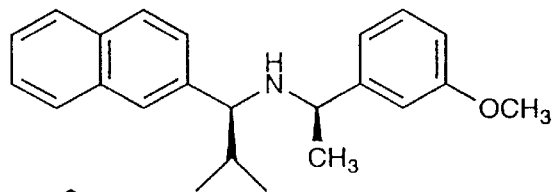
10M
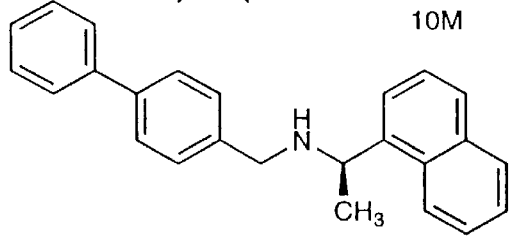
10N
Fig. 1-46

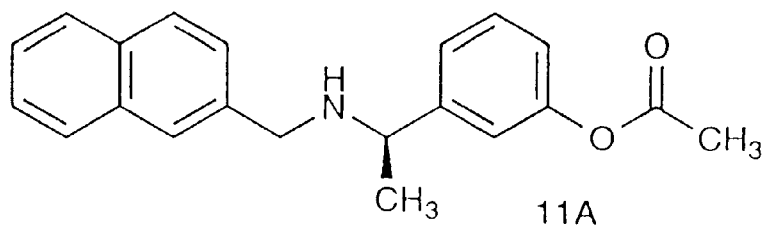
11A
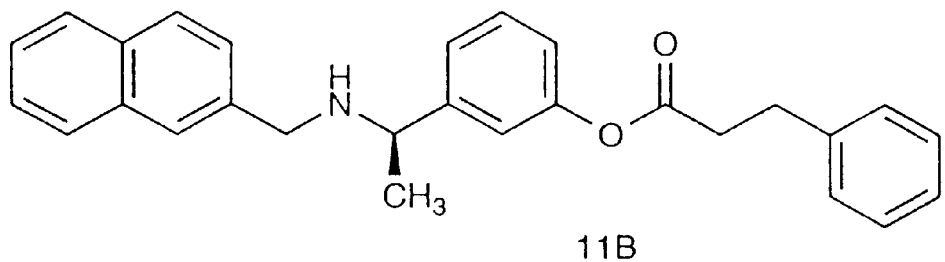
11B
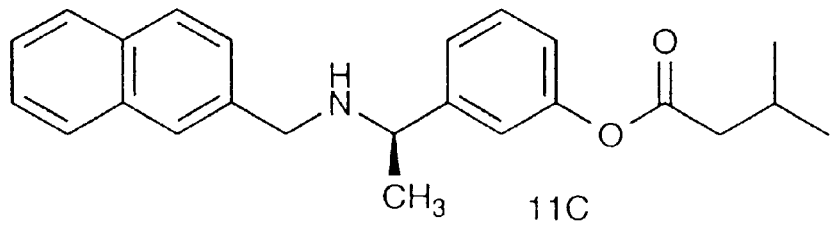
11C
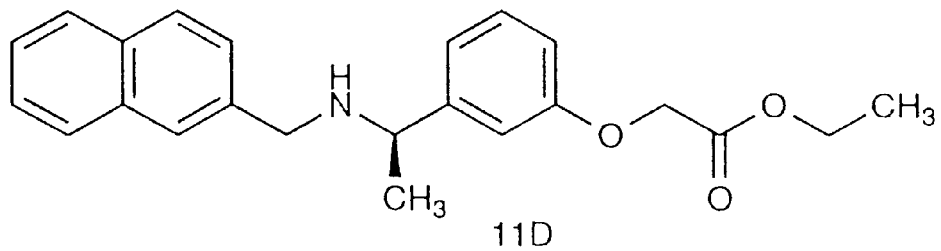
11D
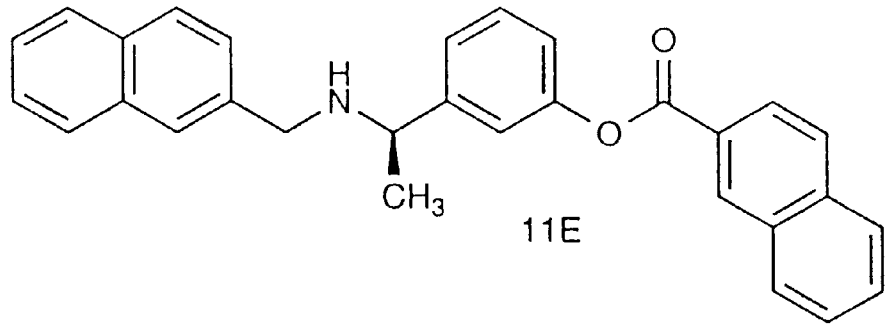
11E  NPS1084
*Fig. 1-49*

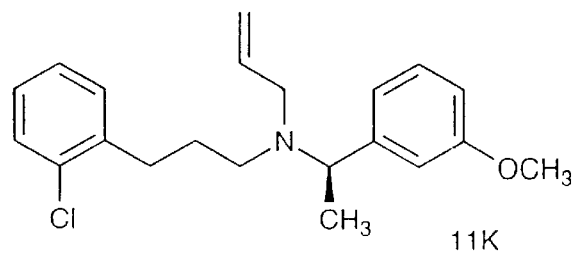
11K
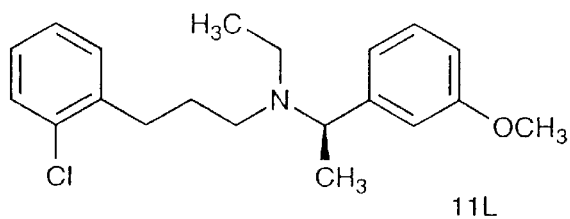
11L
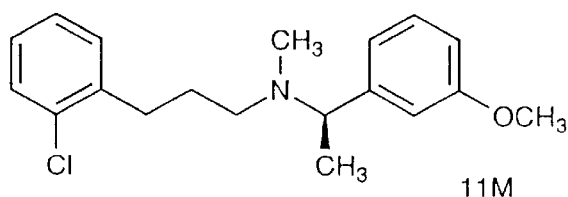
11M
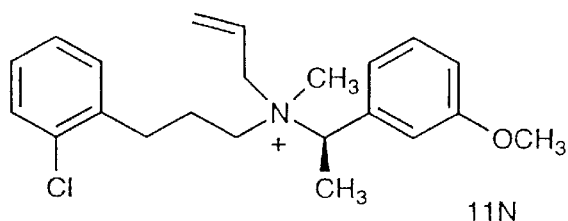
11N
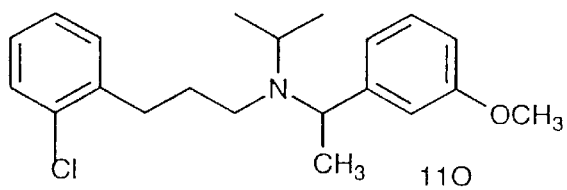
11O
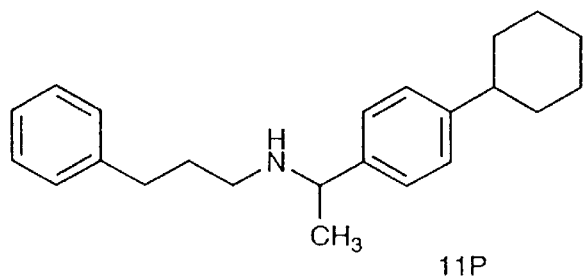
11P
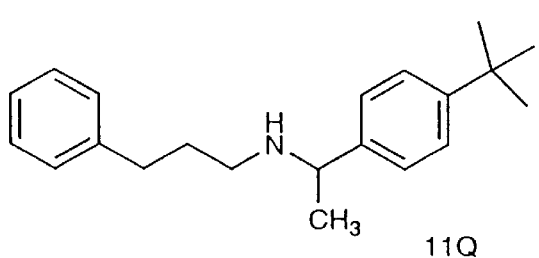
11Q
Fig. 1-51

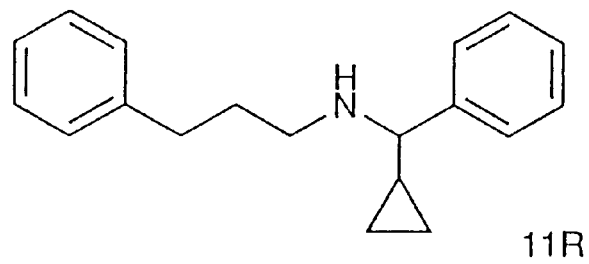
11R
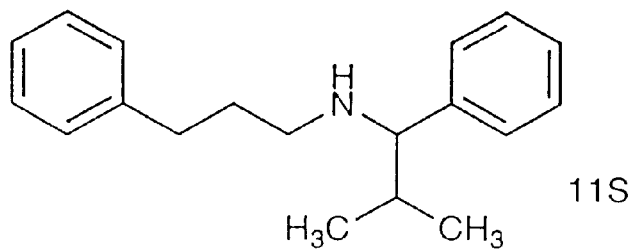
11S
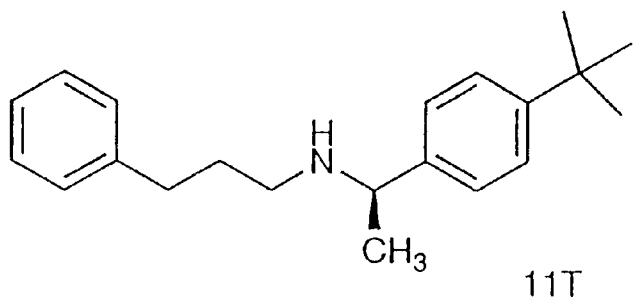
11T
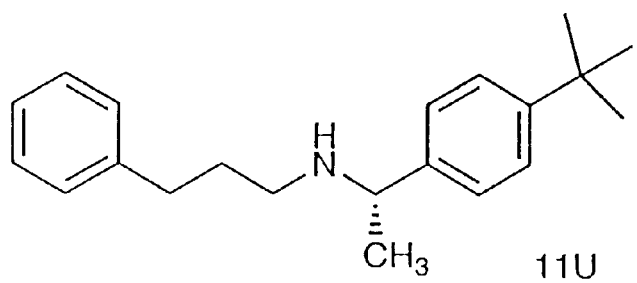
11U
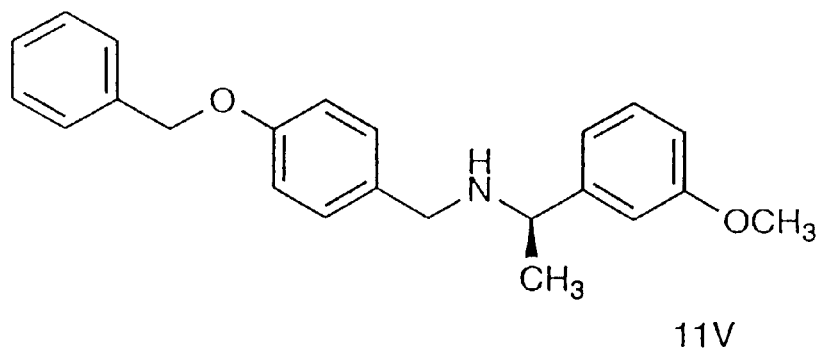
11V
*Fig. 1-52*

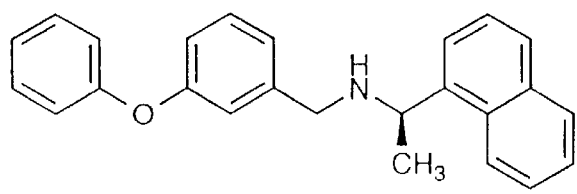
12A
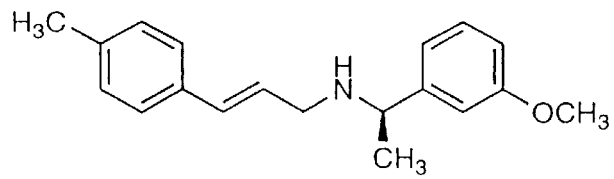
12B
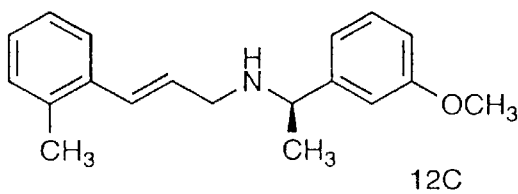
12C
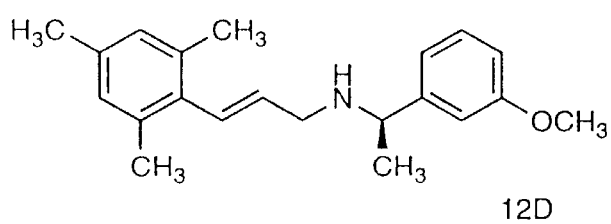
12D
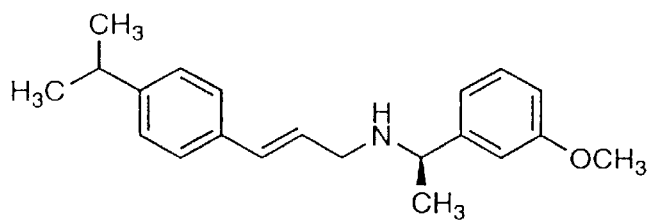
12E
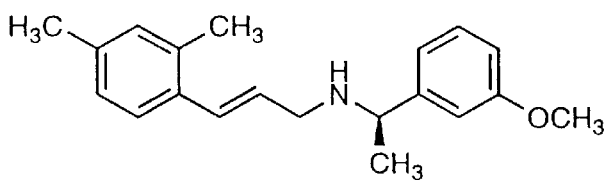
12F
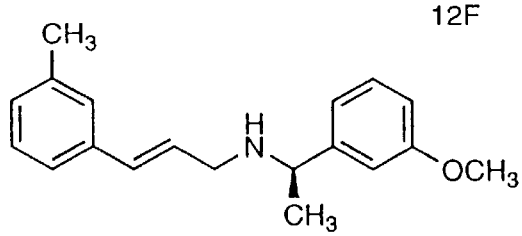
12G
*Fig. 1-54*

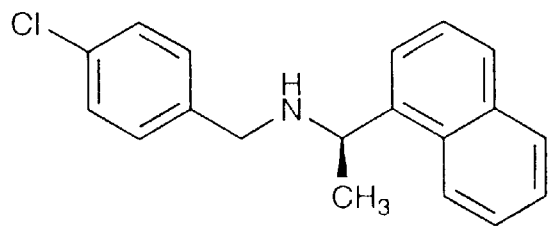
13O
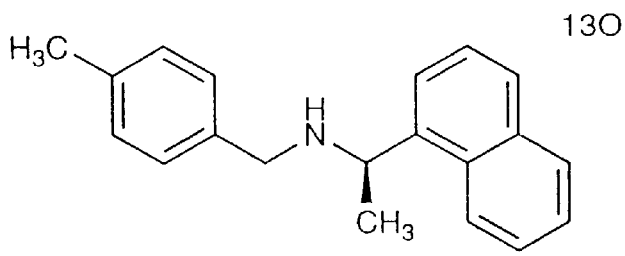
13P
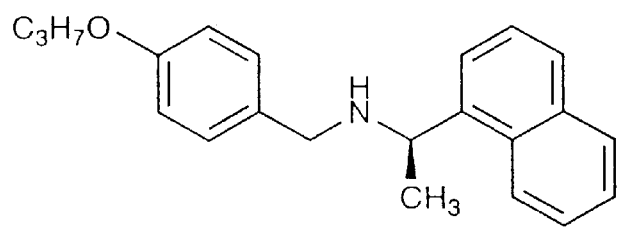
13Q
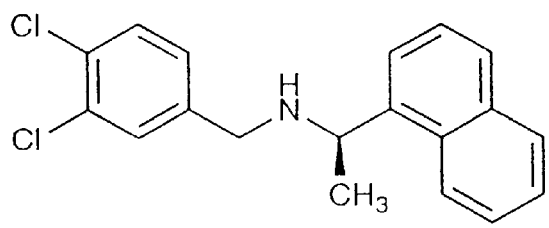
13R
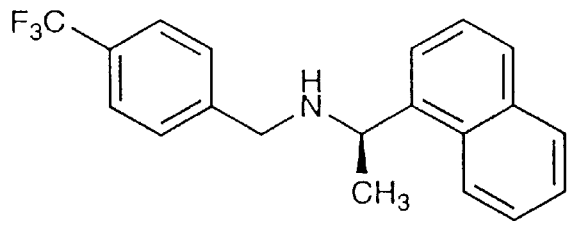
13S
Fig. 1-60
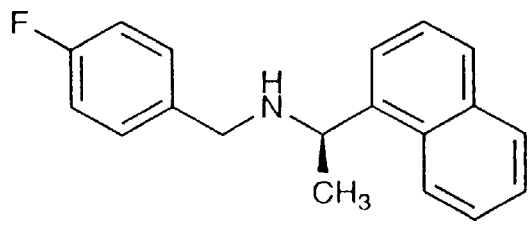
13T

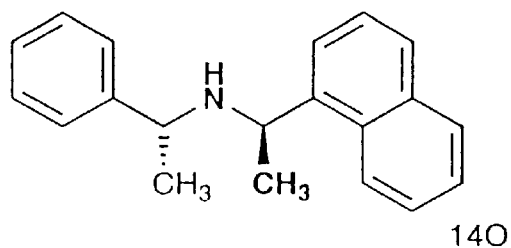
14O
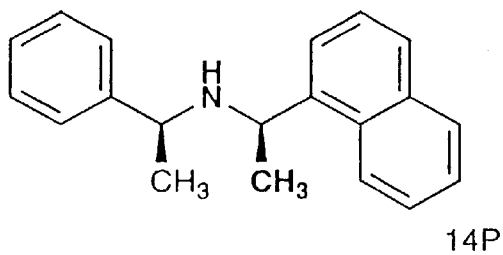
14P
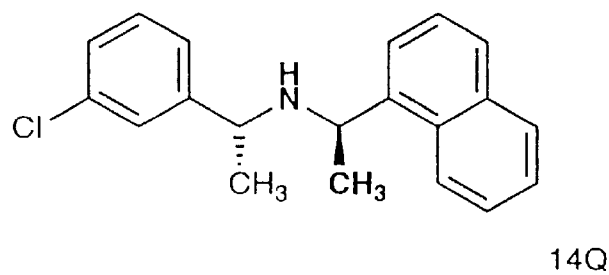
14Q
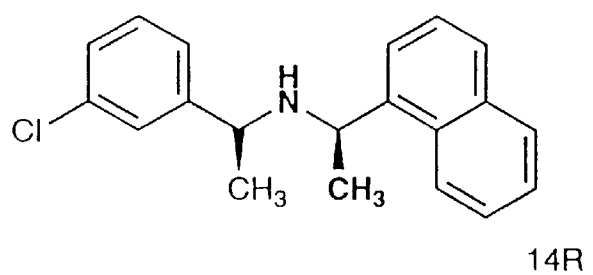
14R
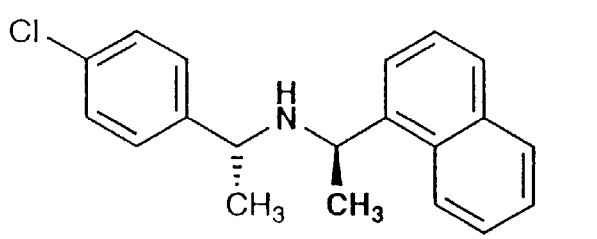
14S
*Fig. 1-64*
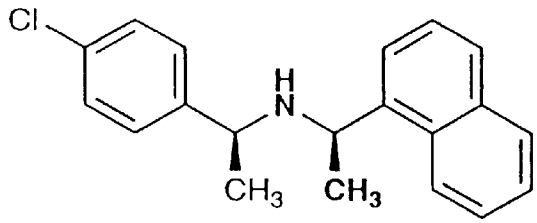
14T

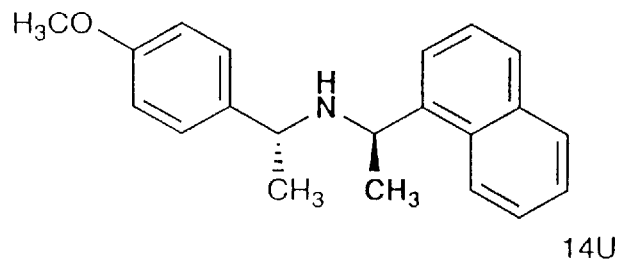
14U
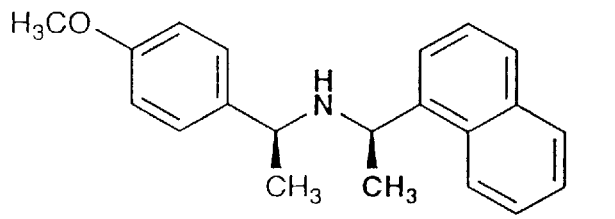
14V
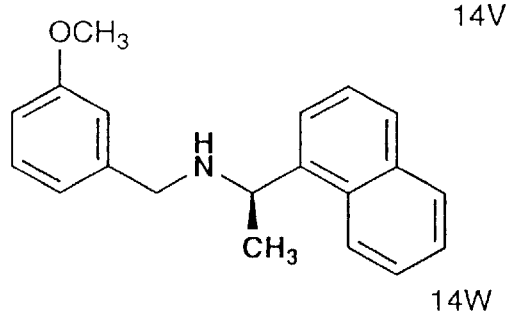
14W
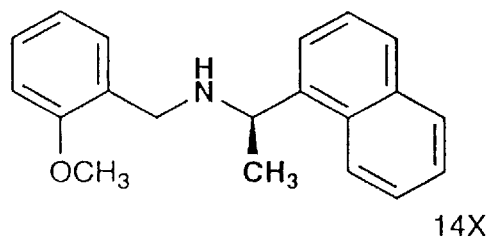
14X
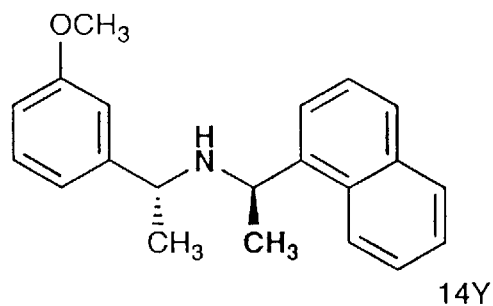
14Y
*Fig. 1-65*
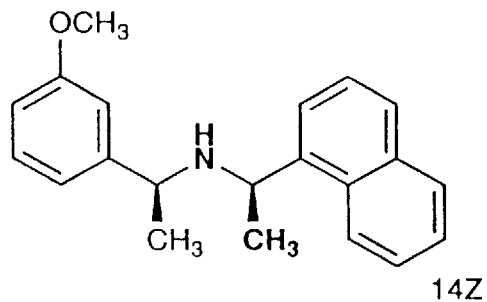
14Z

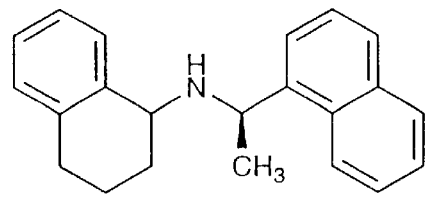
15A
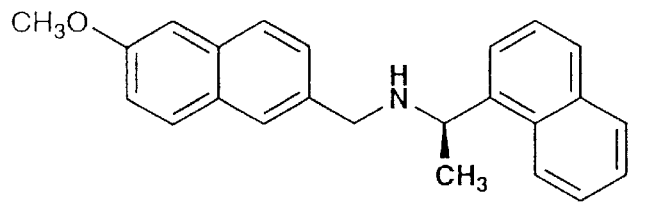
15B
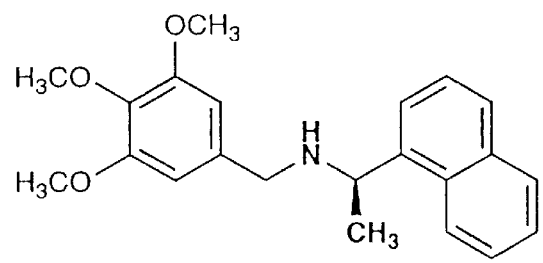
15C
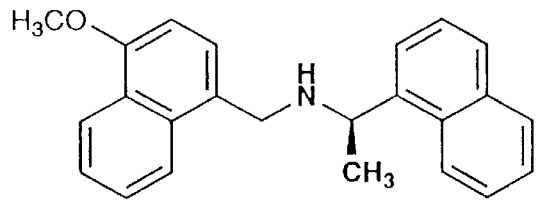
15D
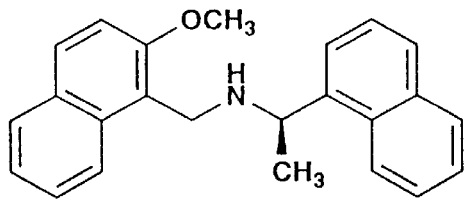
15E
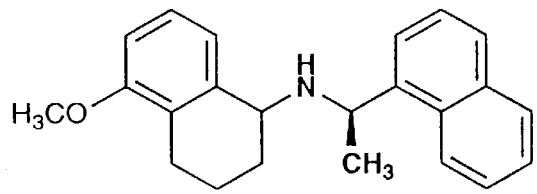
15F
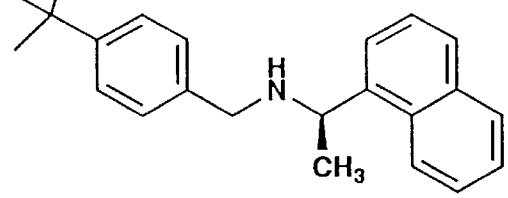
15G
Fig. 1-66

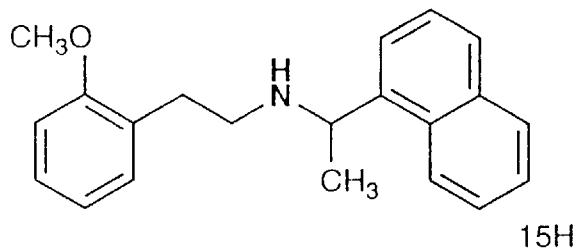
15H
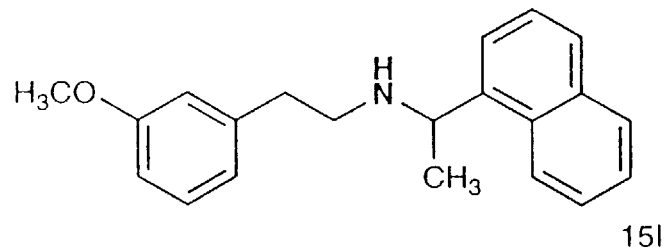
15I
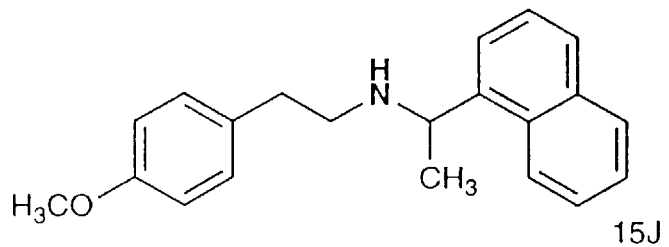
15J
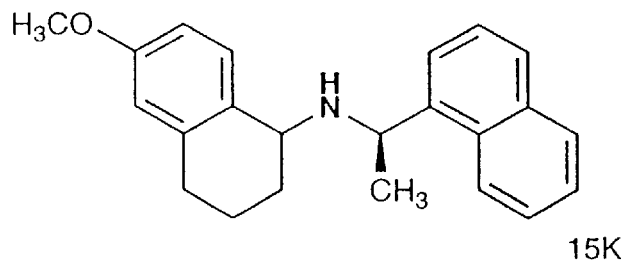
15K
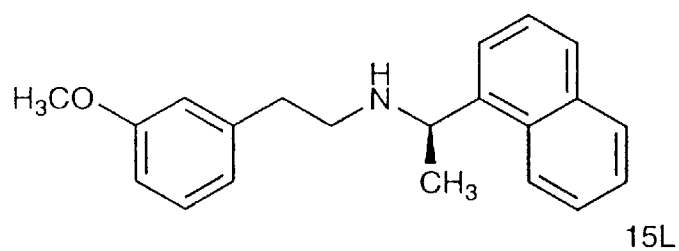
15L
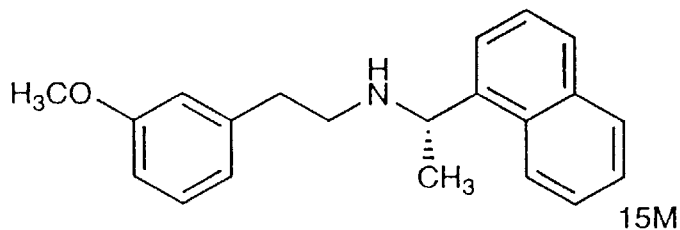
15M
*Fig. 1-67*

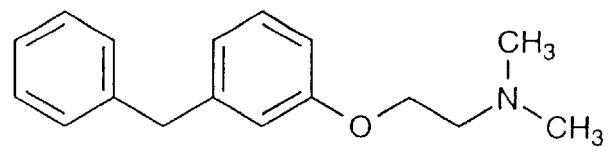
15T
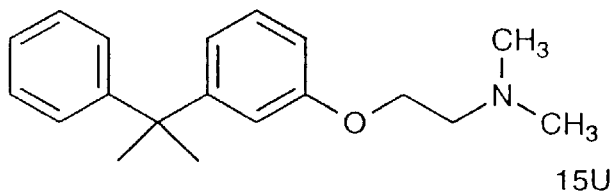
15U
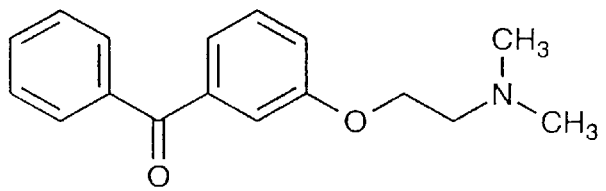
15V
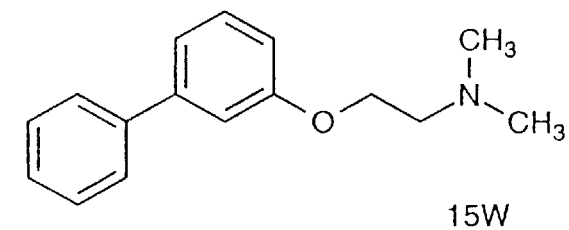
15W
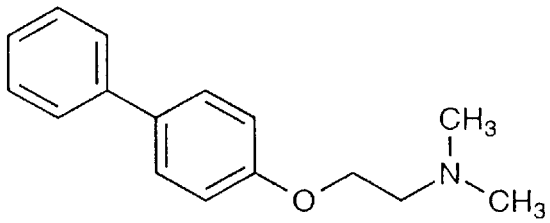
15X
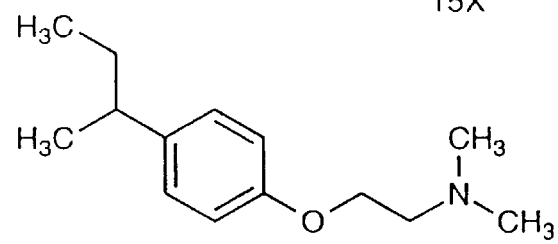
15Y
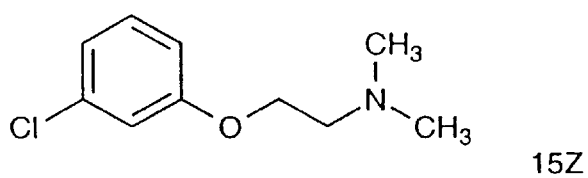
15Z
Fig. 1-69

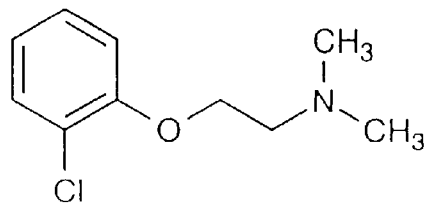
16A
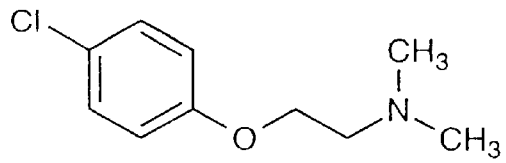
16B
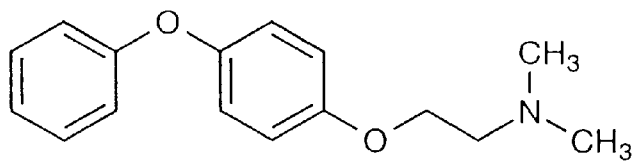
16C
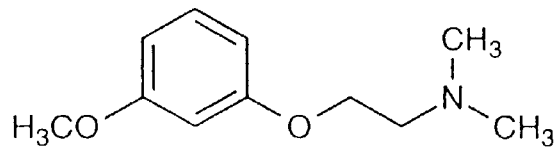
16D
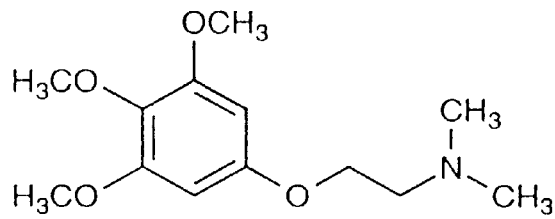
16E
*Fig. 1-70*
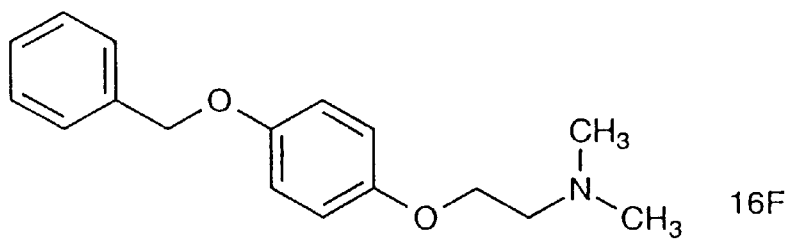
16F
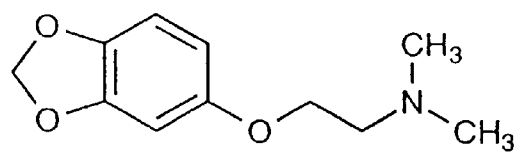

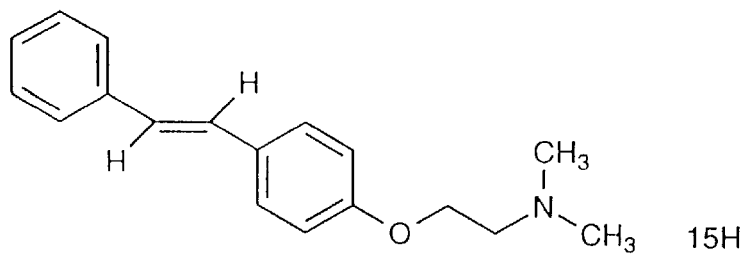
15H
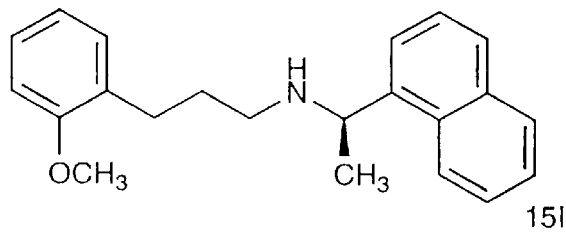
15I
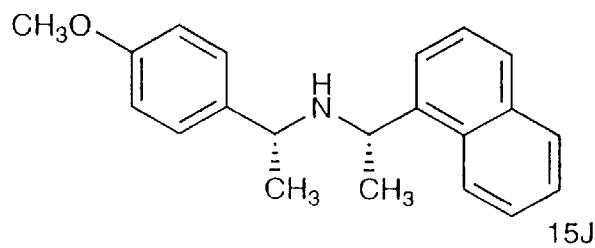
15J
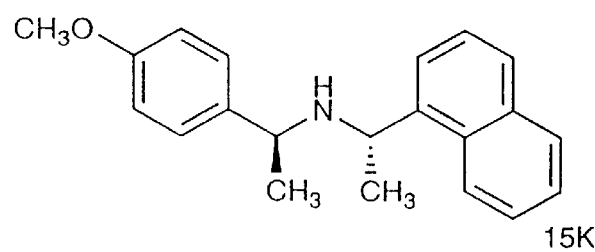
15K
*Fig. 1-71*
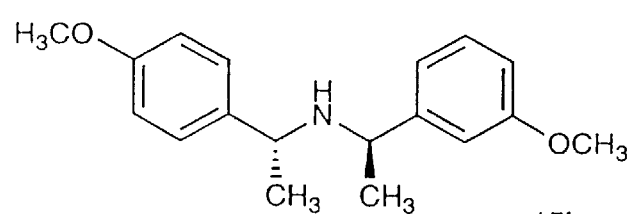
15L
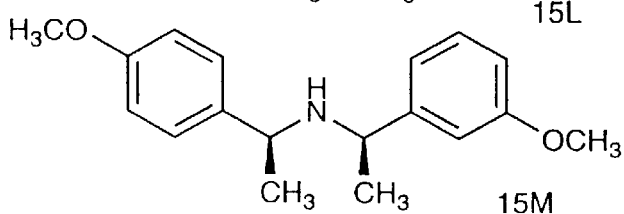
15M
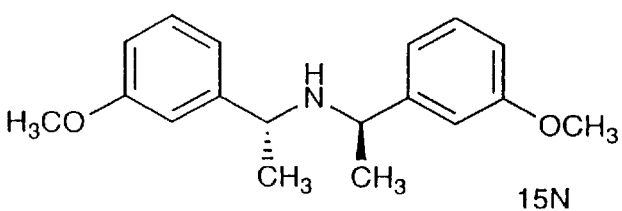
15N

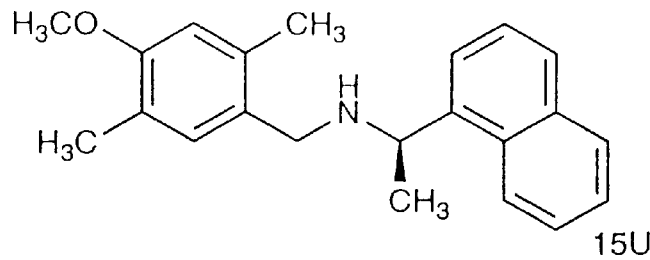
15U
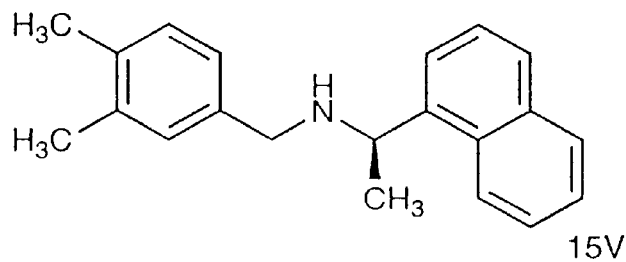
15V
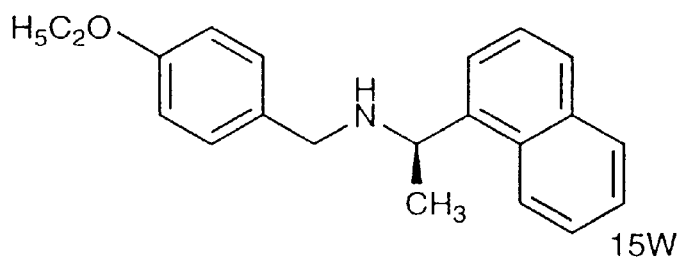
15W
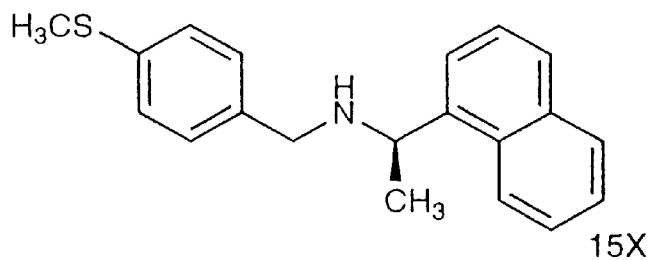
15X
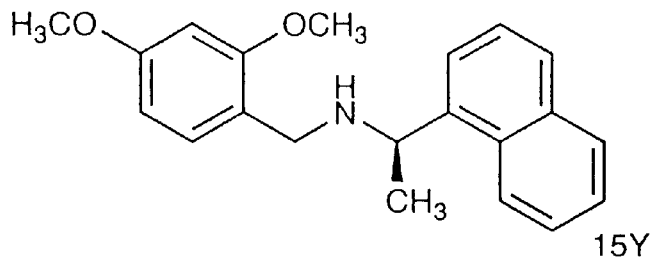
15Y
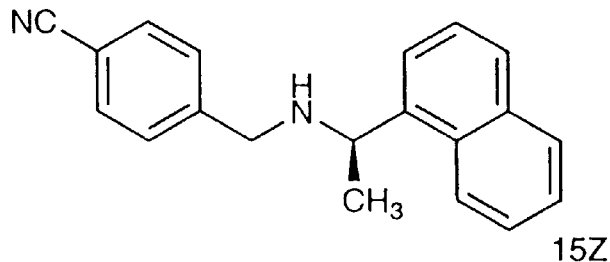
15Z
*Fig. 1-73*

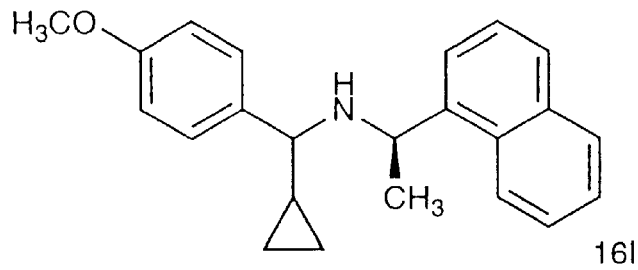
16I
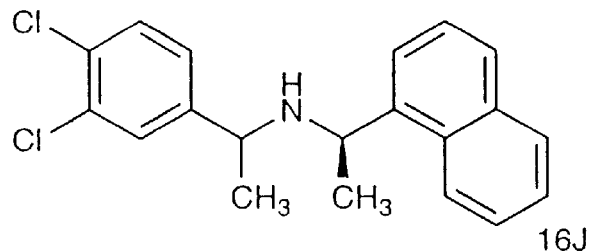
16J
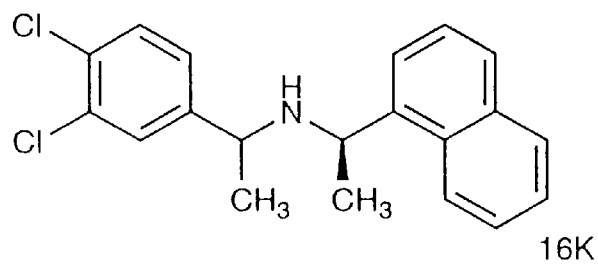
16K
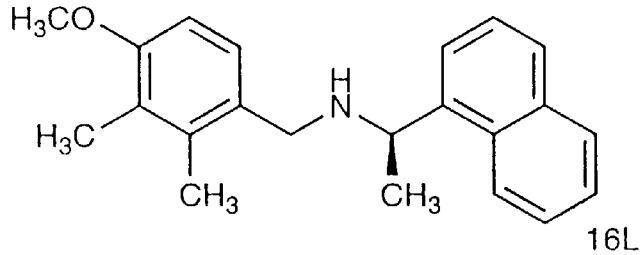
16L
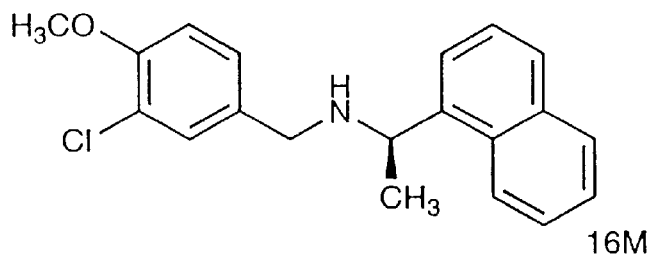
16M
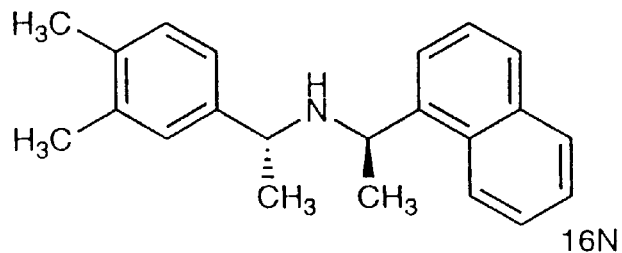
16N
*Fig. 1-75*

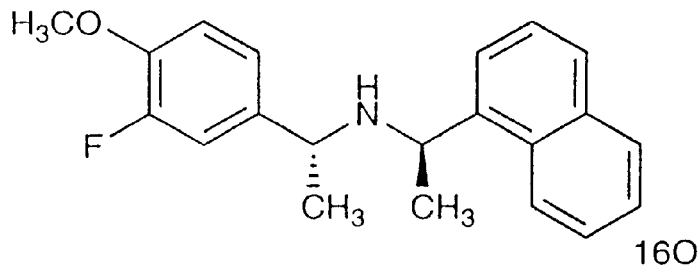
16O
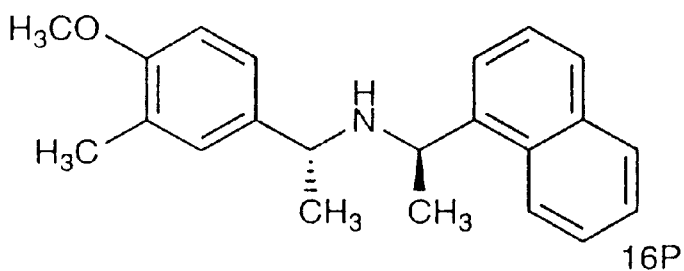
16P
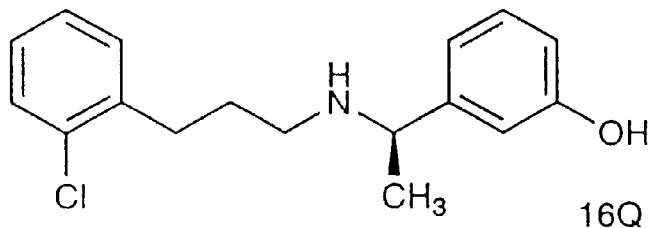
16Q
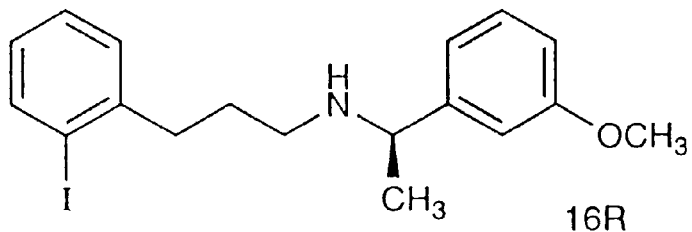
16R
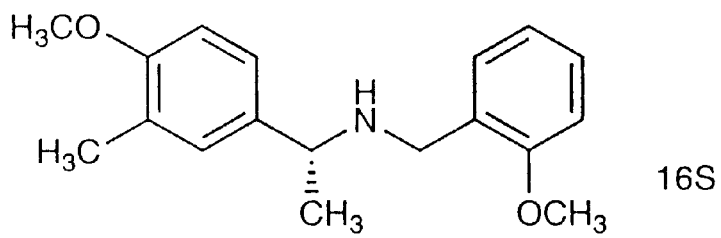
16S
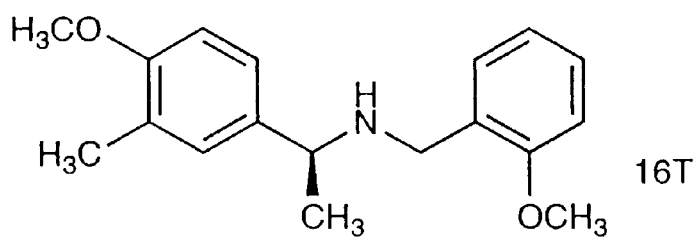
16T
Fig. 1-76

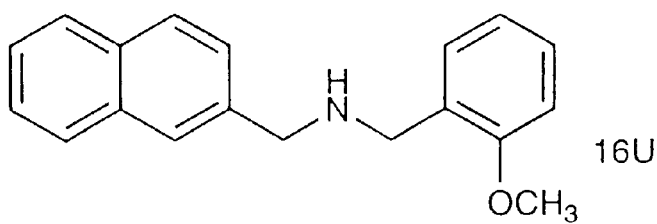
16U
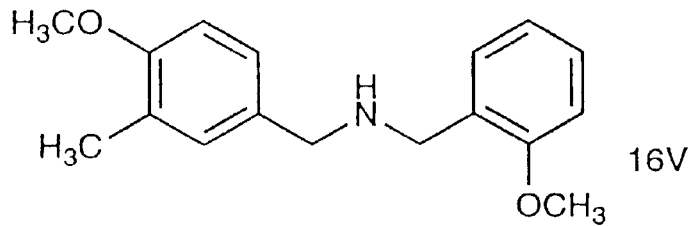
16V
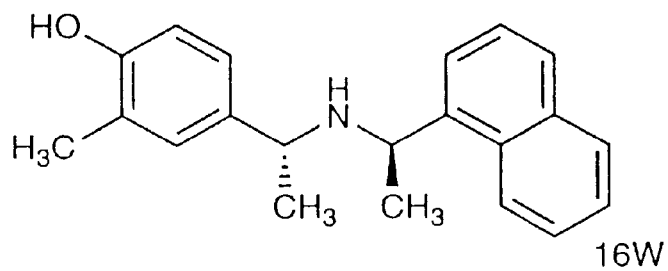
16W
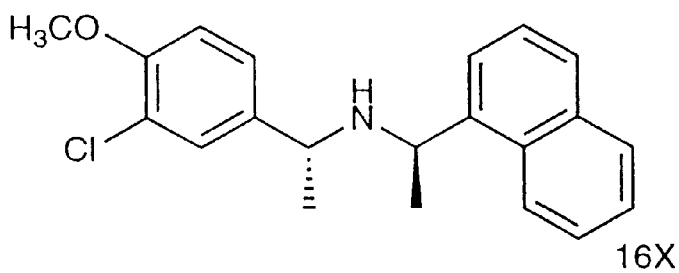
16X
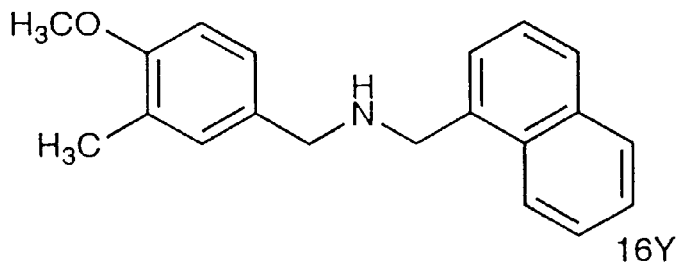
16Y
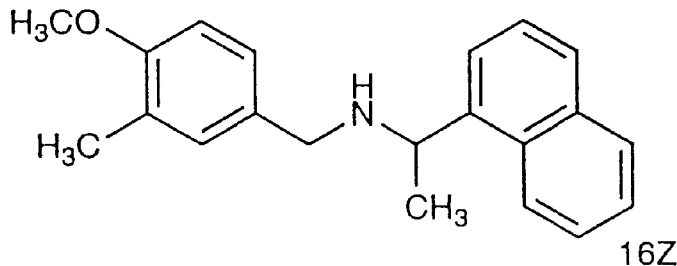
16Z
*Fig. 1-77*

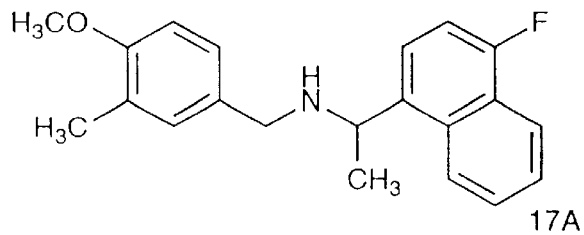
17A
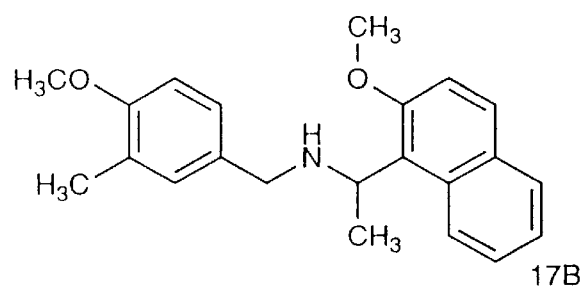
17B
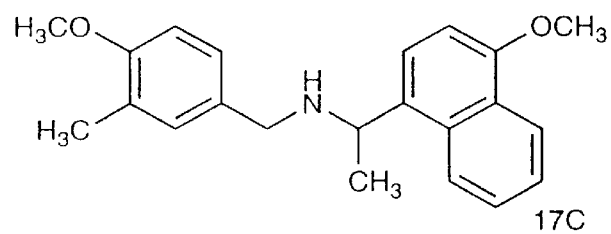
17C
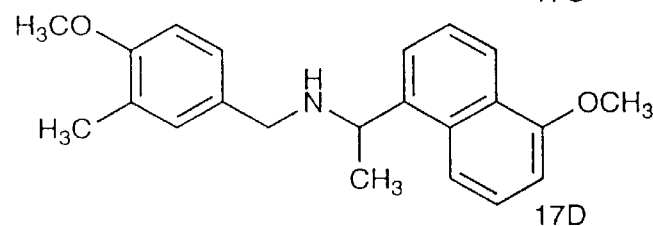
17D
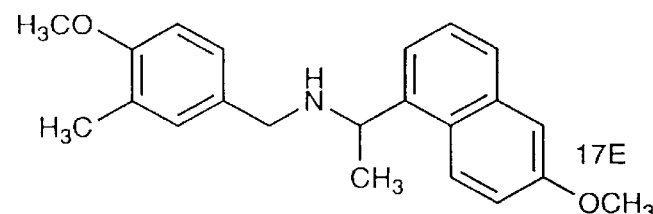
17E
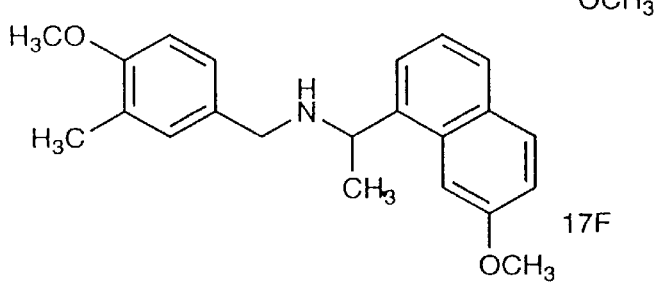
17F
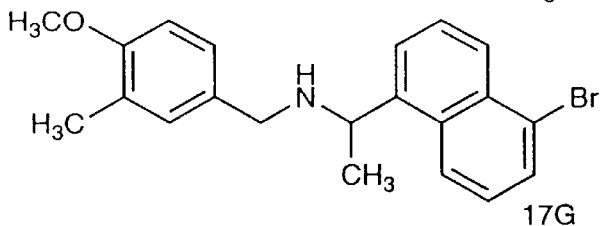
17G
Fig. 1-78

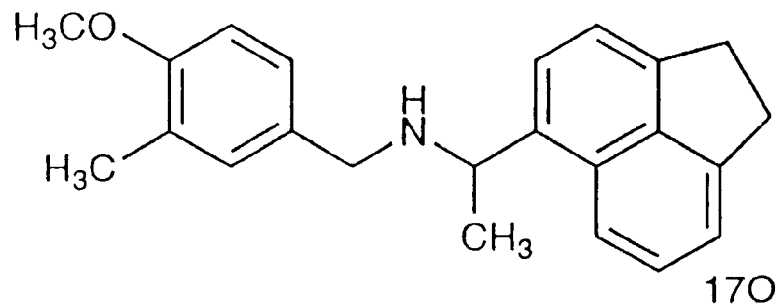
17O
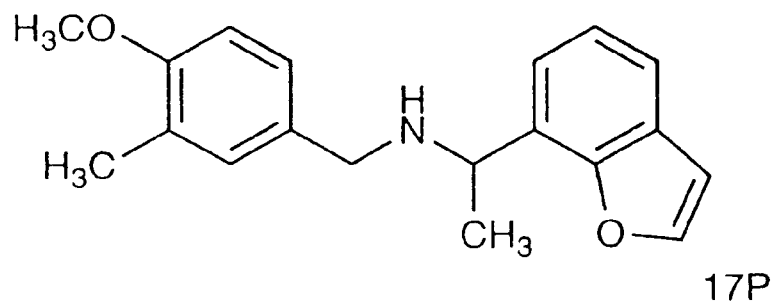
17P
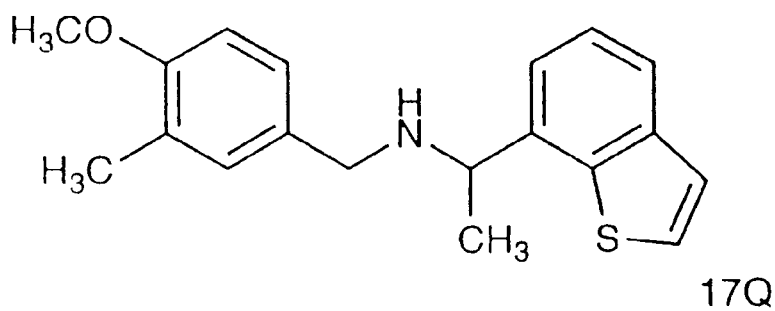
17Q
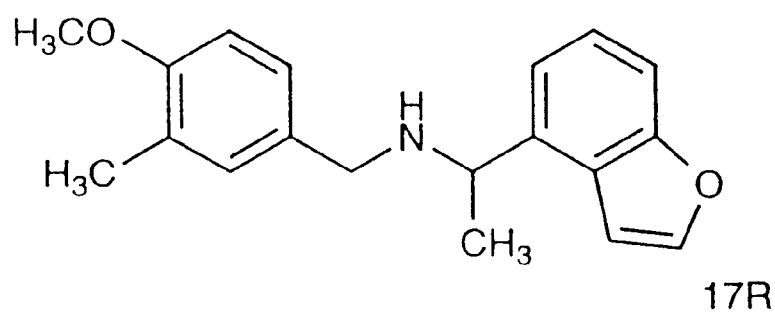
17R
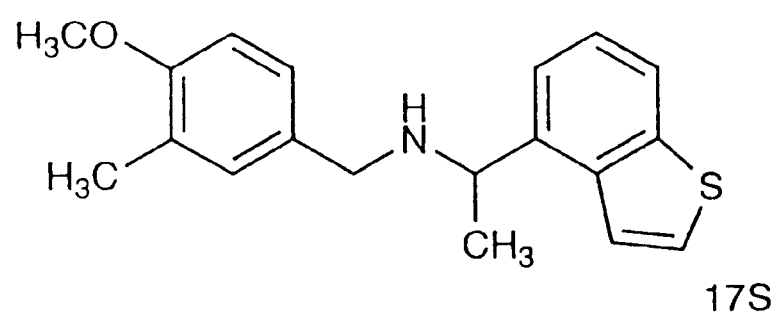
17S
*Fig. 1-80*

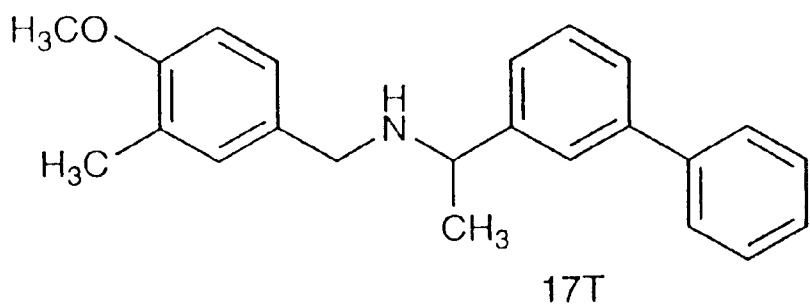
17T
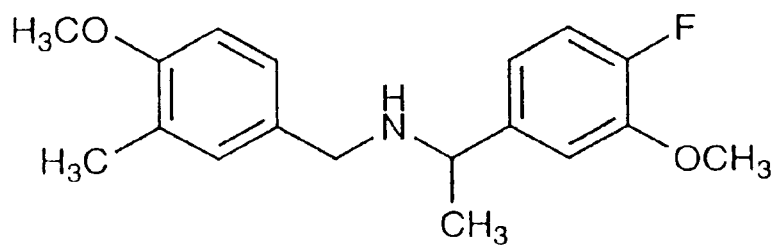
17U
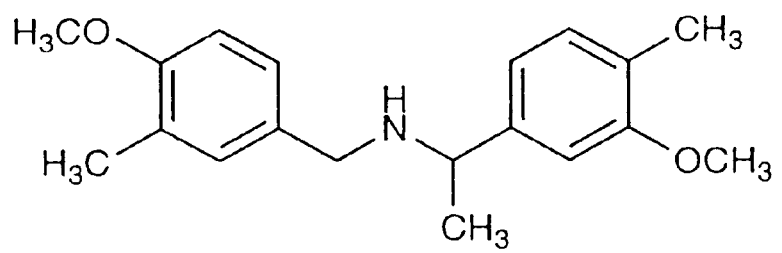
17V
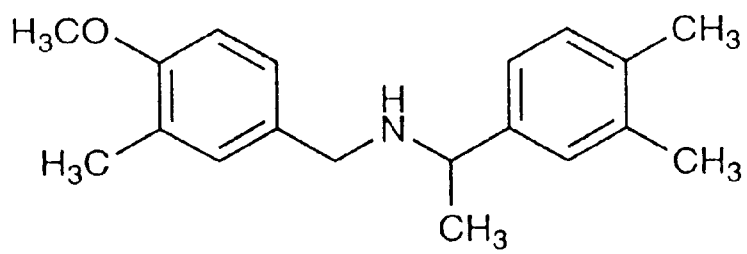
17W
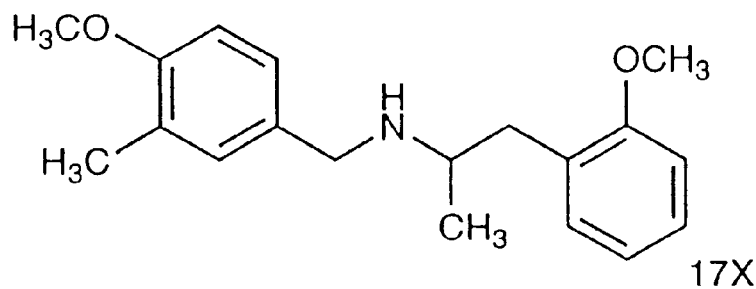
17X
Fig. 1-81

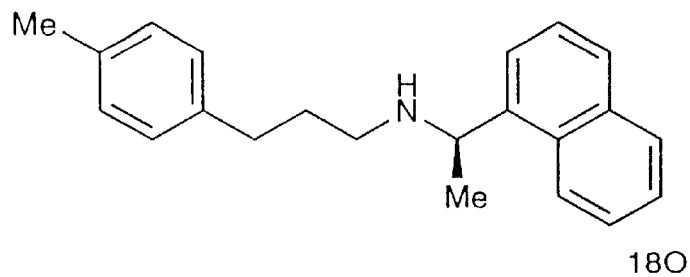
18O
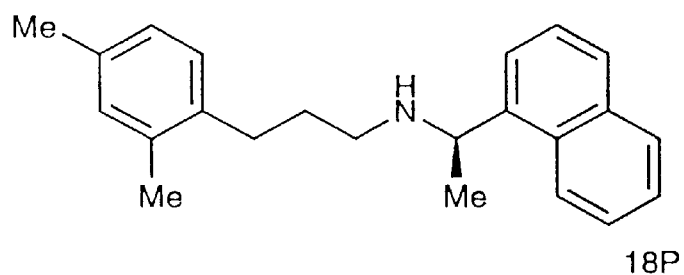
18P
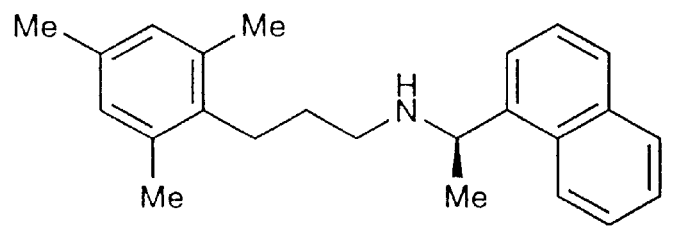
18Q
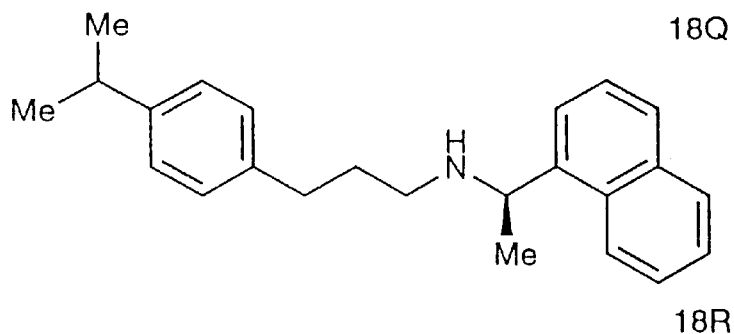
18R
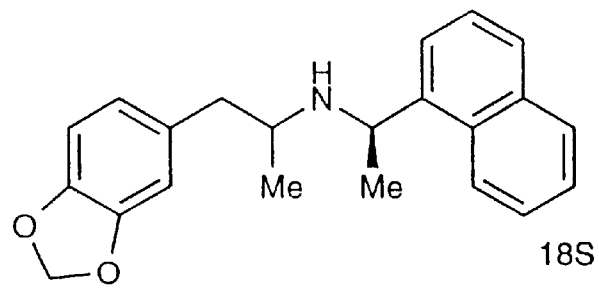
18S
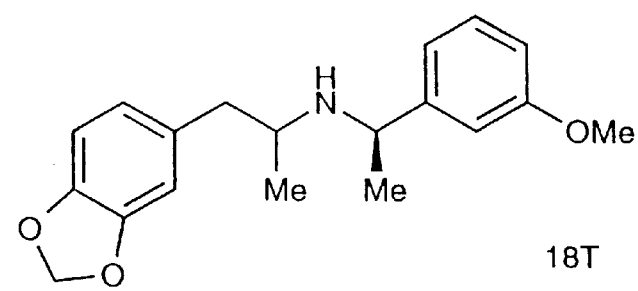
18T
Fig. 1-85

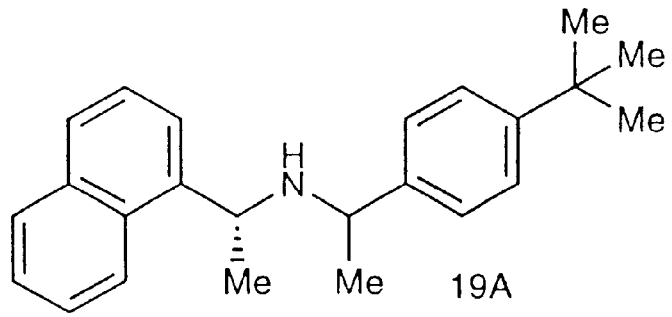
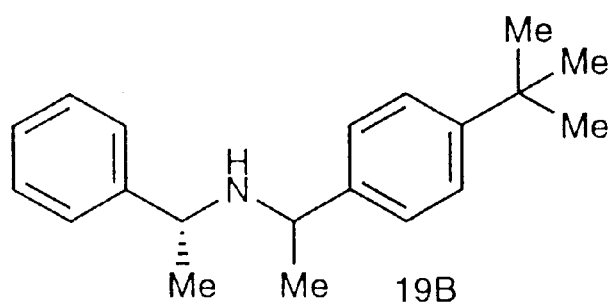
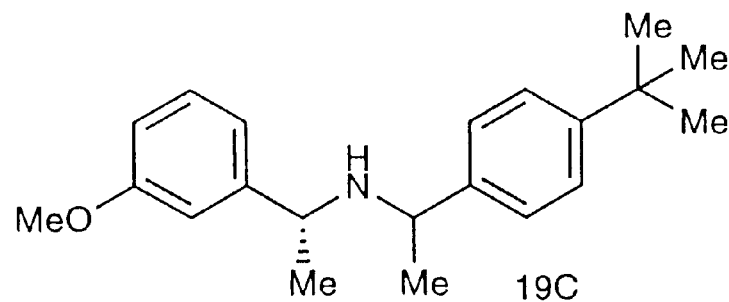
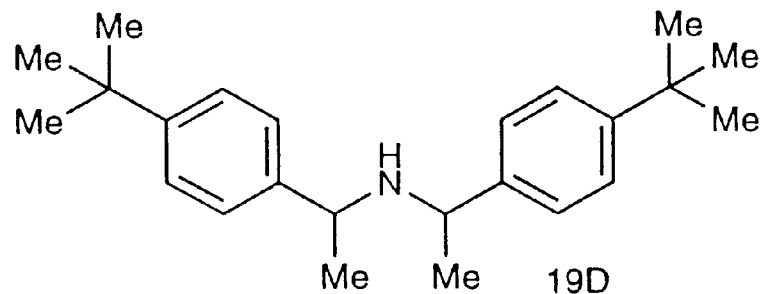
*Fig. 1-87*

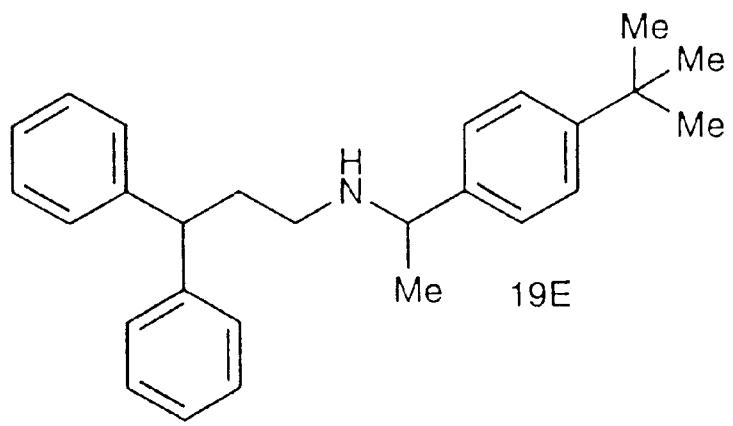
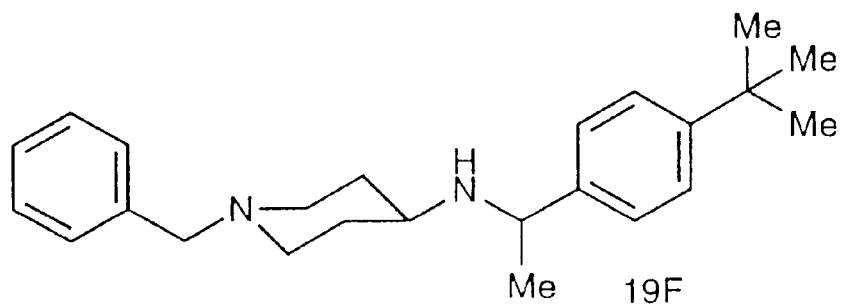
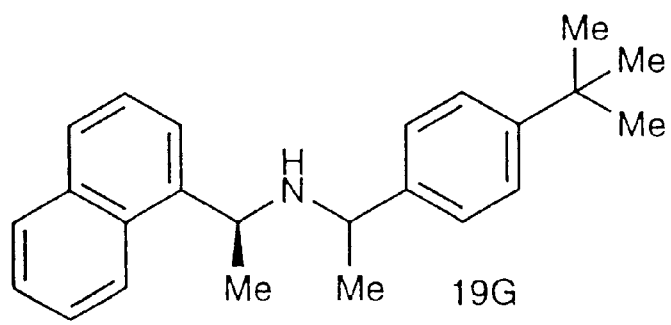
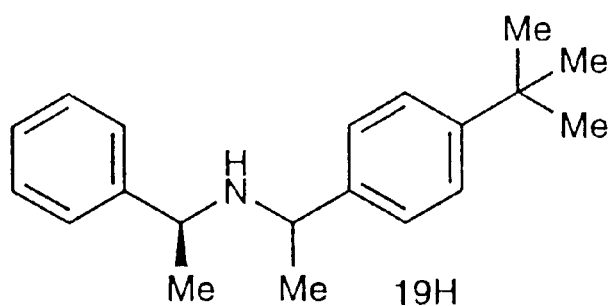
*Fig. 1-88*

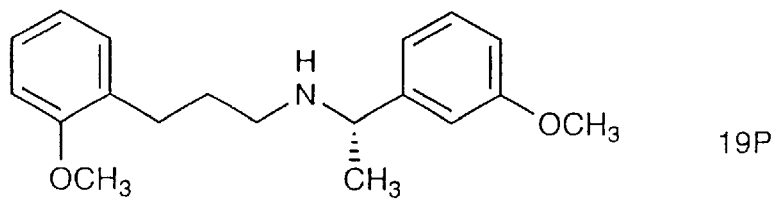
19P
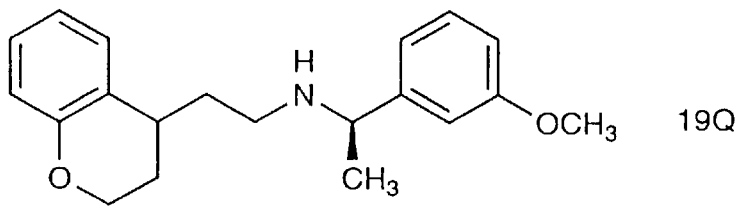
19Q
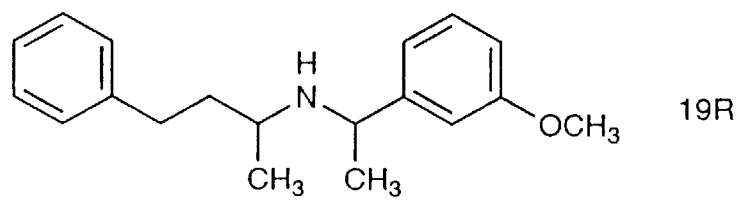
19R
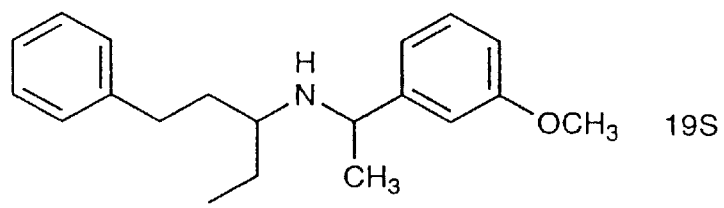
19S
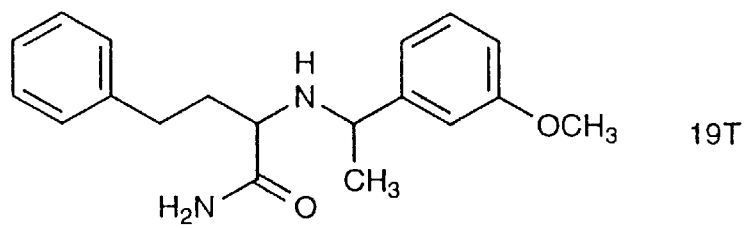
19T
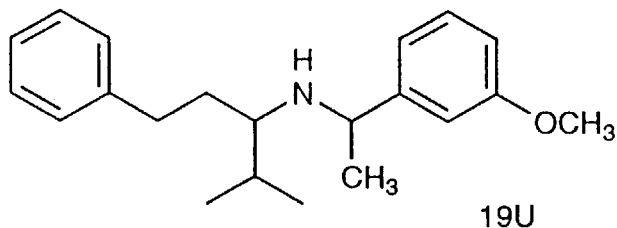
19U
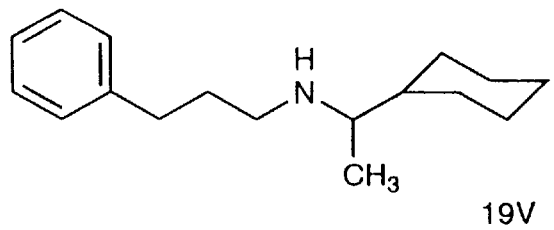
19V
*Fig. 1-90*

CALCIUM RECEPTOR-ACTIVE MOLECULES

This application is a continuation-in-part of U.S. Ser. No. 08/353,784, filed Dec. 8, 1994, which is a continuation-in-part of PCT/US94/12177 filed Oct. 21, 1994, and a continuation-in-part of U.S. Ser. No. 08/292,827, filed Aug. 19, 1994, abandoned, and a continuation-in-part of U.S. Ser. No. 08/141,248, filed Oct. 22, 1993, abandoned, and a continuation-in-part of U.S. Ser. No. 08/009,389, filed Feb. 23, 1993, abandoned, U.S. Ser. No. 08/009,389 is a continuation-in-part of U.S. Ser. No. 08/017,127, filed Feb. 12, 1993, abandoned, which is a continuation-in-part of U.S. Ser. No. 07/934,161, filed Aug. 21, 1992, abandoned, which is a continuation-in-part of U.S. Ser. No. 07/834,044 filed Feb. 11, 1992, abandoned, which is a continuation-in-part of U.S. Ser. No. 07/749,451 filed Aug. 23, 1991, abandoned, the whole of each of these applications including the drawings are hereby incorporated by reference herein.

FIELD OF THE INVENTION

This invention relates to the design, development, composition and use of novel molecules able to modulate the activity of inorganic ion receptor.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "[$Ca^{2+}$]") alter the functional responses of these cells. One such specialized cell is the parathyroid cell which secretes parathyroid hormone (PTH). PTH is the principal endocrine factor regulating $Ca^{2+}$ homeostasis in the blood and extracellular fluids.

PTH, by acting on bone and kidney cells, increases the level of $Ca^{2+}$ in the blood. This increase in [$Ca^{2+}$] then acts as a negative feedback signal, depressing PTH secretion. The reciprocal relationship between [$Ca^{2+}$] and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in [$Ca^{2+}$] has been confirmed. Brown et al., 366 *Nature* 574, 1993. In parathyroid cells, this protein acts as a receptor for extracellular $Ca^{2+}$ ("the calcium receptor"), and detects changes in [$Ca^{2+}$] and to initiate a functional cellular response, PTH secretion.

Extracellular $Ca^{2+}$ can exert effects on different cell functions, reviewed in Nemeth et al., 11 *Cell Calcium* 319, 1990. The role of extracellular $Ca^{2+}$ in parafollicular (C-cells) and parathyroid cells is discussed in Nemeth, 11 *Cell Calcium* 323, 1990. These cells have been shown to express similar $Ca^{2+}$ receptor. Brown et al., 366 *Nature* 574, 1993; Mithal et al., 9 Suppl. 1 *J. Bone and Mineral Res.* s282, 1994; Rogers et al., 9 Suppl. 1 *J. Bone and Mineral Res.* s409, 1994; Garrett et al., 9 Suppl. 1 *J. Bone and Mineral Res.* s409, 1994. The role of extracellular $Ca^{2+}$ on bone osteoclasts is discussed by Zaidi, 10 *Bioscience Reports* 493, 1990. In addition keratinocytes, juxtaglomerular cells, trophoblasts, pancreatic beta cells and fat/adipose cells all respond to increases in extracellular calcium which likely reflects activation of calcium receptors of these cells.

The ability of various compounds to mimic extra-cellular $Ca^{2+}$ in vitro is discussed by Nemeth et al., (spermine and spermidine) in "Calcium-Binding Proteins in Health and Disease," 1987, Academic Press, Inc., pp. 33–35; Brown et al., (e.g., neomycin) 128 *Endocrinology* 3047, 1991; Chen et al., (diltiazem and its analog, TA-3090) 5 *J. Bone and Mineral Res.* 581, 1990; and Zaidi et al., (verapamil) 167 *Biochem. Biophys. Res. Commun.* 807, 1990. Nemeth et al., PCT/US93/01642, International Publication Number WO 94/18959, and Nemeth et al., PCT/US92/07175, International Publication Number WO 93/04373, describe various compounds which can modulate the effect of an inorganic ion on a cell having an inorganic ion receptor, preferably modulate the effects of calcium on a calcium receptor.

The references provided in the background are not admitted to be prior art.

SUMMARY OF THE INVENTION

The present invention features molecules which can modulate one or activities of an inorganic ion receptor. Preferably, the molecule can mimic or block the effect of extracellular $Ca^{2+}$ on a calcium receptor. The preferred use of such molecules is to treat diseases or disorders by altering inorganic ion receptor activity, preferably calcium receptor activity.

Extracellular $Ca^{2+}$ is under tight homeostatic control and controls various processes such as blood clotting, nerve and muscle excitability, and proper bone formation. Calcium receptor proteins enable certain specialized cells to respond to changes in extracellular $Ca^{2+}$ concentration. For example, extracellular $Ca^{2+}$ inhibits the secretion of parathyroid hormone from parathyroid cells, inhibits bone resorption by osteoclasts, and stimulates secretion of calcitonin from C-cells.

Compounds modulating inorganic ion receptor activity can be used to treat diseases or disorders by affecting one or more activities of an inorganic ion receptor resulting in a beneficial effect to the patient. For example, osteoporosis is an age related disorder characterized by loss of bone mass and increased risk of bone fracture. Compounds blocking osteoclastic bone resorption either directly (e.g., a osteoclast ionmimetic compound) or indirectly by increasing endogenous calcitonin levels (e.g., a C-cell ionmimetic), and/or by decreasing parathyroid hormone levels (e.g., a parathyroid cell ionmimetic) can retard bone loss and, thus, result in beneficial effects to patients suffering from osteoporosis.

In addition, it is known that intermittent low dosing with PTH results in an anabolic effect on bone mass and appropriate bone remodeling. Thus, compounds and dosing regiments evoking transient increases in parathyroid hormone (e.g., intermittent dosing with a parathyroid cell ionlytic) can increase bone mass in patients suffering from osteoporosis.

Additionally, diseases or disorders characterized by a defect in one or more inorganic ion receptor activities may be treated by the present invention. For example, certain forms of primary hyperparathyroidism are characterized by abnormally high levels of parathyroid hormone and decreased parathyroid gland responsiveness to circulating calcium. Calcium receptor modulating agents can be used to modulate parathyroid cell responsiveness to calcium.

Preferably, the compound modulates calcium receptor activity and is used in the treatment of diseases or disorders which can be affected by modulating one or more activities of a calcium receptor. Preferably, the disease or disorder is characterized by abnormal bone and mineral homeostasis, more preferably calcium homeostasis.

Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; and (5) an abnormal increase or decrease in the production and/or release of circulating messengers or hormones which affect calcium homeostasis such as parathyroid hormone and calcitonin. The abnormal increase or decrease in these different aspects of calcium homeostasis is relative to that occurring in the general population and is generally associated with a disease or disorder.

More generally, a molecule which modulates the activity of an inorganic ion receptor is useful in the treatment of diseases characterized by abnormal inorganic ion homeostasis. Preferably, the molecule modulates one or more effects of an inorganic ion receptor. Inorganic ion receptor modulating agents include ionmimetics, ionlytics, calcimimetics, and calcilytics.

Ionmimetics are molecules which mimic the effects of increasing ion concentration at an inorganic ion receptor. Preferably, the molecule affects one or more calcium receptor activities. Calcimimetics are ionmimetics which affect one or more calcium receptor activities and preferably binds to a calcium receptor.

Ionlytics are molecules which reduce or block one or more activities caused by an inorganic ion on an inorganic ion receptor. Preferably, the molecule inhibits one or more calcium receptor activities. Calcilytics are ionlytics which inhibit one or more calcium receptor activities evoked by extracellular calcium and preferably bind to a calcium receptor.

Inorganic ion receptor modulating agents can be formulated as pharmacological agents or compositions to facilitate administration in a patient. Pharmacological agents or compositions are agents or compositions in a form suitable for administration into a mammal, preferably a human. Considerations concerning forms suitable for administration are known in the art and include toxic effects, solubility, route of administration, and maintaining activity.

Thus, a first aspect the invention features an inorganic ion receptor modulating agent comprising a molecule which either evokes one or more inorganic ion receptor activities, or blocks one or more inorganic ion receptor activity caused by an extracellular inorganic ion. The molecule has the formula:

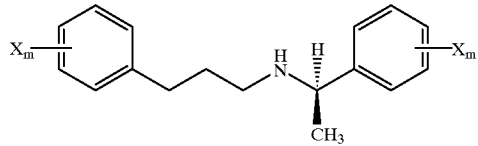

where each X is independently selected from the group consisting of isopropyl, CH$_3$O, CH$_3$S, CF$_3$O, an aliphatic ring and an attached or fused aromatic ring; and each m is independently between 0 and 5 inclusive.

Preferably, the aromatic and aliphatic rings have 5 to 7 members. More preferably, the aromatic and aliphatic rings contain only carbon atoms (i.e., the ring is not a heterocyclic ring).

Preferably, the molecule either evokes one or more calcium receptor activities, or blocks one or more calcium receptor activities caused by extracellular calcium.

Another aspect of the present invention features an inorganic ion receptor modulating agent having the formula:

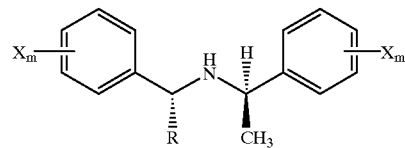

where each X independently is selected from the group consisting of H, CH$_3$, CH$_3$O, CH$_3$CH$_2$O, methylene dioxy, Br, Cl, F, CF$_3$, CHF$_2$, CH$_2$F, CF$_3$O, CH$_3$S, OH, CH$_2$OH, CONH$_2$, CN, NO$_2$, CH$_3$CH$_2$, propyl, isopropyl, butyl, isobutyl, t-butyl, acetoxy, aliphatic ring and an attached or fused aromatic ring;

each R independently is selected from the group consisting of hydrogen, methyl, ethyl, propyl, isopropyl, butyl, allyl, isobutyl, t-butyl, cyclopentyl, cyclohexyl, cycloheptyl, cyclooctyl, indenyl, indanyl, dihydroindolyl, thiodihydroindolyl, and 2-, 3-, or 4-piperid(in)yl; and each m is independently between 0 and 5 inclusive.

The molecule either evokes one or more inorganic ion receptor activities, or blocks one or more inorganic ion receptor activities caused by an extracellular inorganic ion. Preferably, the molecule either evokes one or more calcium receptor activities, or blocks one or more calcium receptor activities caused by extracellular calcium.

In preferred embodiments R is either H, CH$_3$, ethyl, or isopropyl, and each X is independently selected from the group consisting of isopropyl, CH$_3$O, CH$_3$S, CF$_3$O, aliphatic ring and an attached or fused aromatic ring. Preferably, the aliphatic ring and attached or fused aromatic ring have 5 to 7 members. More preferably, the aromatic and aliphatic rings contain only carbon atoms.

Another aspect of the present invention features an inorganic ion receptor modulating agent comprising a molecule selected from the group consisting of compound 4L, compound 8J, compound 8U, compound 9R, compound 11X, compound 12U, compound 12V, compound 12Z, compound 14U, compound 16M and compound 16P.

Other aspects of the present invention feature methods for using the agents described herein for treating diseases or disorders by modulating inorganic ion receptor activity. Patients in need of such treatments can be identified by standard medical techniques, such as routine blood analysis. For example, by detecting a deficiency of protein whose production or secretion is affected by changes in inorganic ion concentrations, or by detecting abnormal levels of inorganic ions or hormones which effect inorganic ion homeostasis.

Therapeutic methods involve administering to the patient a therapeutically effective amount of an inorganic ion receptor modulating agent. In preferred embodiments these methods are used to treat a disease or disorder characterized by abnormal inorganic ion homeostasis, more preferably a disease or disorder characterized by abnormal calcium homeostasis. Diseases and disorders characterized by abnormal calcium homeostasis include hyperparathyroidism, osteoporosis and other bone and mineral-related disorders, and the like (as described, e.g., in standard medical text books, such as "Harrison's Principles of Internal Medicine"). Such diseases and disorders are treated using calcium receptor modulating agents which mimic or block one or more of the effects of Ca$^{2+}$ and, thereby, directly or indirectly affect the levels of proteins or other molecules in the body of the patient.

By "therapeutically effective amount" is meant an amount of an agent which relieves to some extent one or more symptoms of the disease or disorder in the patient; or returns to normal either partially or completely one or more physiological or biochemical parameters associated with or causative of the disease or disorder.

In a preferred embodiment, the patient has a disease or disorder characterized by an abnormal level of one or more calcium receptor regulated components and the molecule is active on a calcium receptor of a cell selected from the group consisting of parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

More preferably, the cell is a parathyroid cell and the molecule reduces the level of parathyroid hormone in the serum of the patient, even more preferably the level is reduced to a degree sufficient to cause a decrease in plasma $Ca^{2+}$, most preferably the parathyroid hormone level is reduced to that present in a normal individual.

Thus, the present invention features agents and methods useful in the treatment of diseases and disorders by modulating inorganic ion receptor activity. For example, the molecules of the present invention can be used to target calcium receptors on different cell types that detect and respond to changes to external calcium. For example, molecules mimicking external calcium may be used to selectively depress secretion of parathyroid hormone from parathyroid cells, or depress bone resorption by osteoclasts, or stimulate secretion of calcitonin from C-cells. Such molecules can be used to treat diseases or disorders characterized by abnormal calcium homeostasis such as hyperparathyroidism and osteoporosis.

Other features and advantages of the invention will be apparent from the following description of the preferred embodiments thereof and from the claims.

BRIEF DESCRIPTION OF THE DRAWING

FIGS. 1-1—90, show the chemical structures of molecules derived from diphenylpropyl-α-phenethylamine illustrating a family of molecules which were prepared and screened to find the useful molecules of the invention.

DESCRIPTION OF THE PREFERRED EMBODIMENTS

Figure 1:
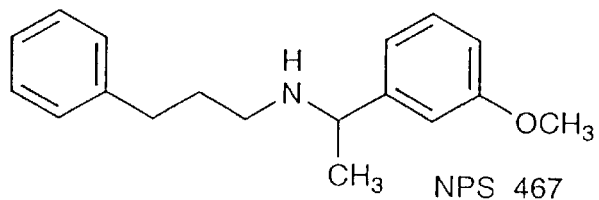
Figure 1:
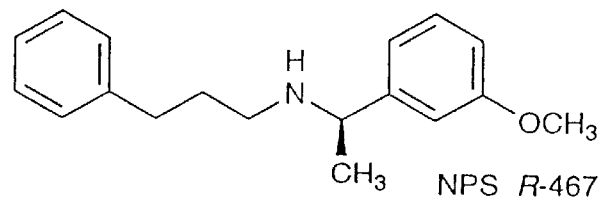
Figure 1:
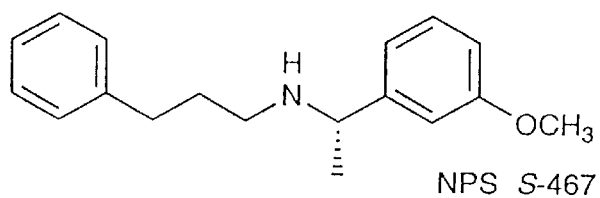
Figure 1:
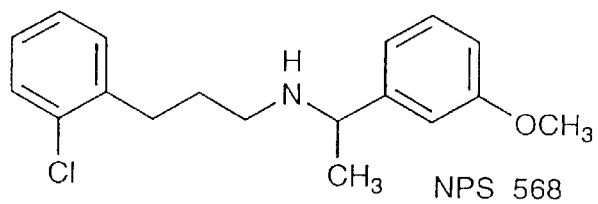
Figure 1:
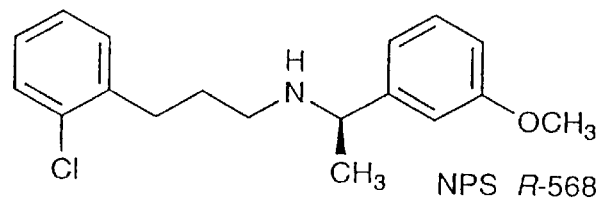
Figure 1:
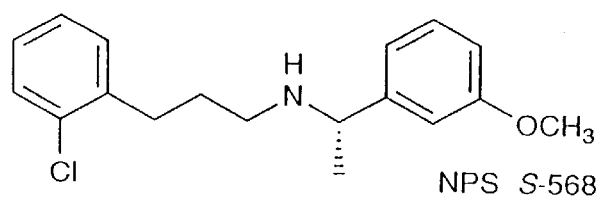
Figure 1:
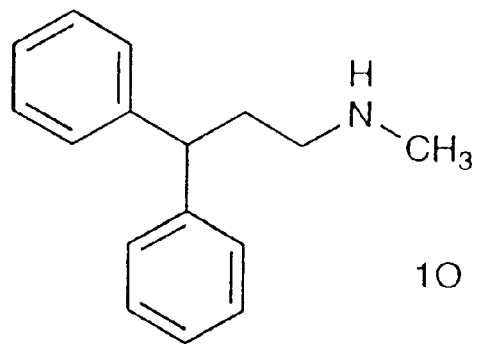
Figure 2:
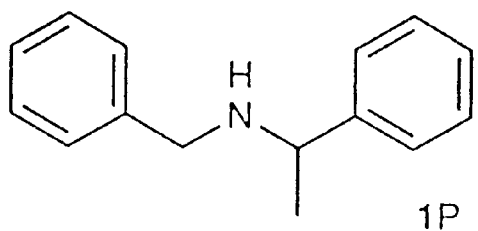
Figure 3:
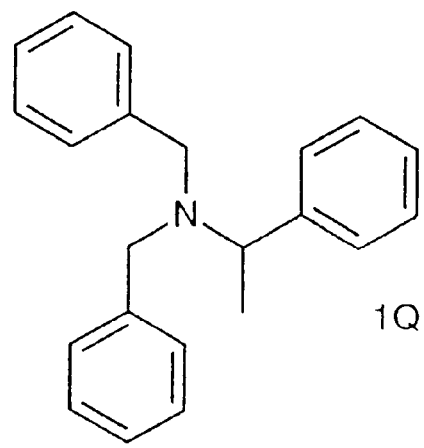
Figure 4:
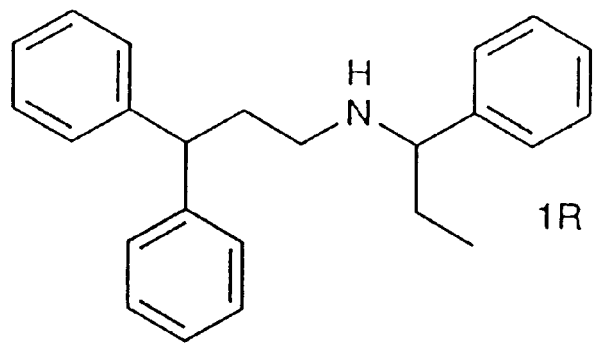
Figures 1, 2, 3, 4, 5, 6, 7:
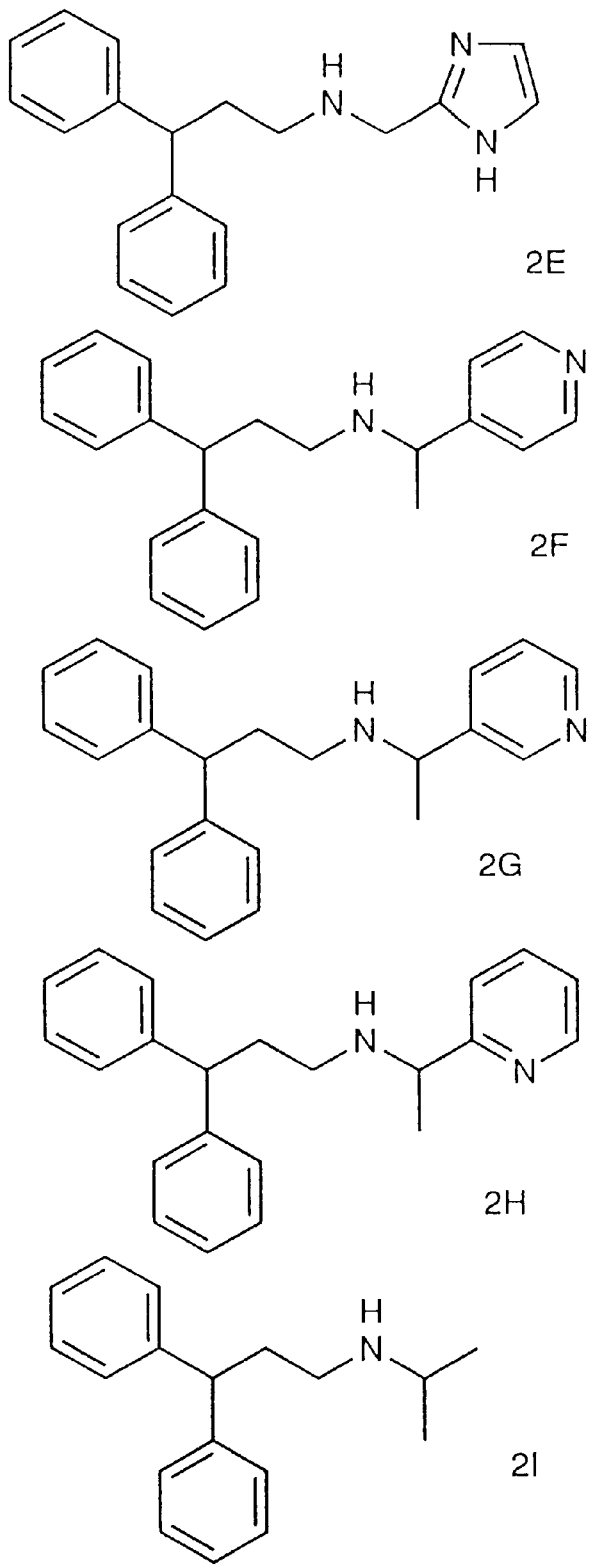
Figures 1, 2, 3, 4, 5, 6, 7, 8:
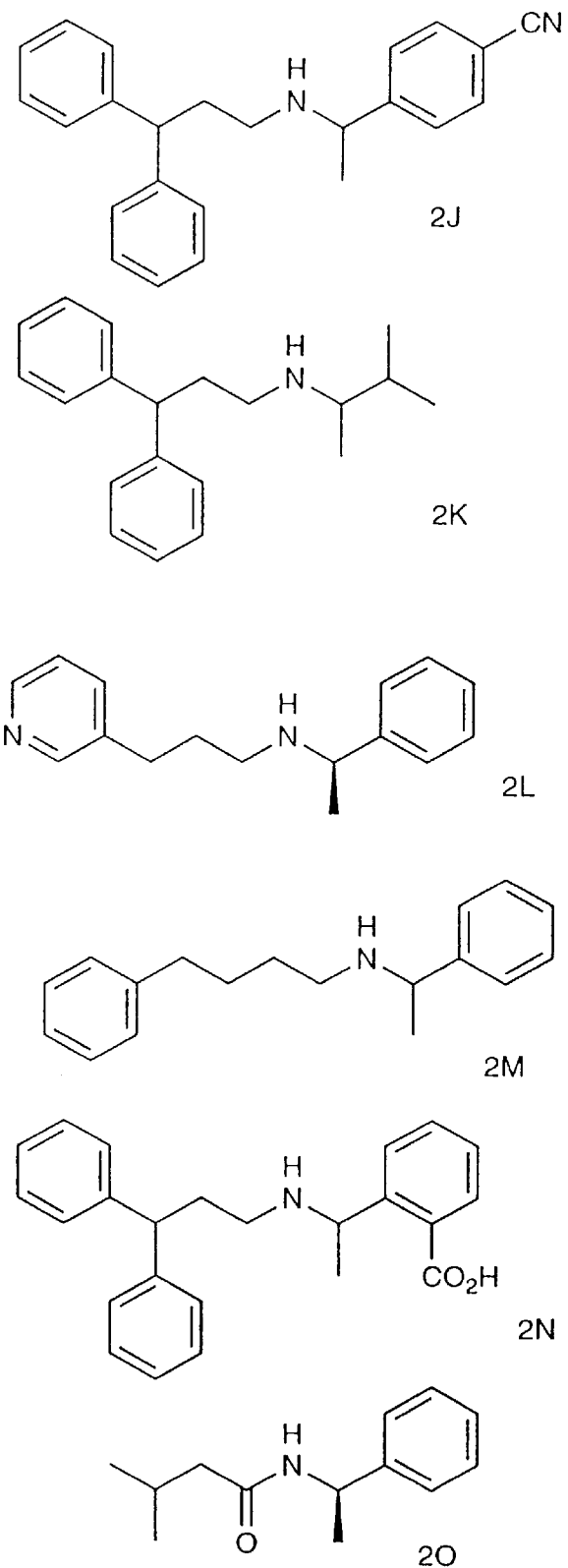
Figures 1, 2, 3, 4, 5, 6, 7, 8, 9, 10, 11, 12, 13:
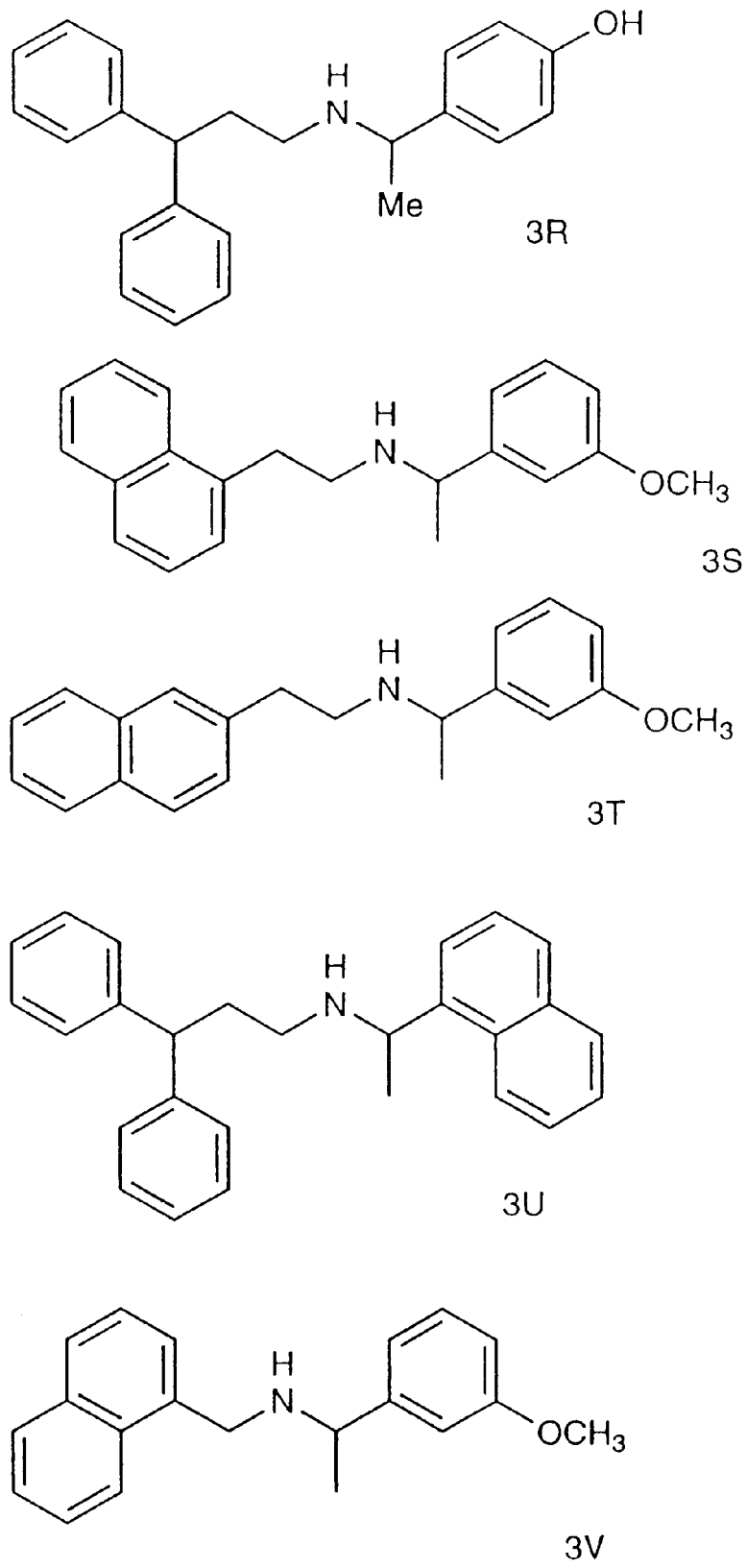
Figures 1, 2, 3, 4, 5, 6, 7, 8, 9, 10, 11, 12, 13, 14, 15, 16, 17, 18, 19:
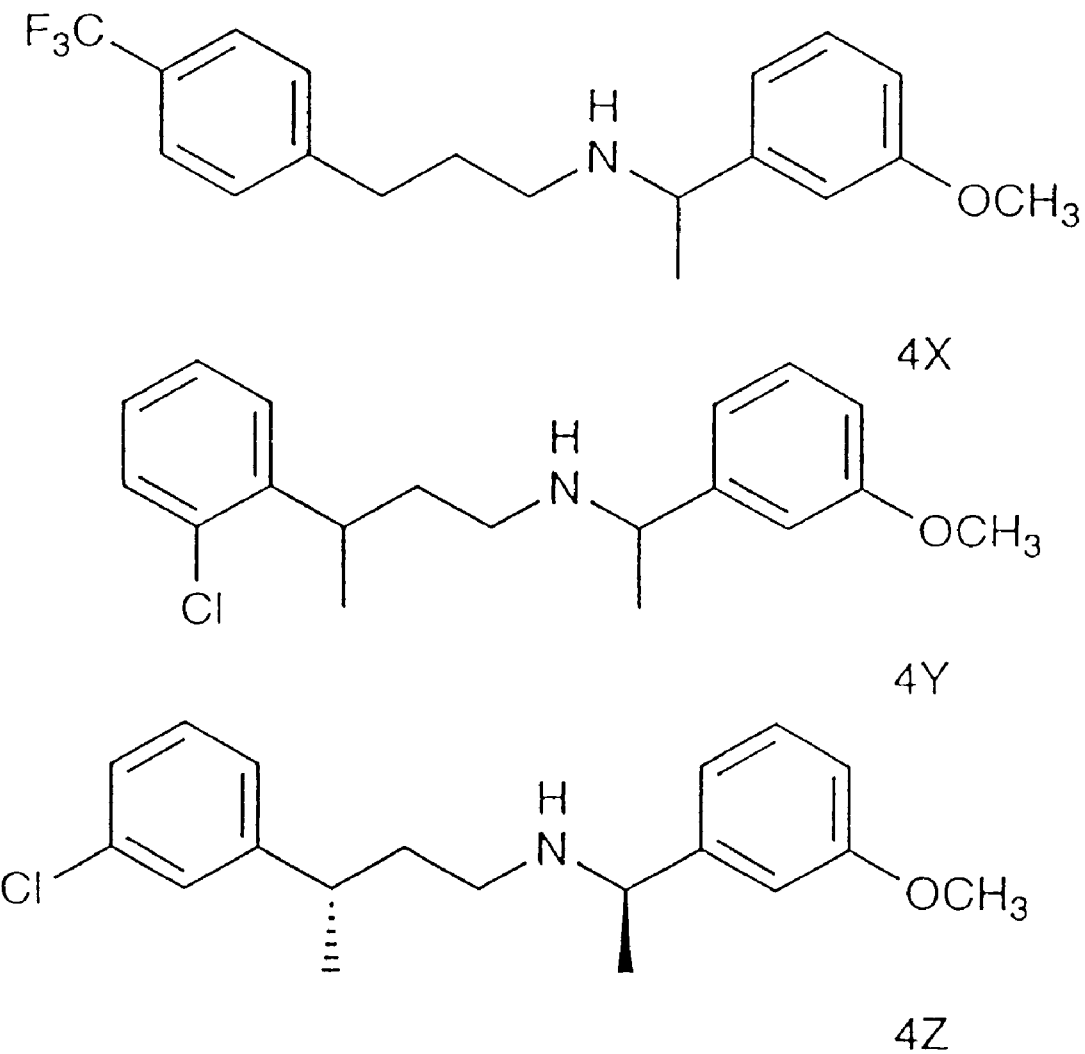
Figures 1, 2, 3, 4, 5, 6, 7, 8, 9, 10, 11, 12, 13, 14, 15, 16, 17, 18, 19, 20:
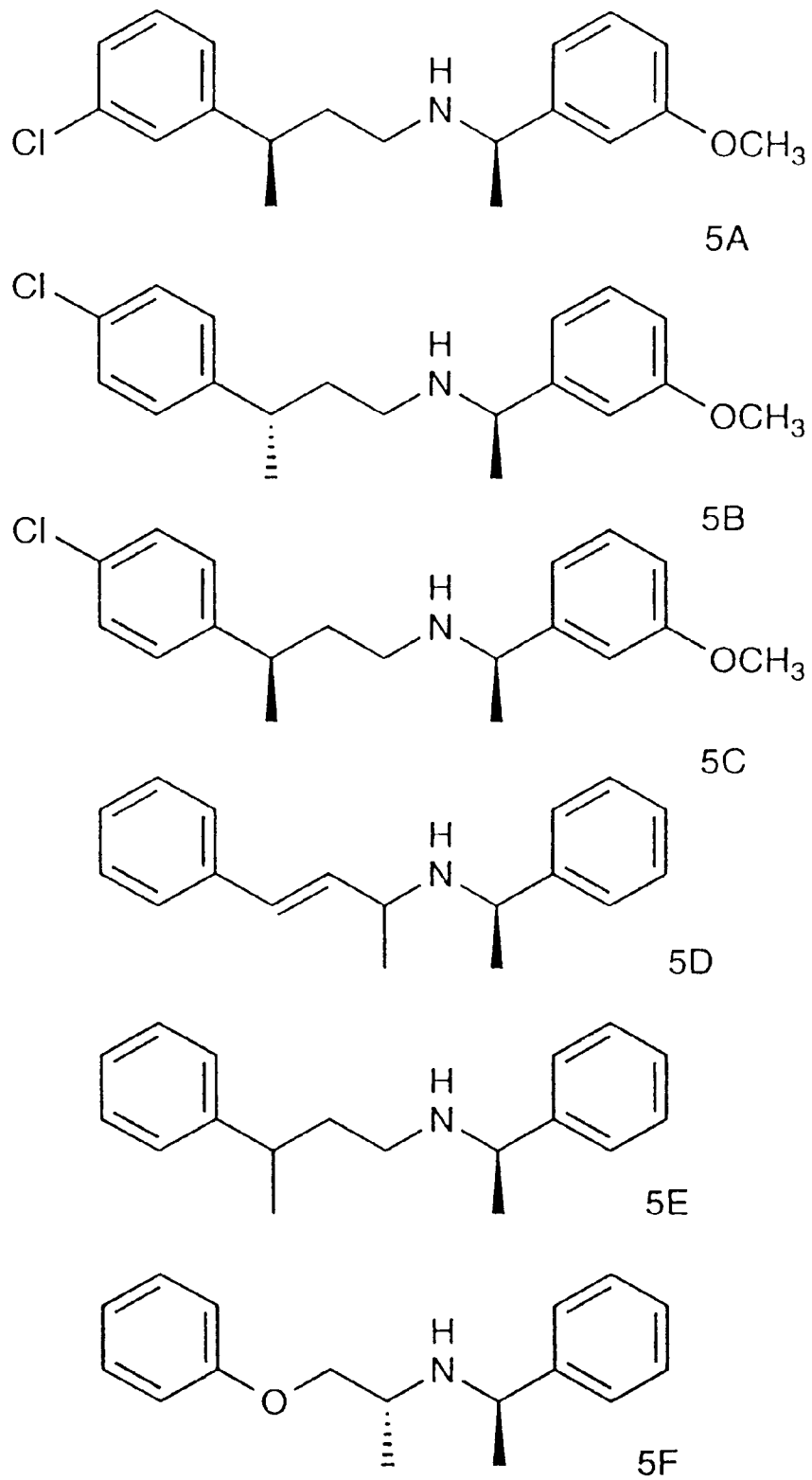
Figures 1, 2, 3, 4, 5, 6, 7, 8, 9, 10, 11, 12, 13, 14, 15, 16, 17, 18, 19, 20, 21, 22, 23, 24, 25, 26, 27, 28:
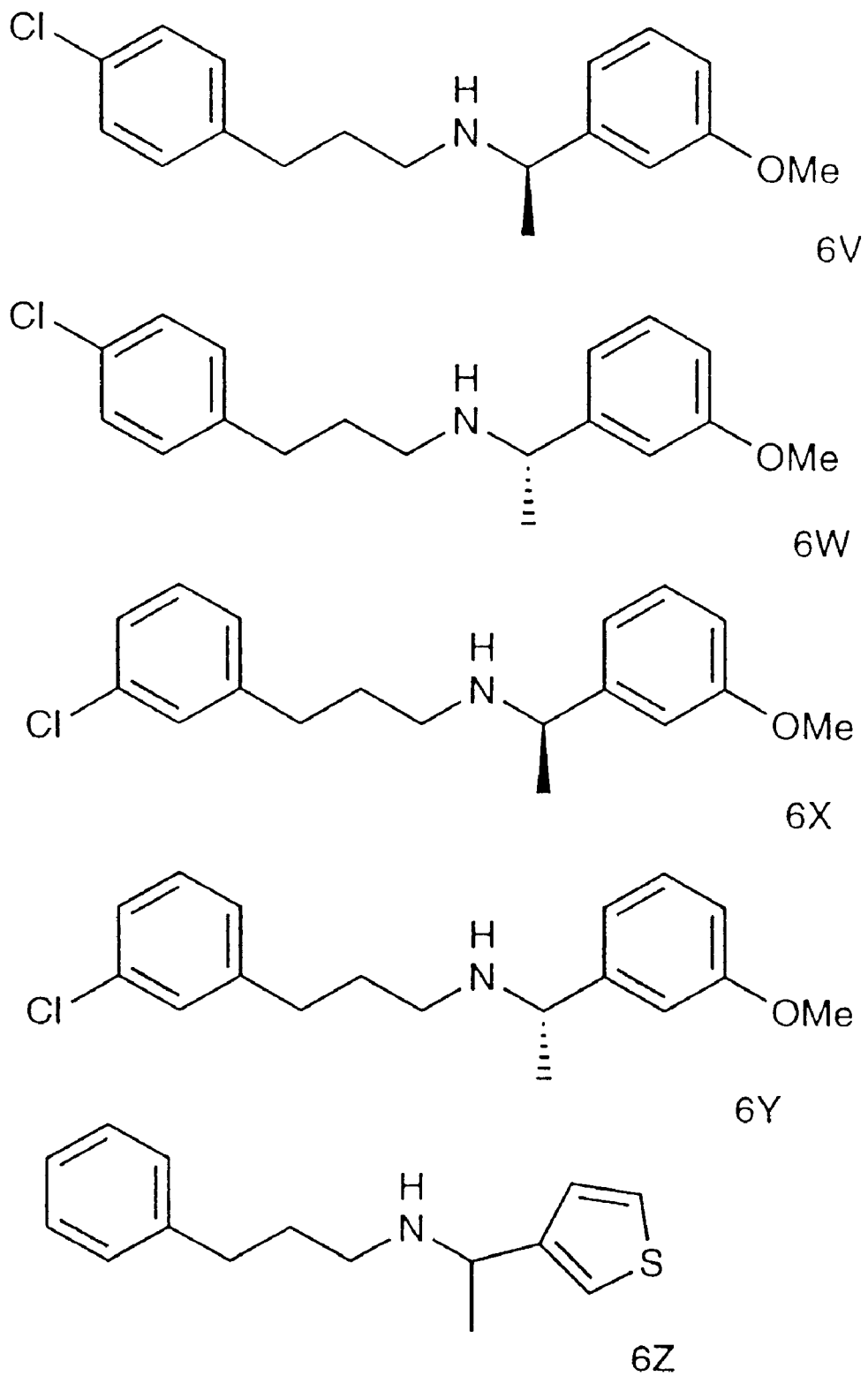
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29:
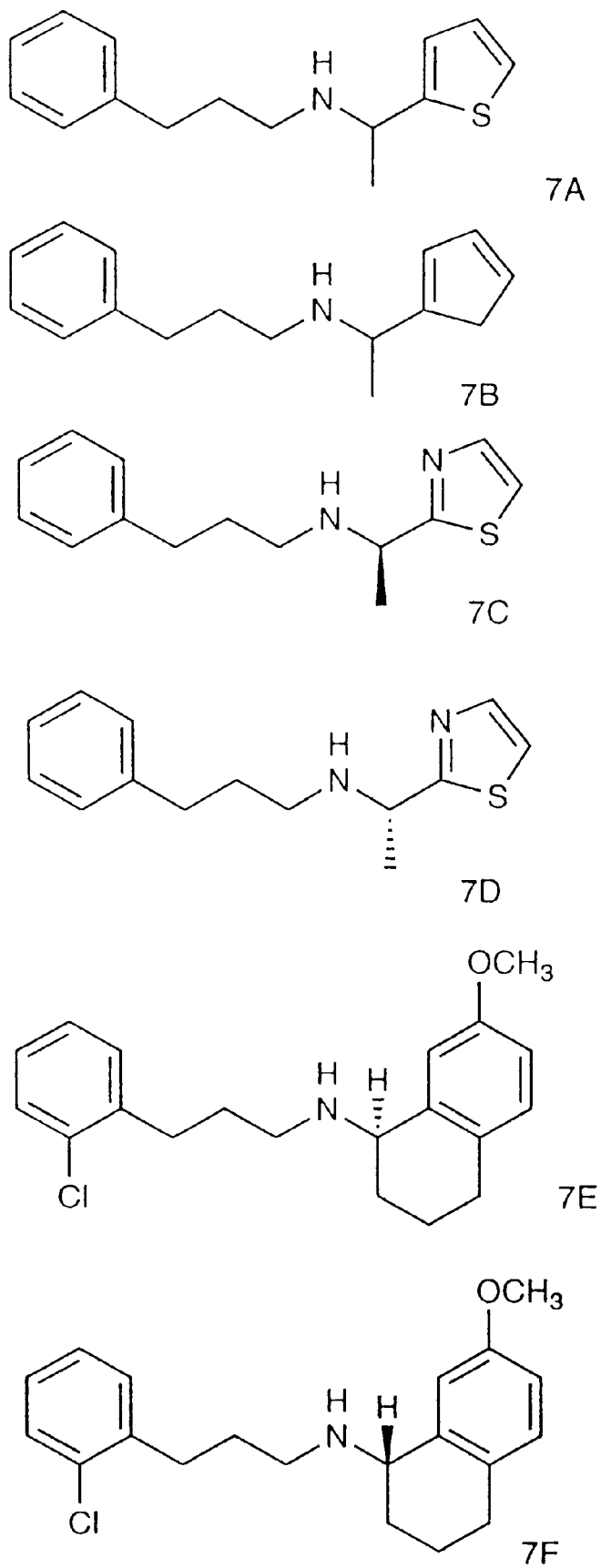
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
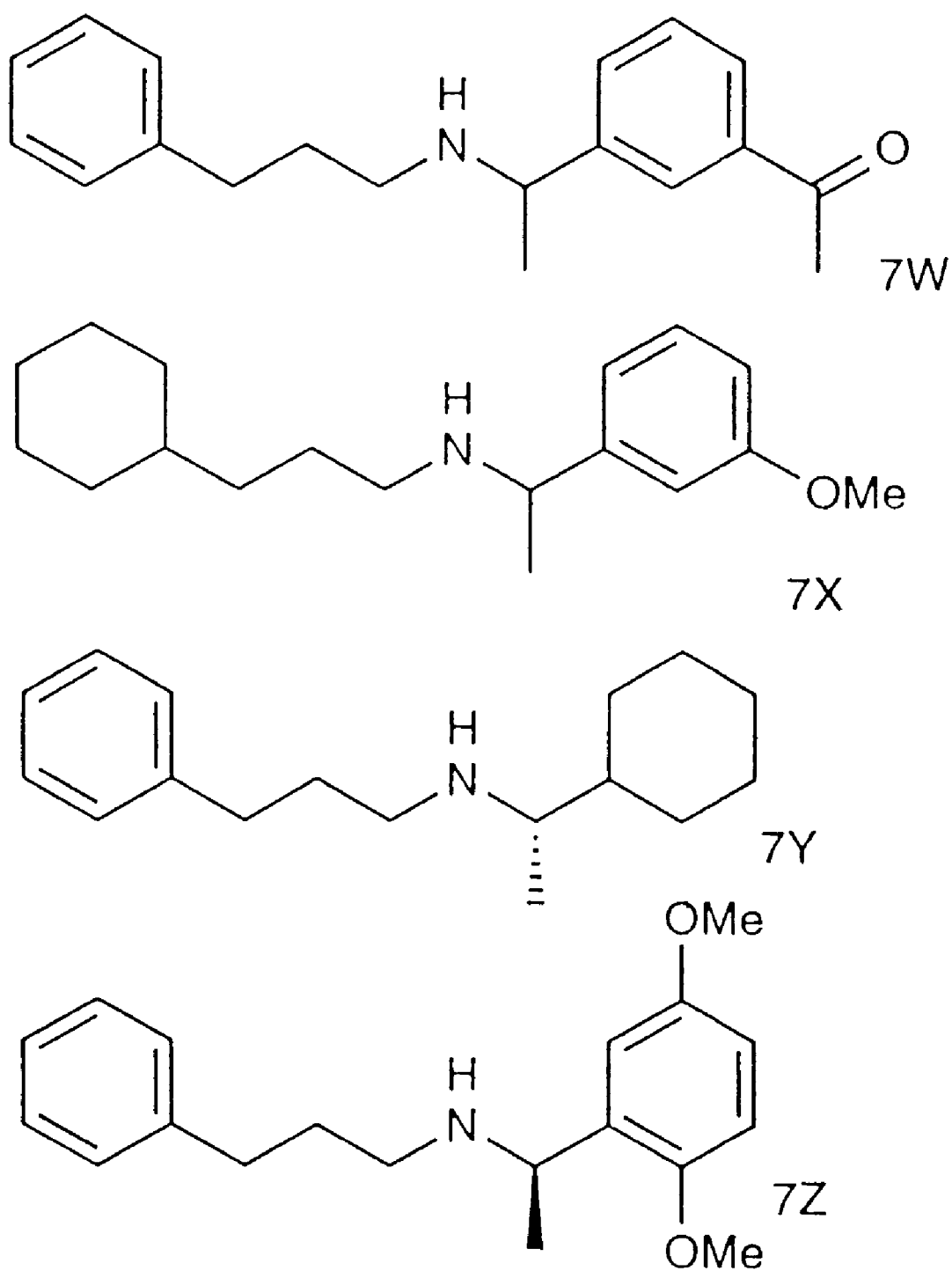
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
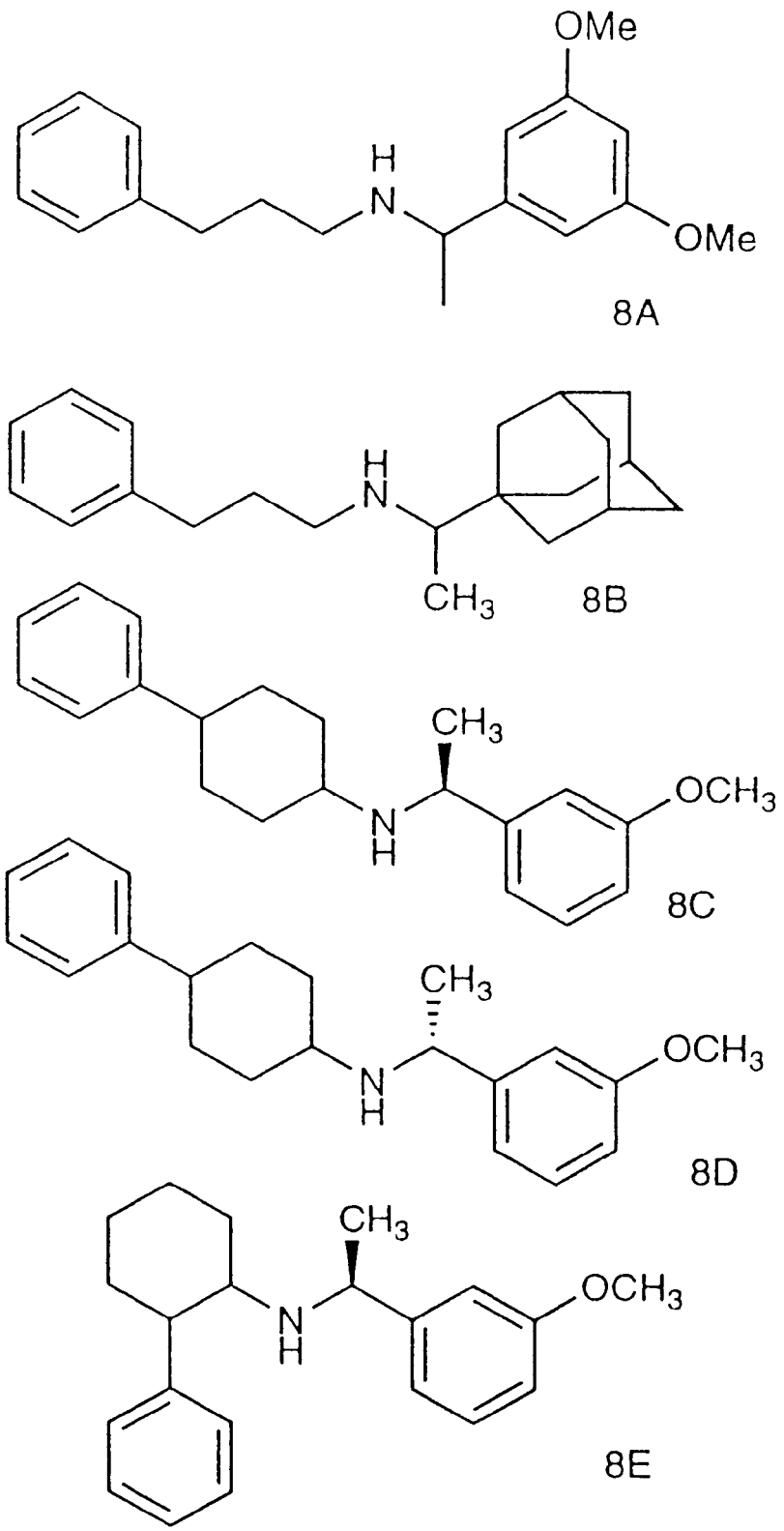
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
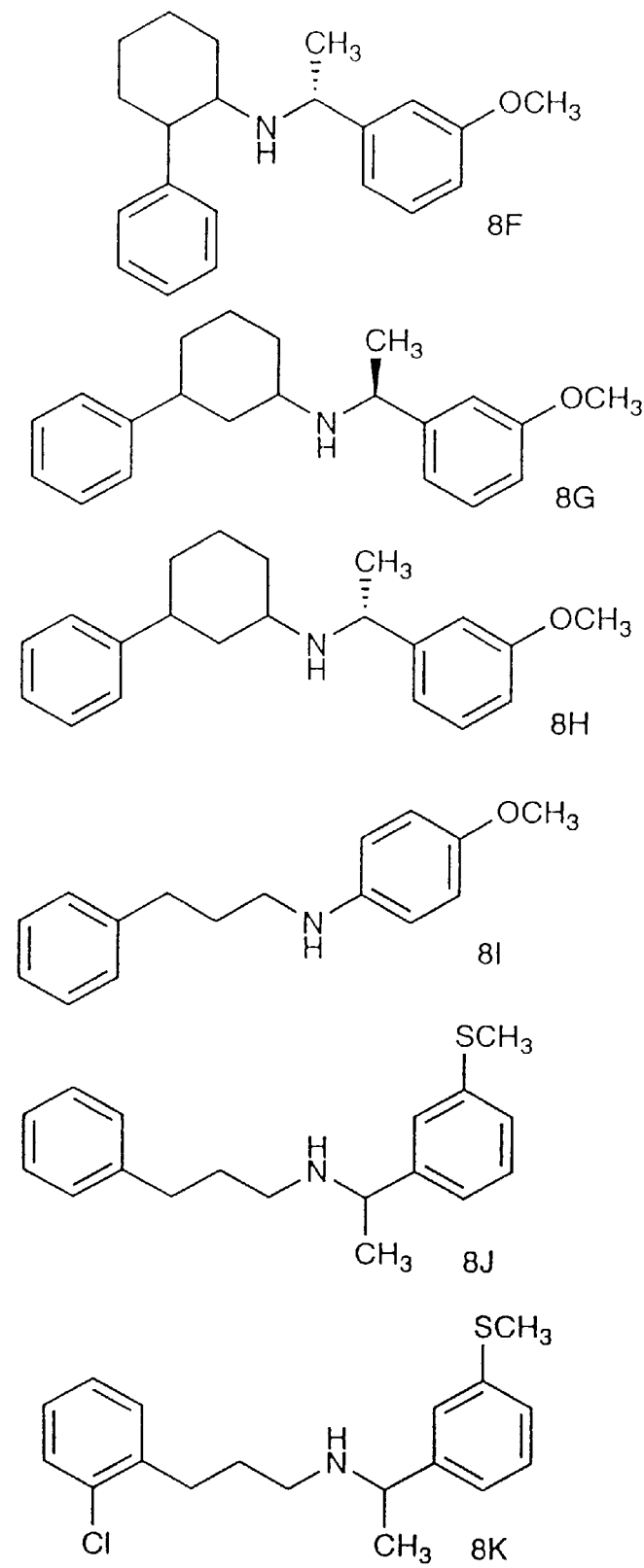
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
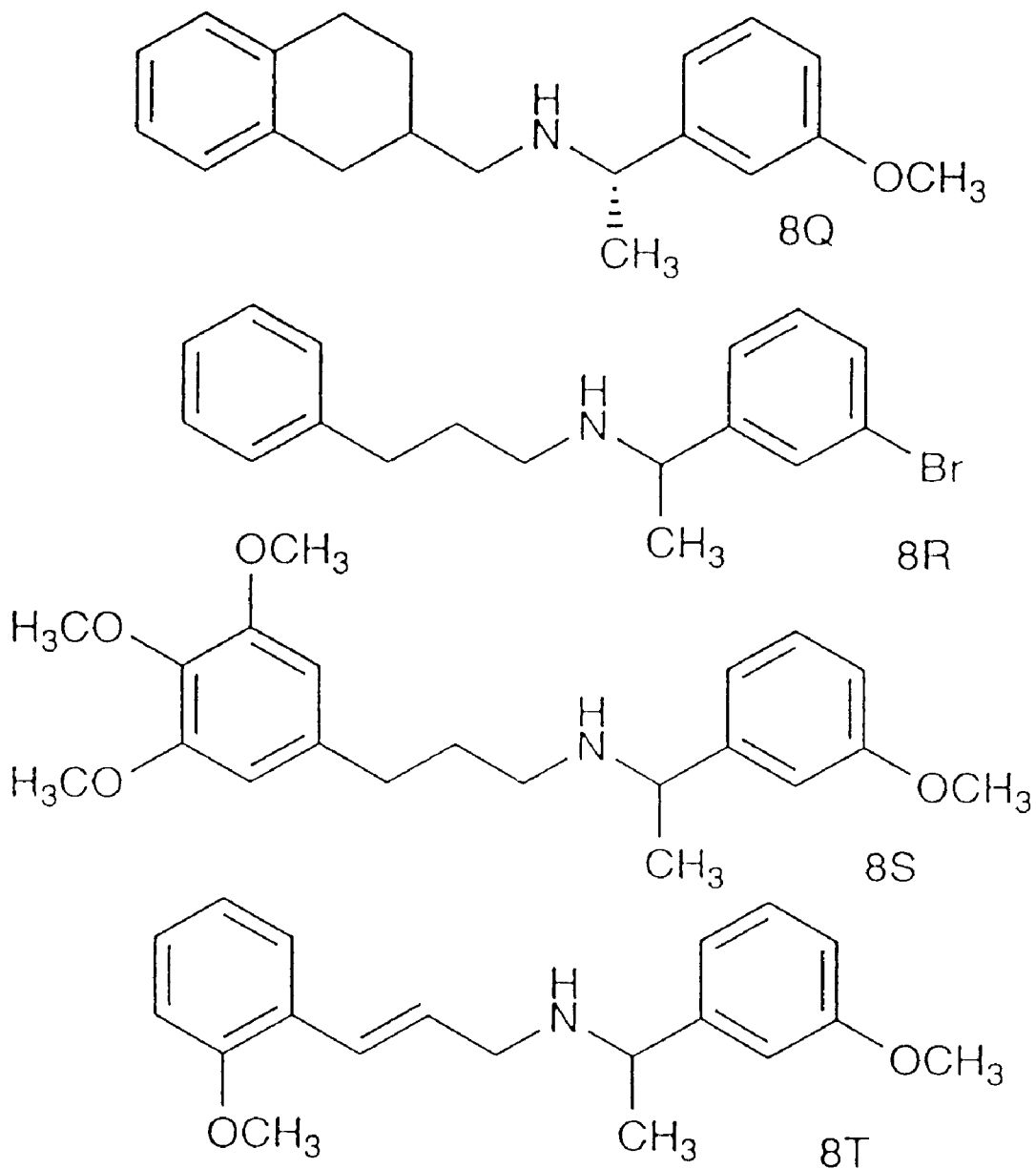
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
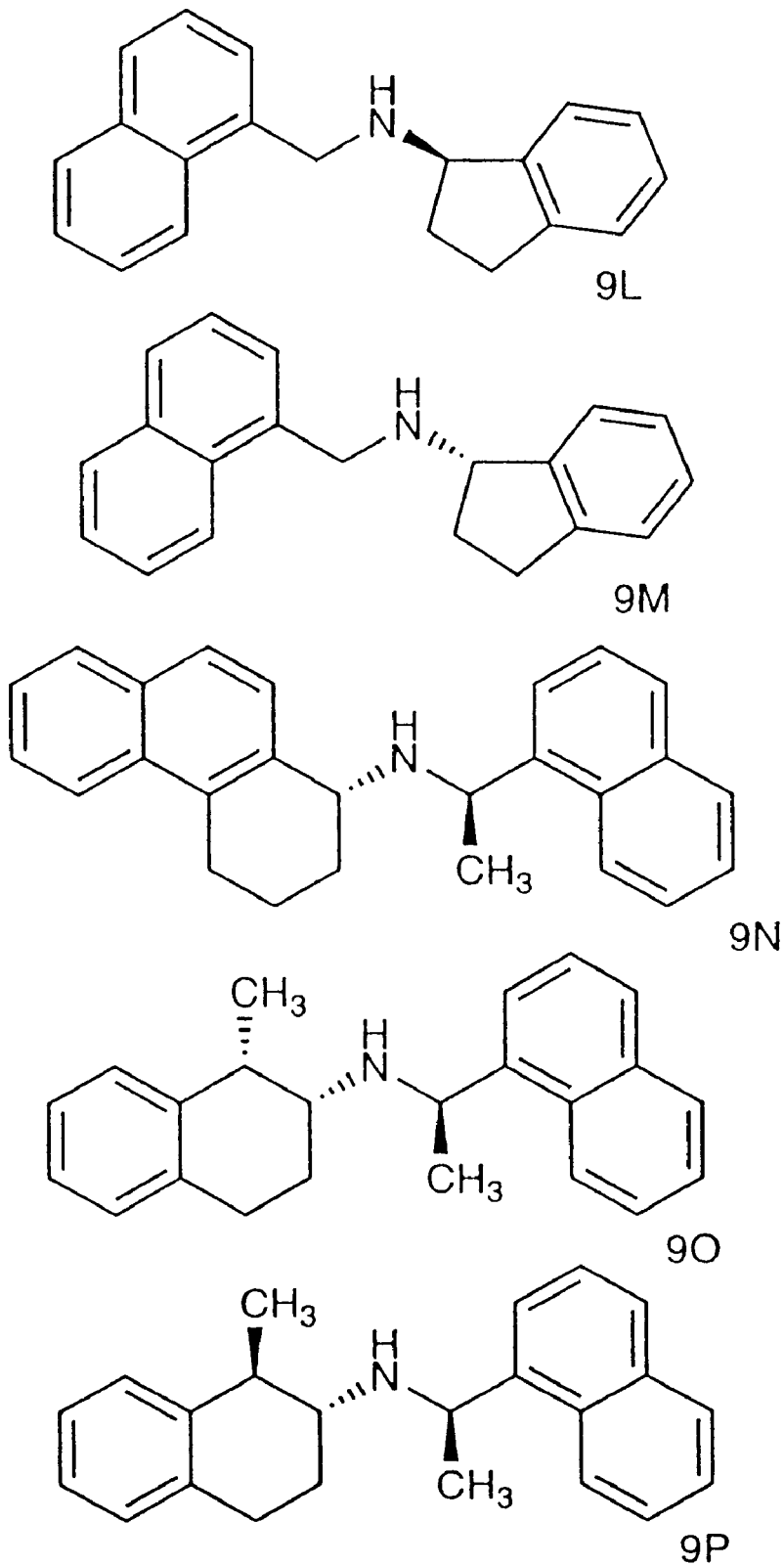
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
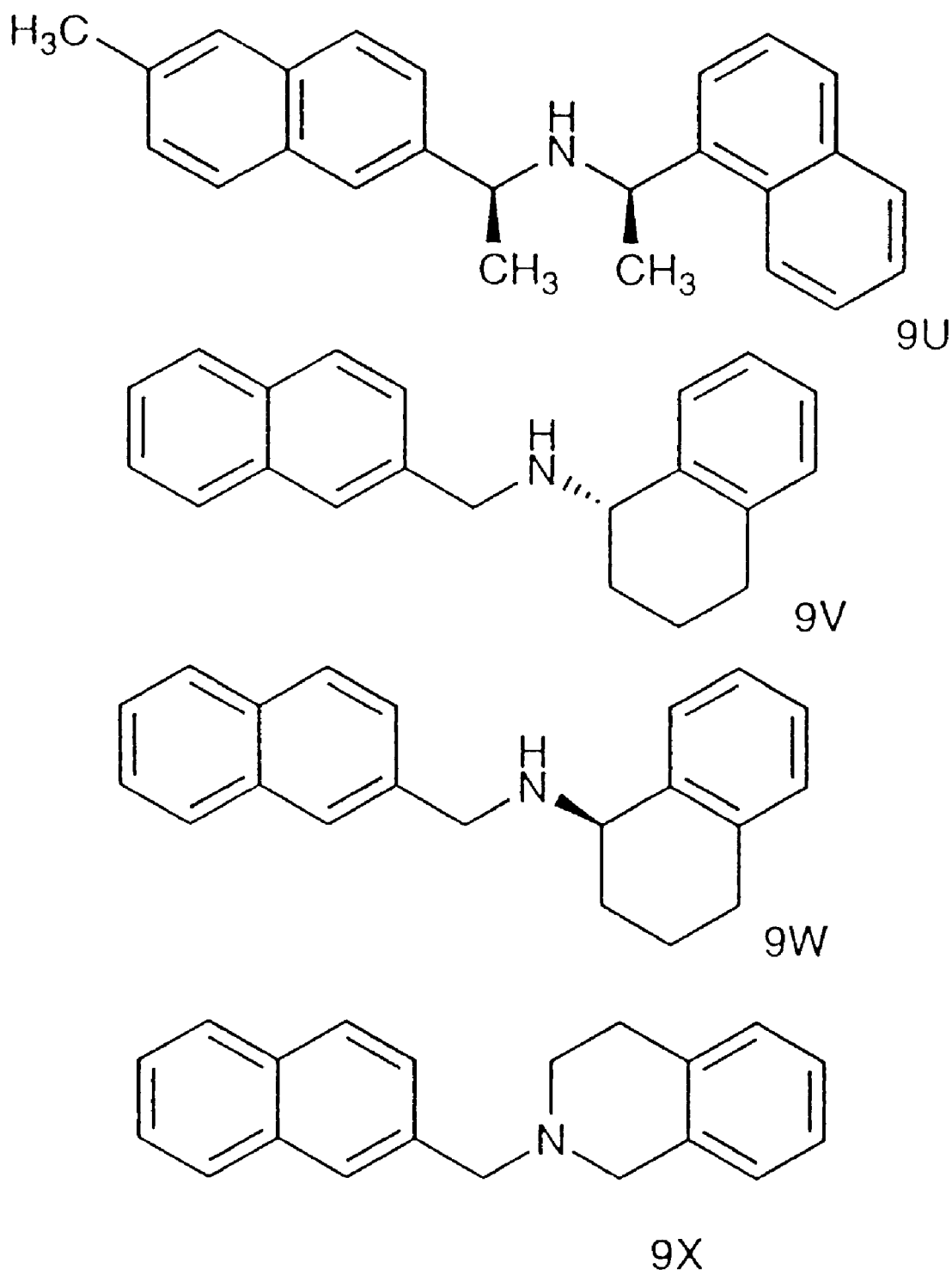
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
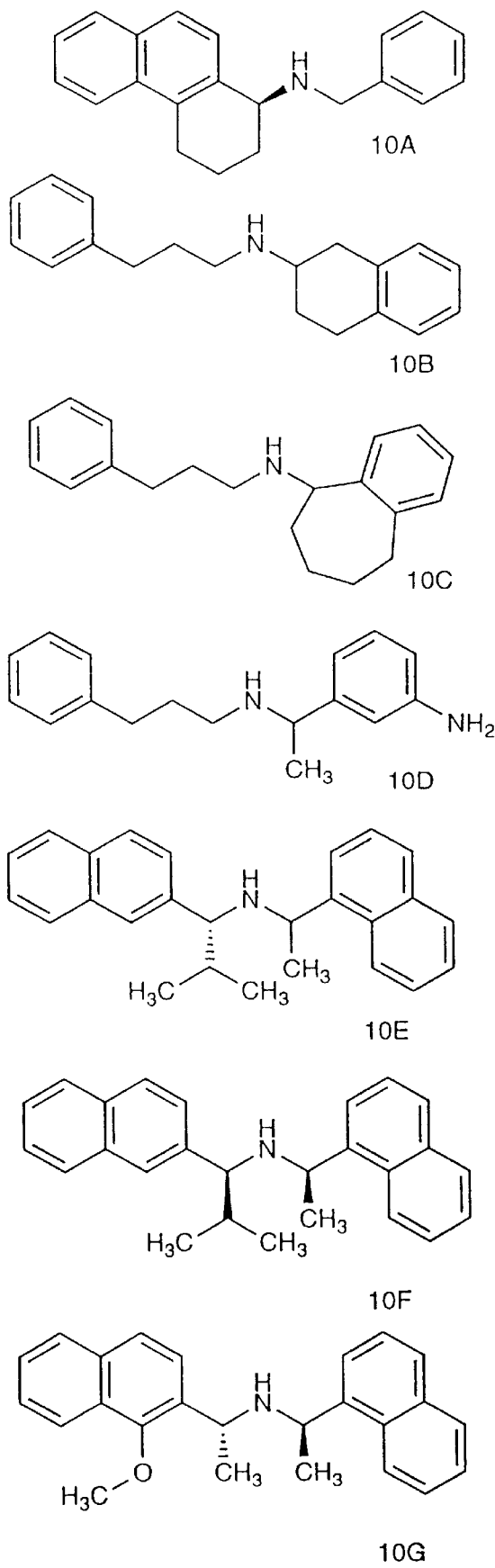
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
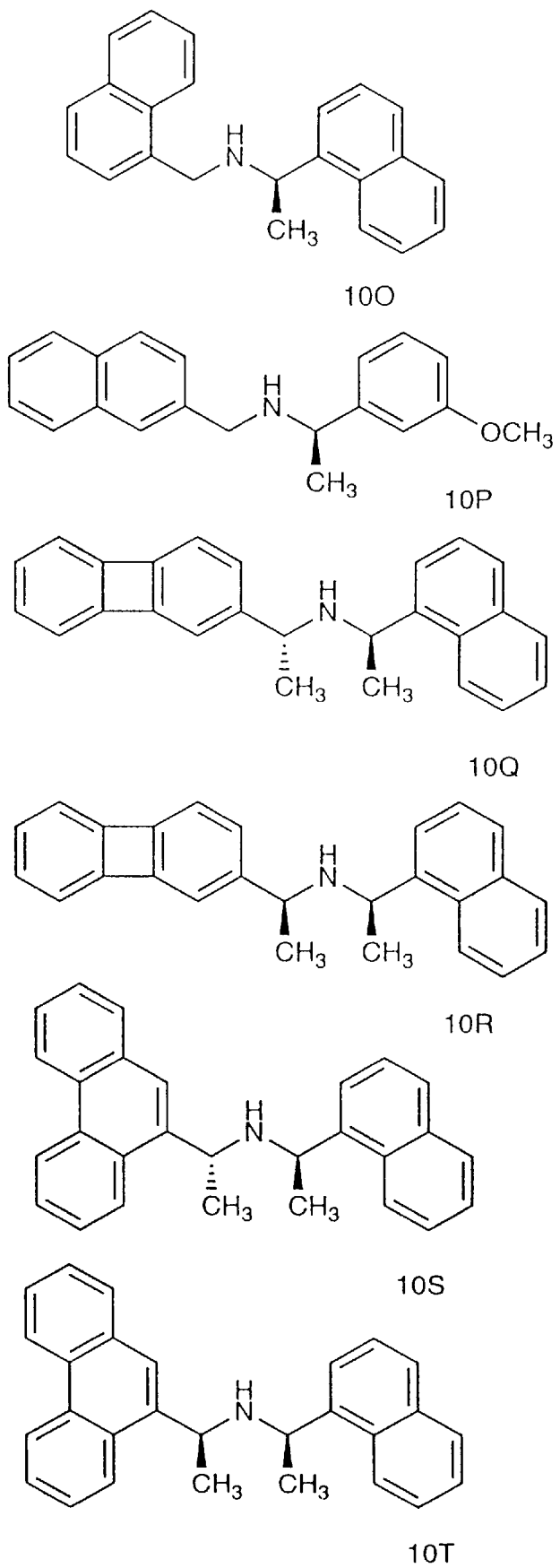
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
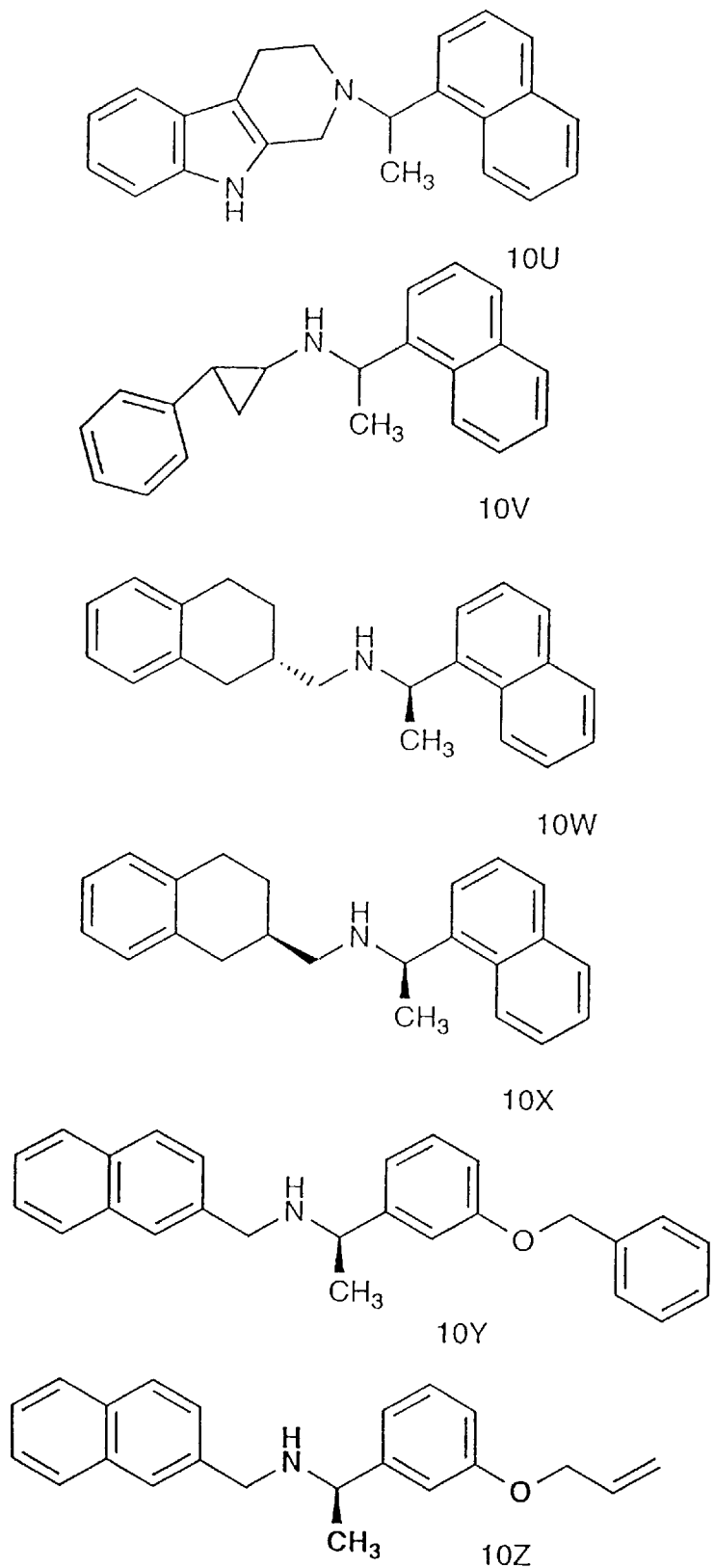
Figures 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
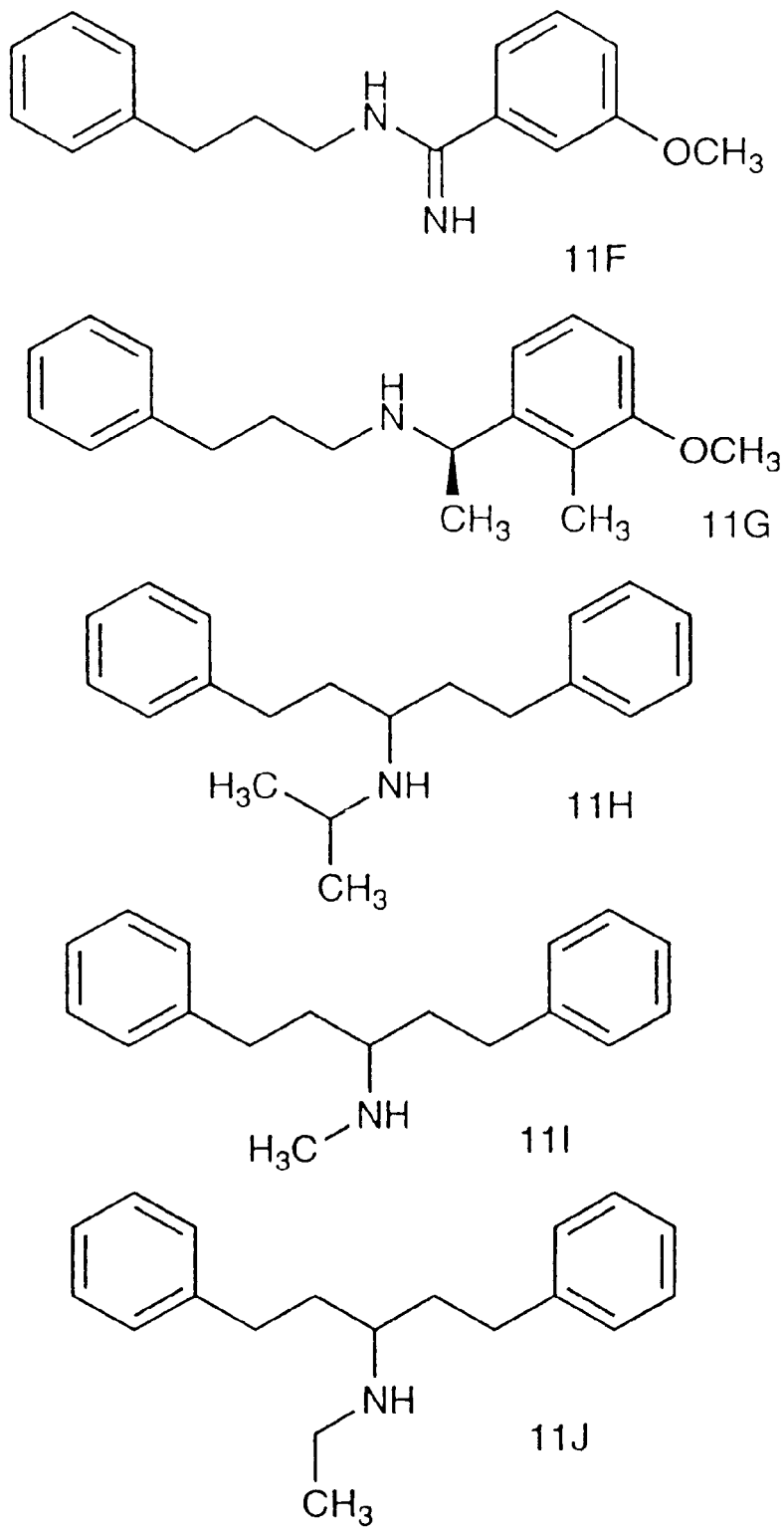
Figures 1, 53:
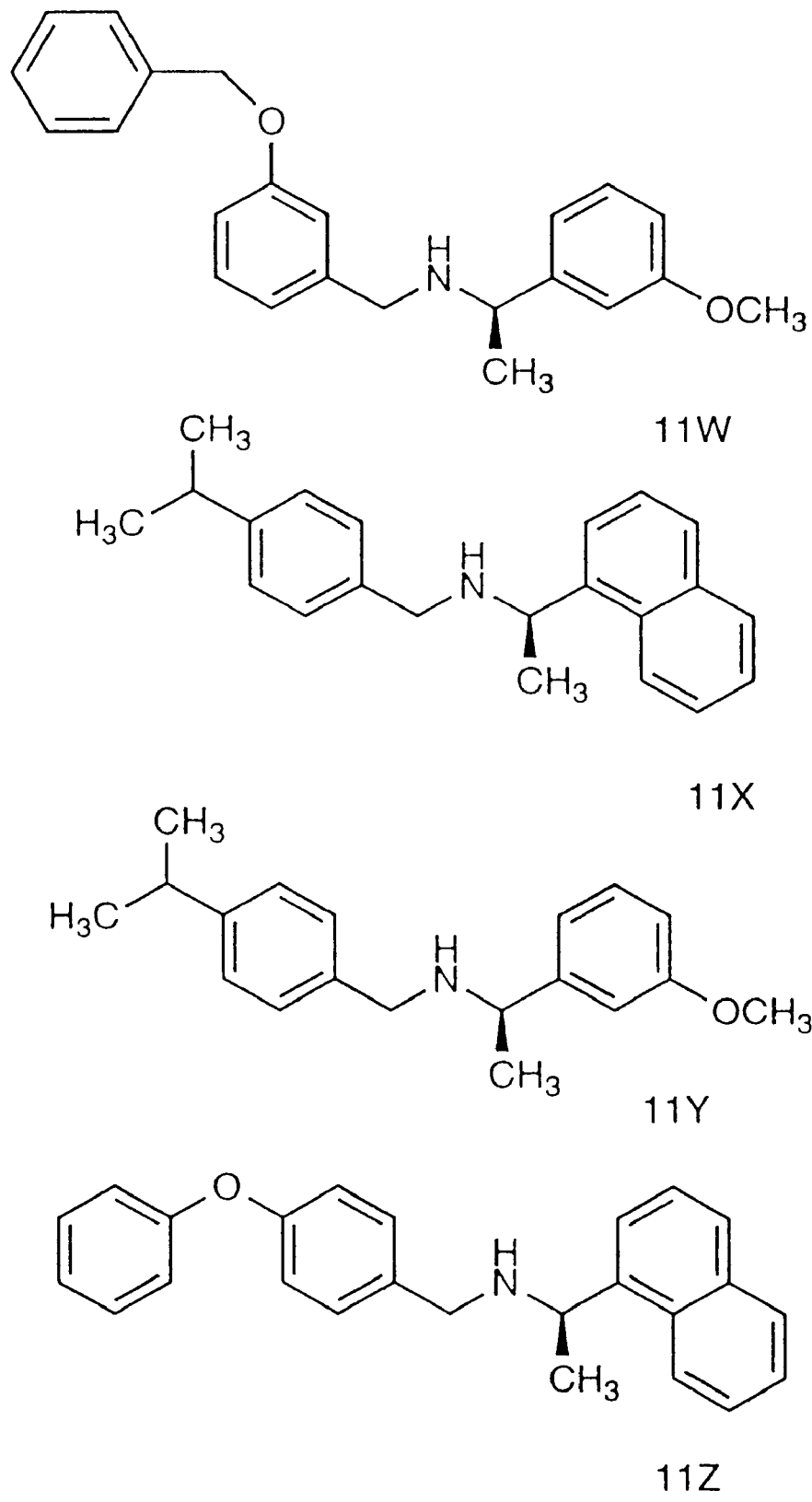
Figures 1, 55:
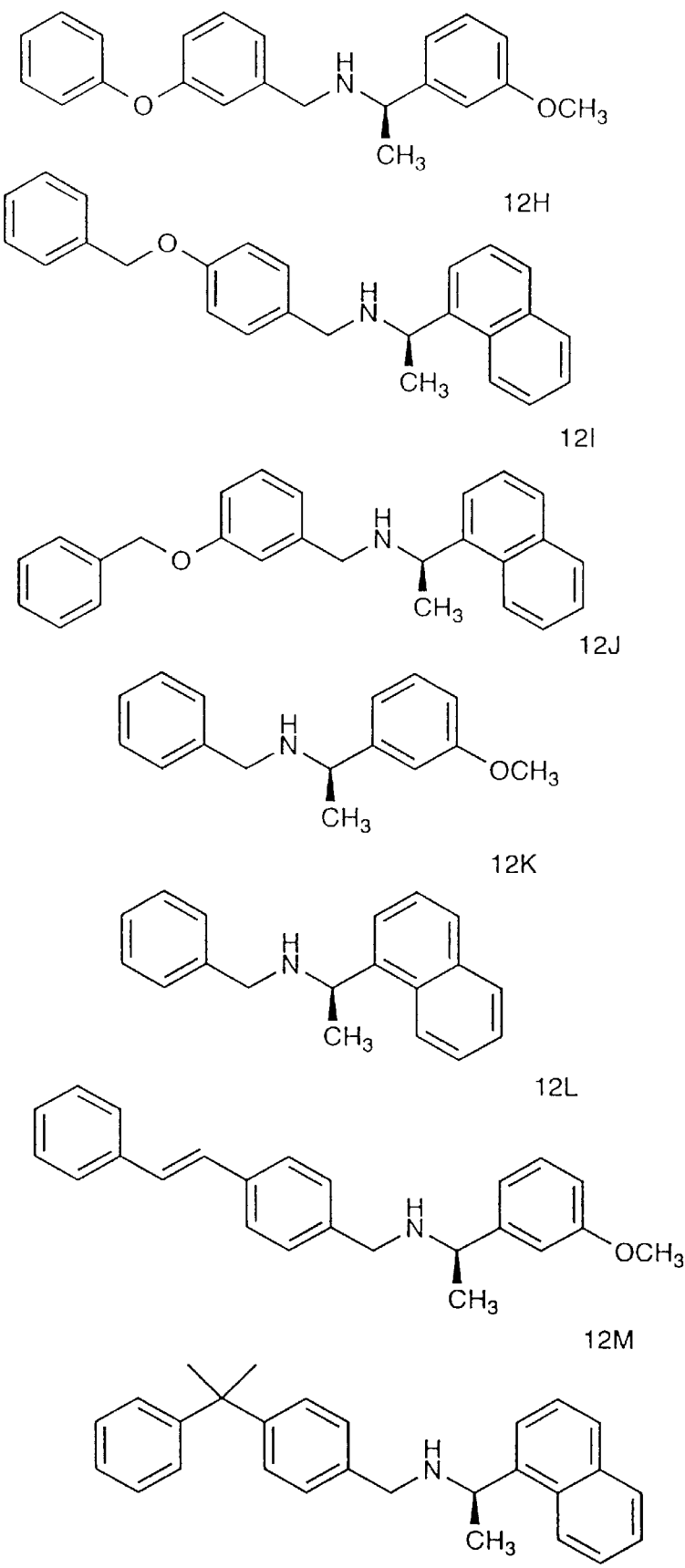
Figures 1, 56:
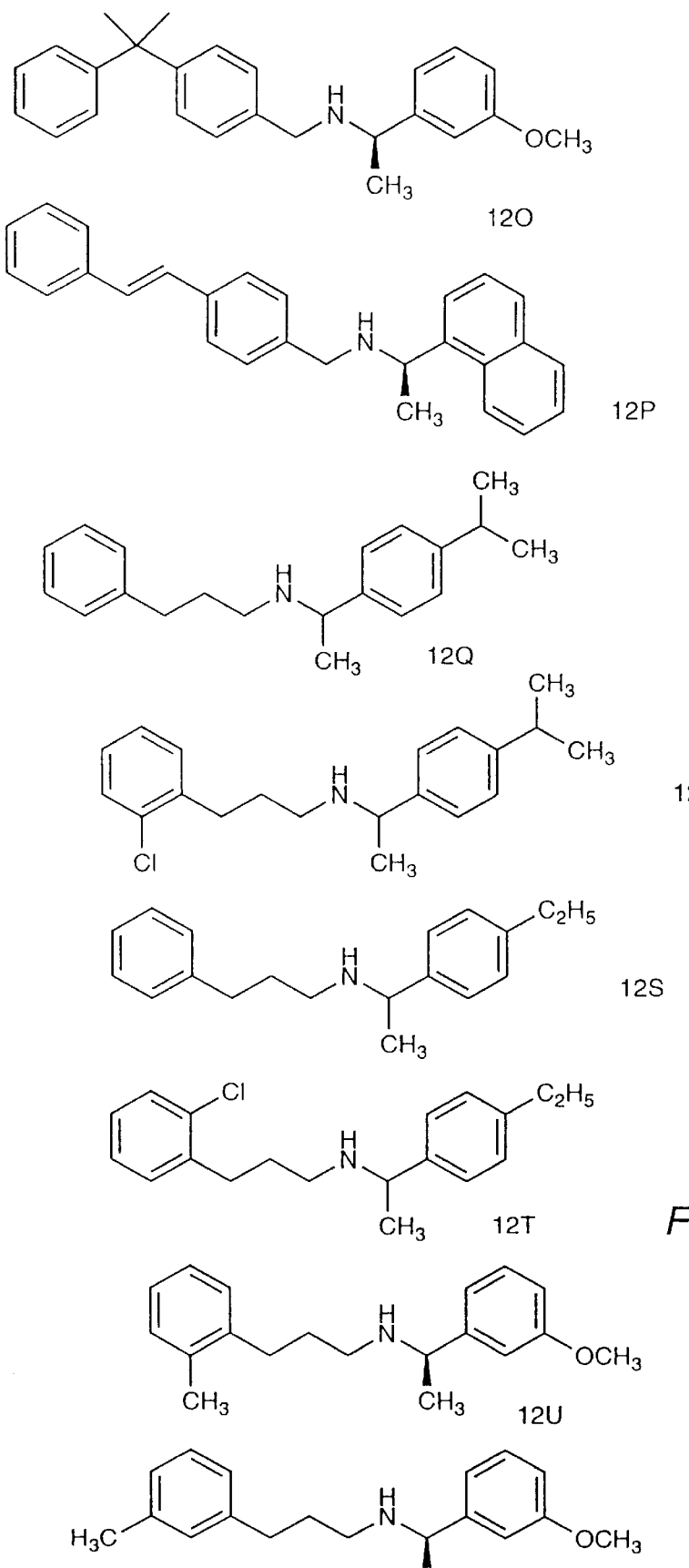
Figures 1, 57:
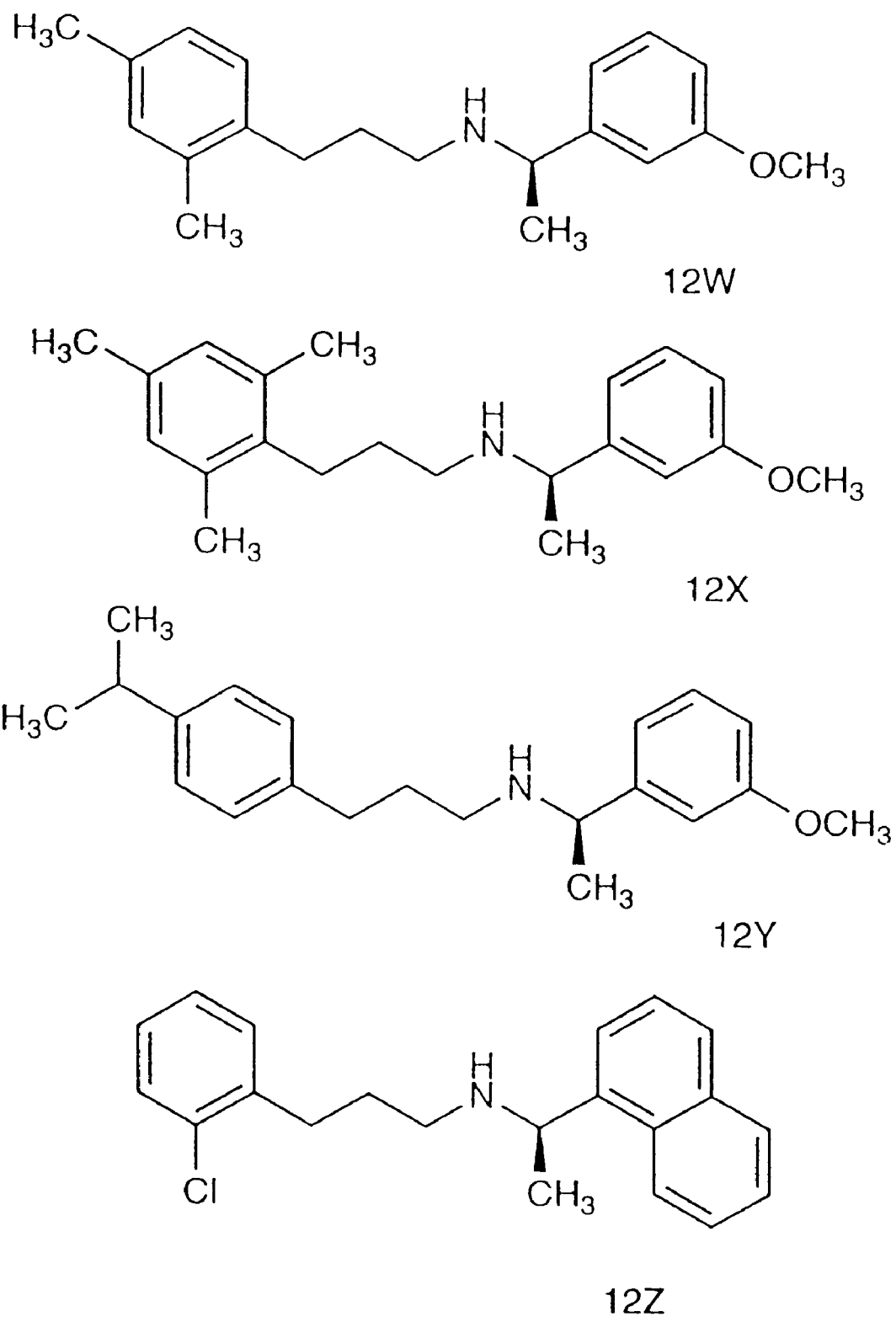
Figures 1, 58:
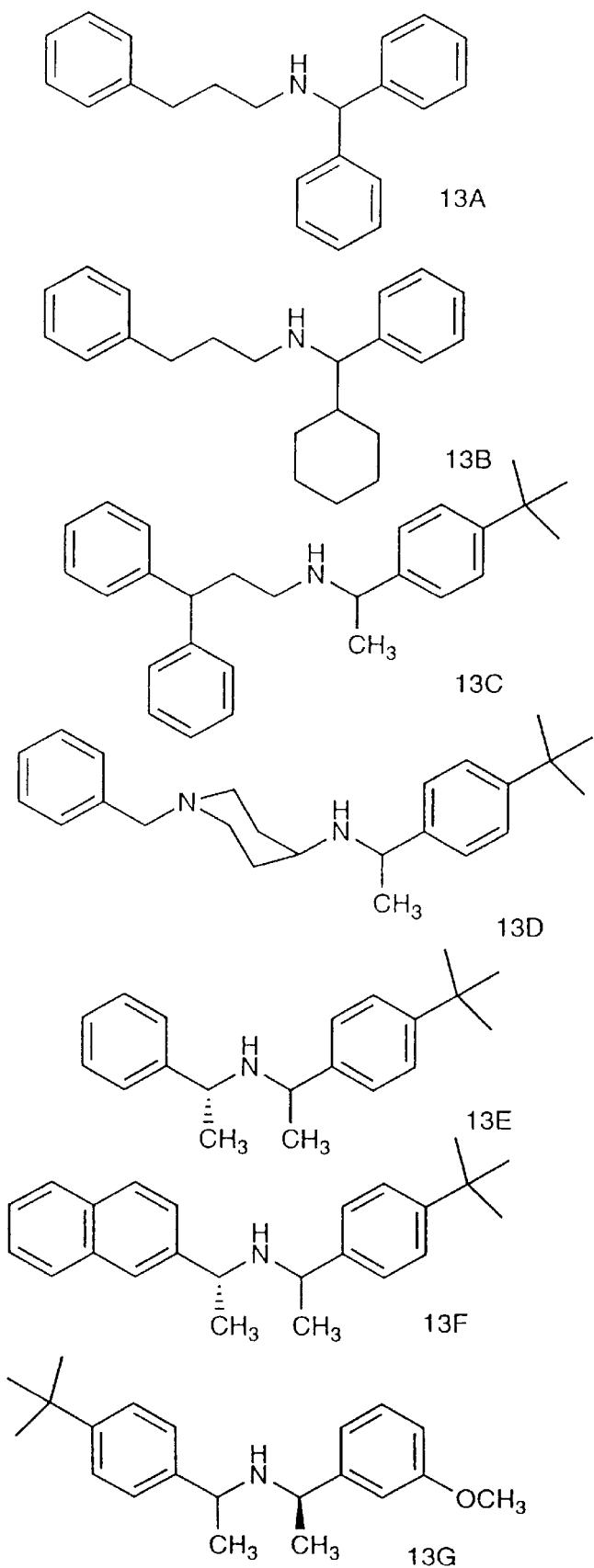
Figures 1, 59:
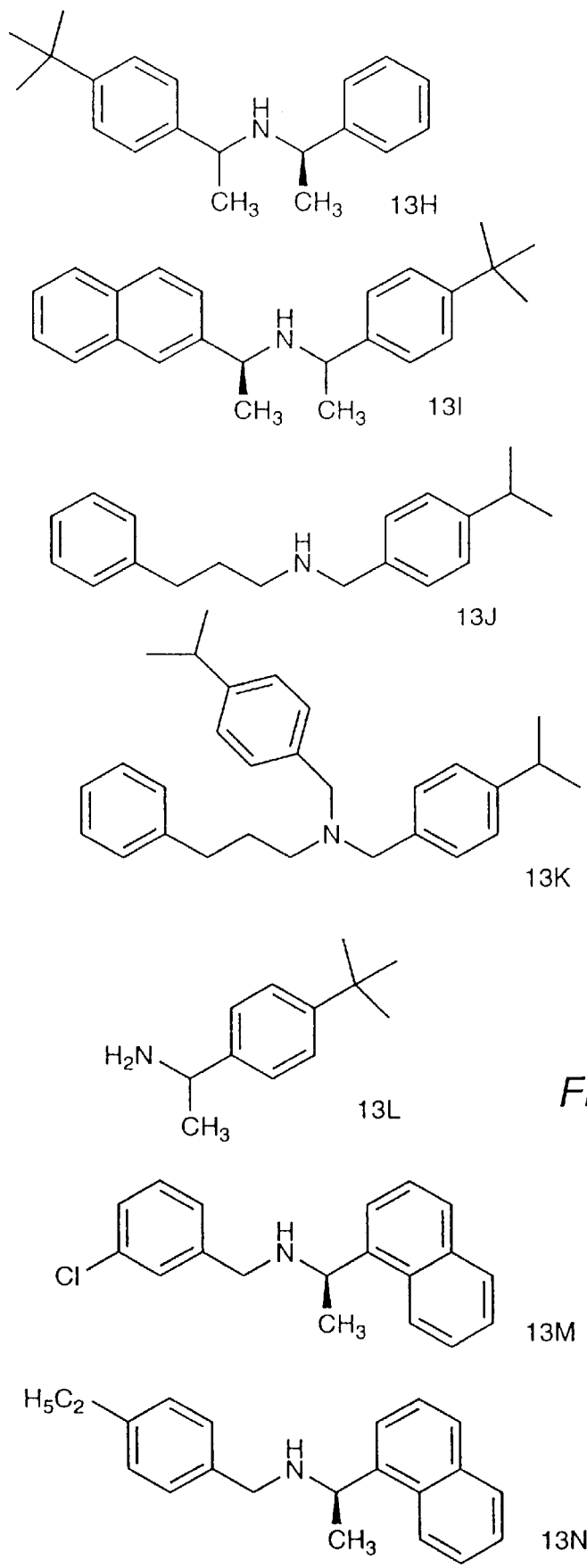
Figures 1, 61:
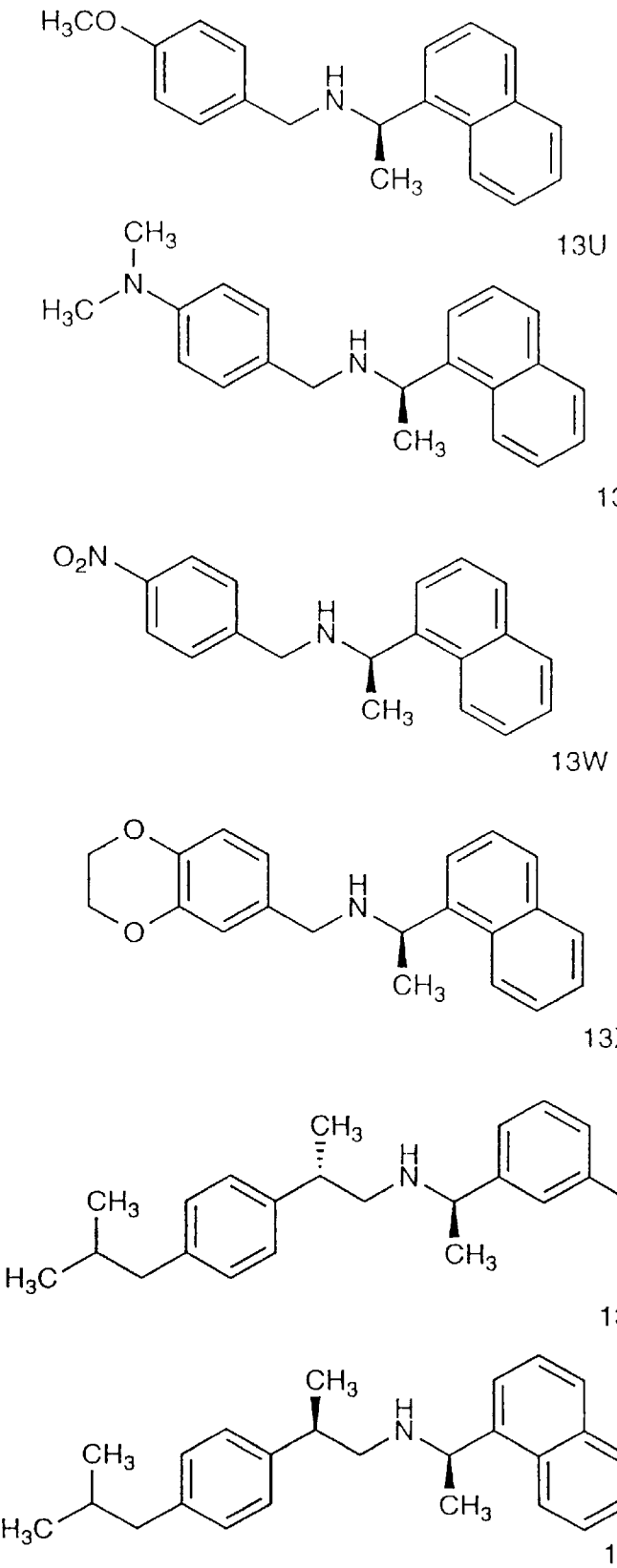
Figures 1, 62:
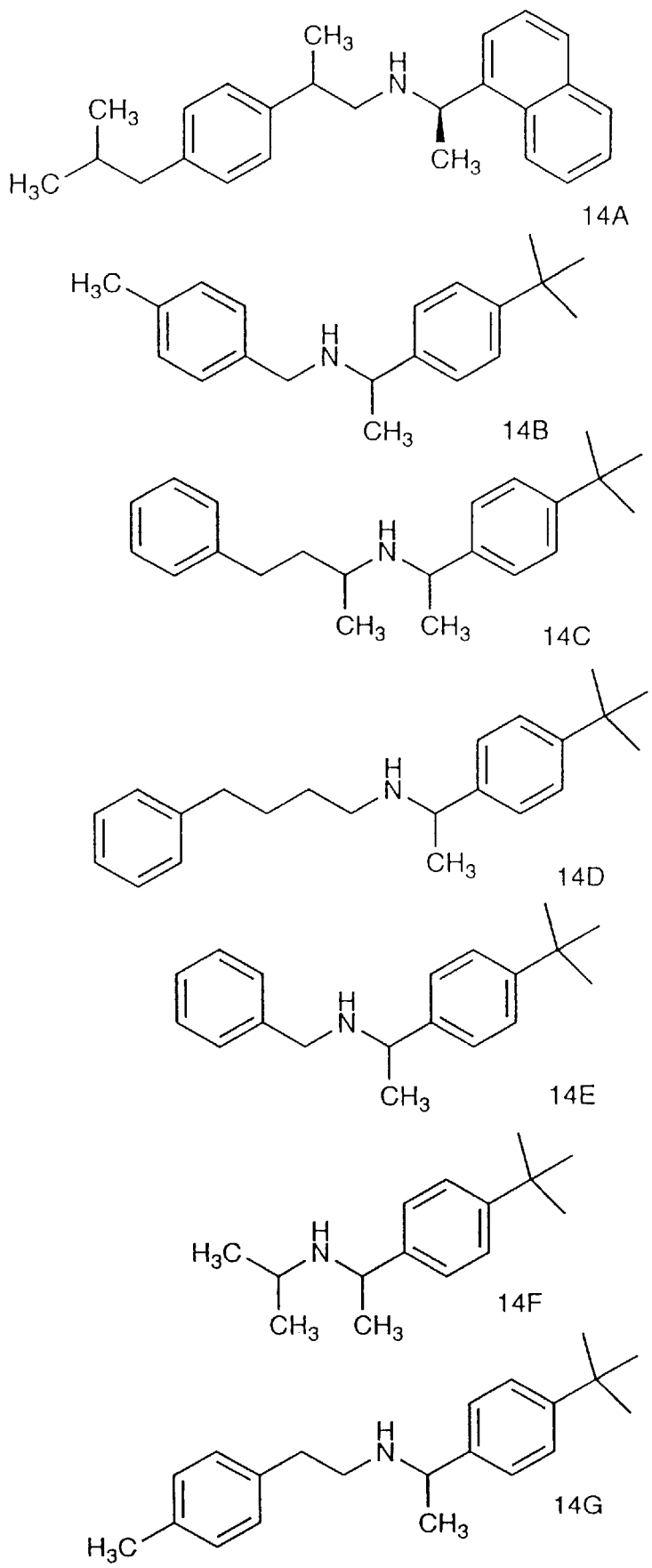
Figures 1, 63:
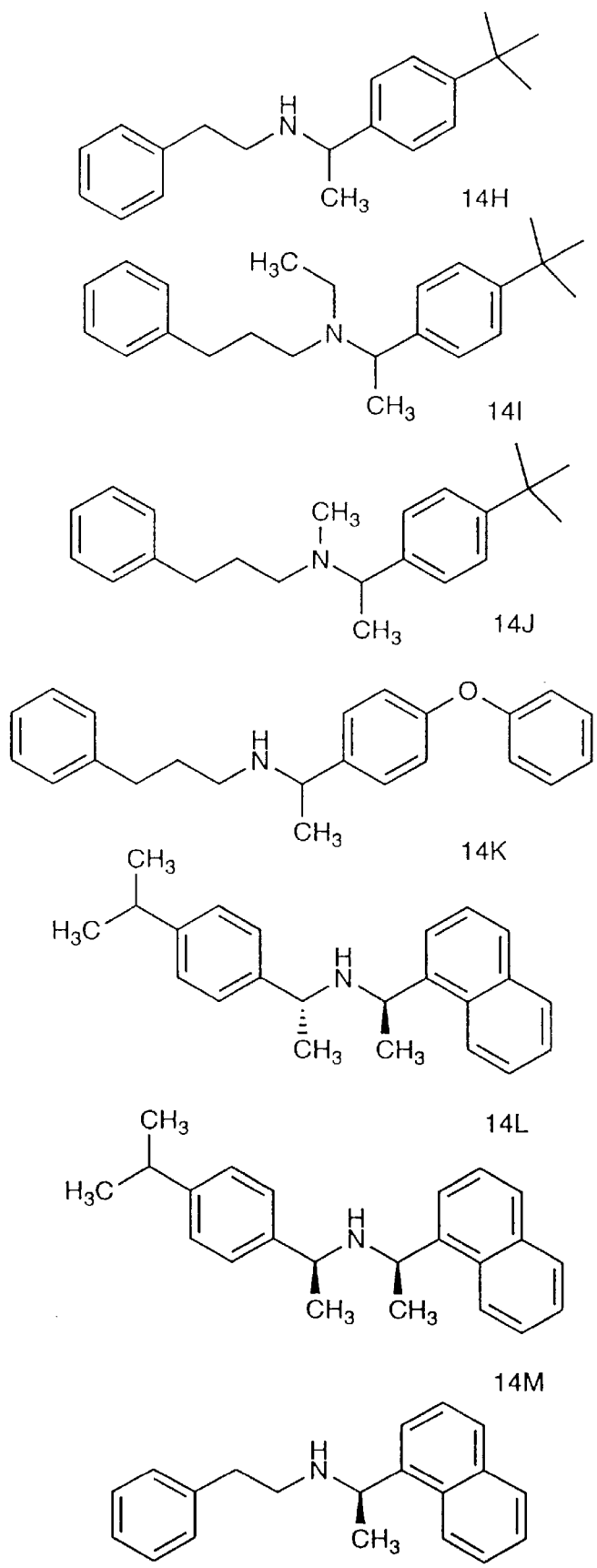
Figures 1, 68:
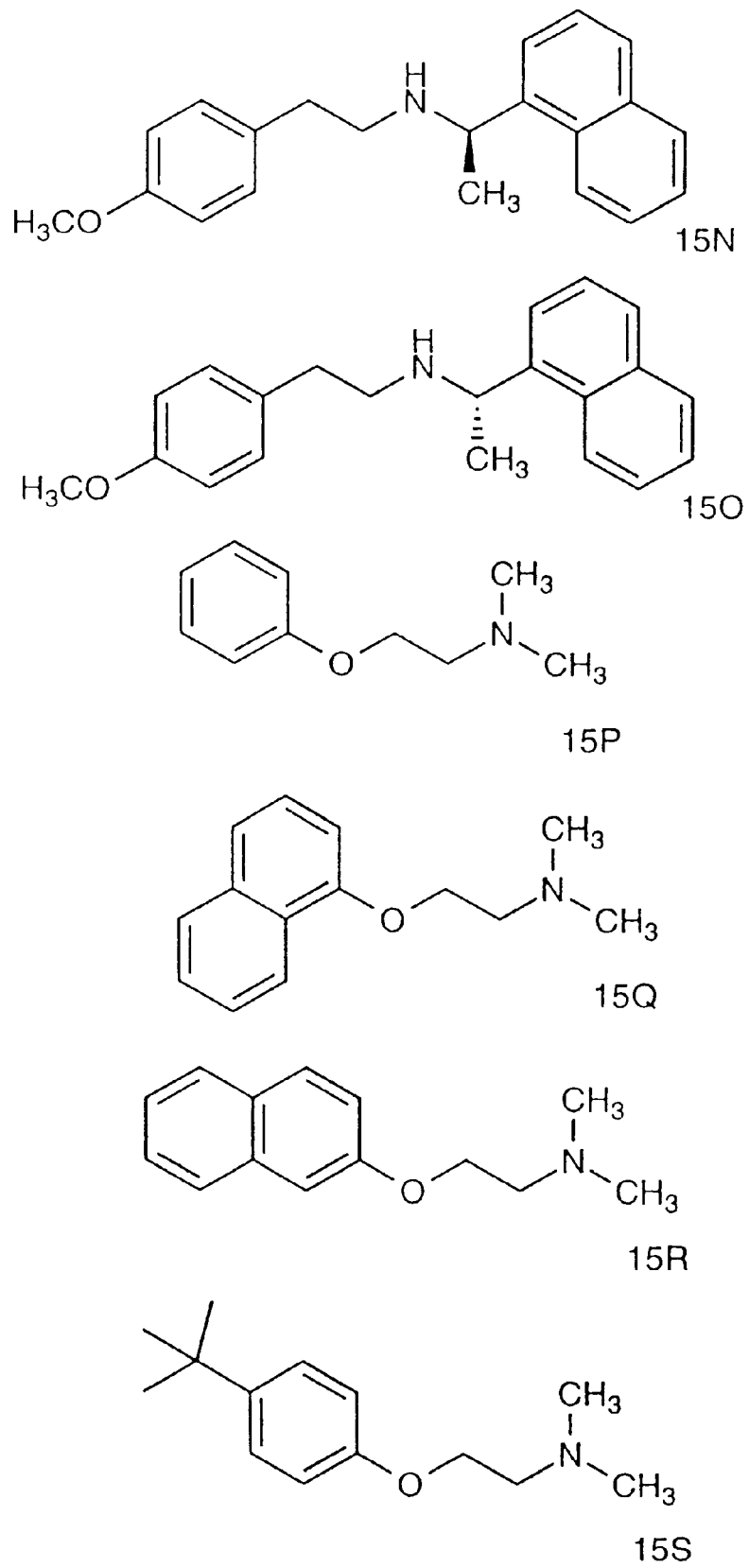
Figures 1, 72:
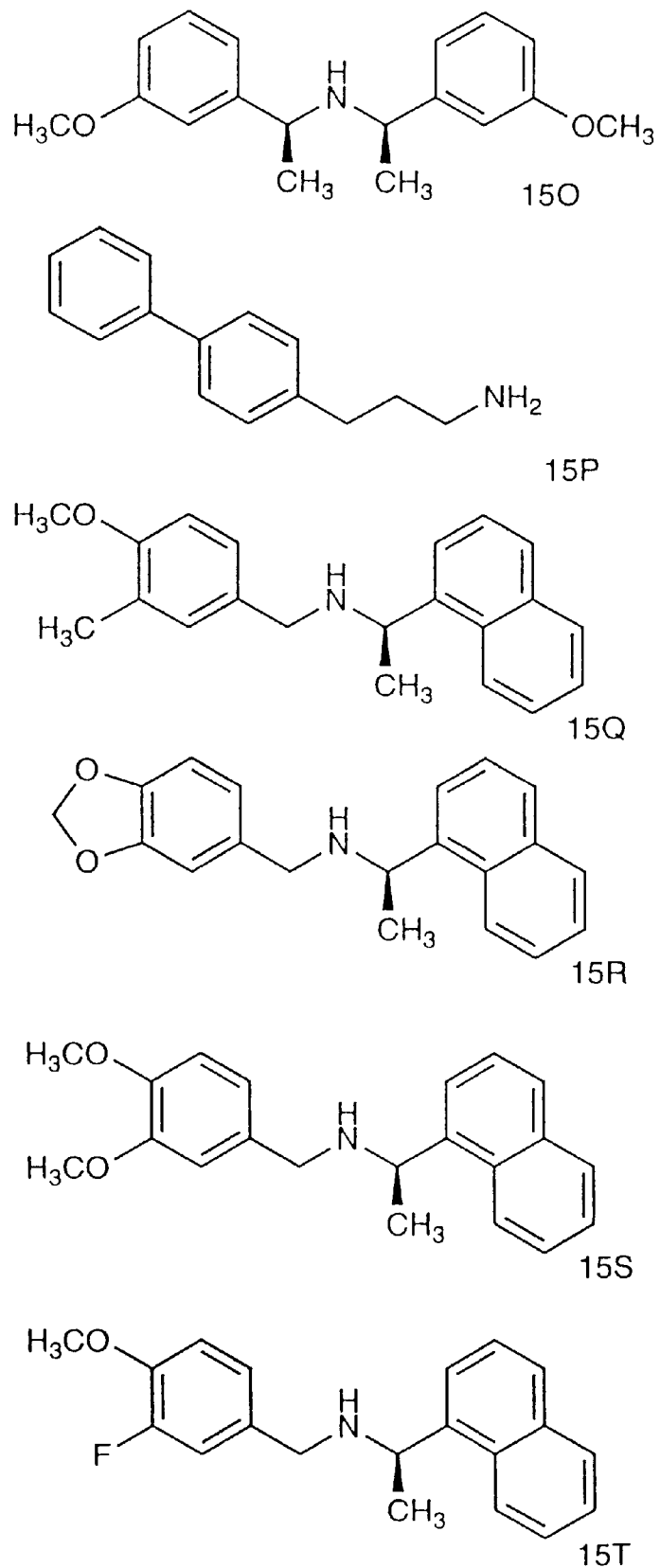
Figures 1, 74:
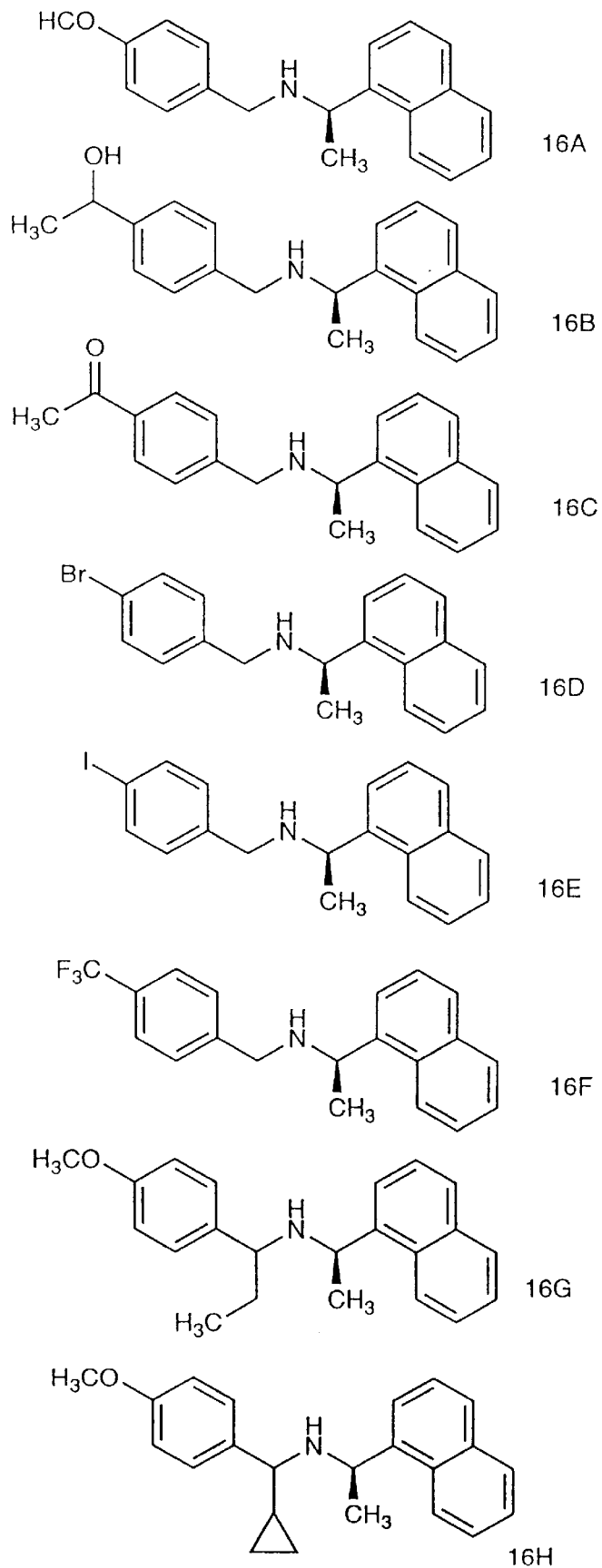
Figures 1, 79:
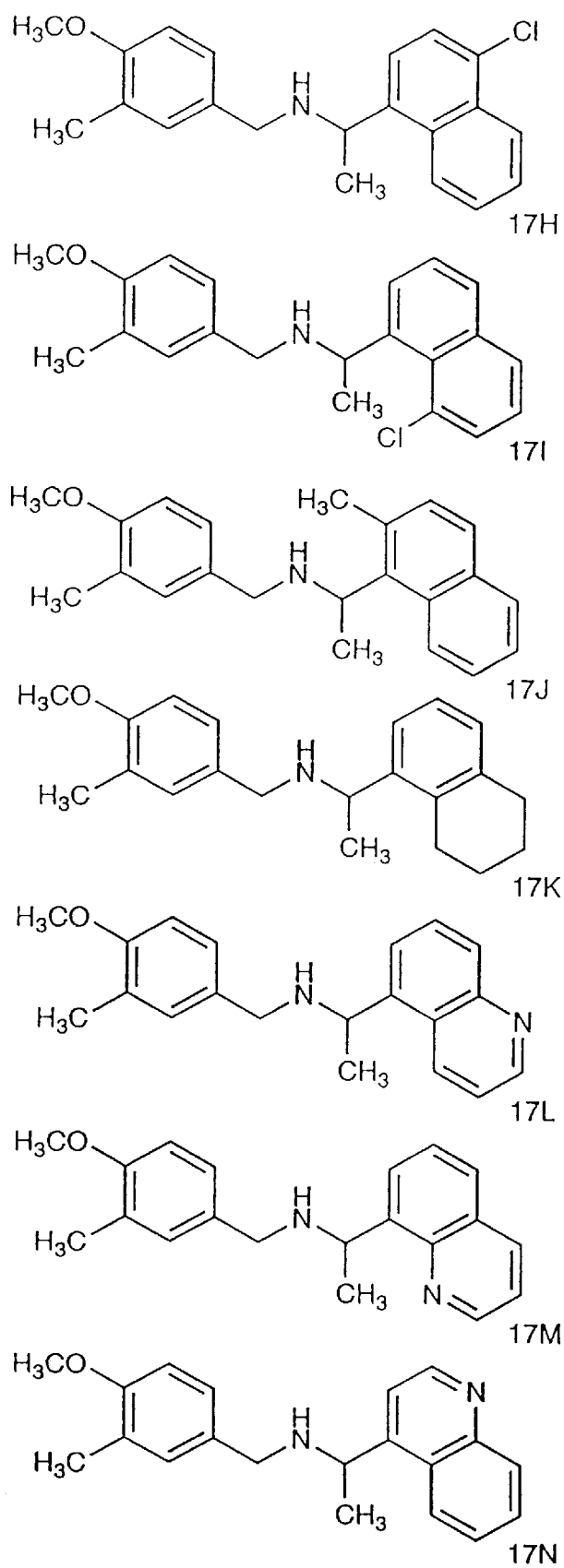
Figure 1:
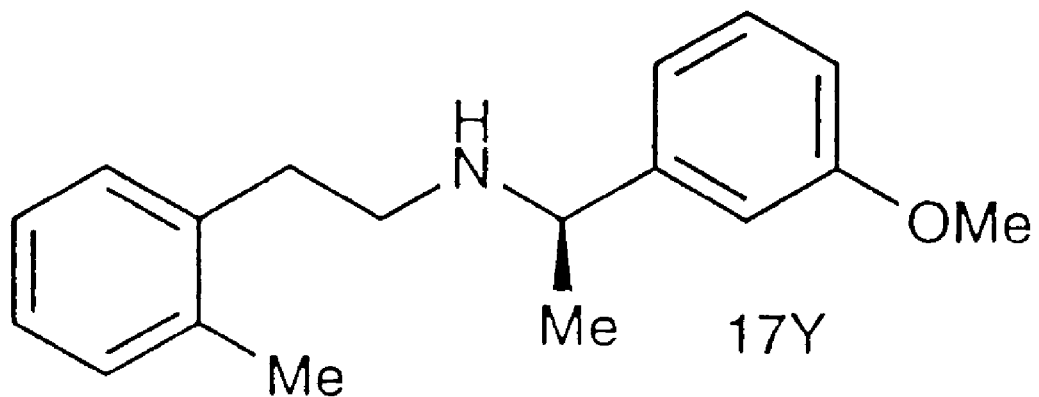
Figure 82:
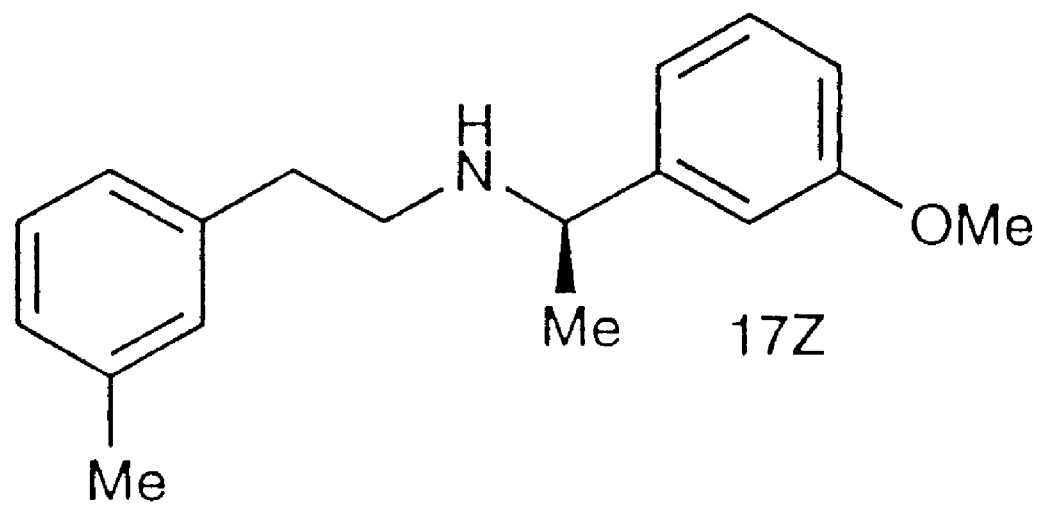
Figures 1, 83:
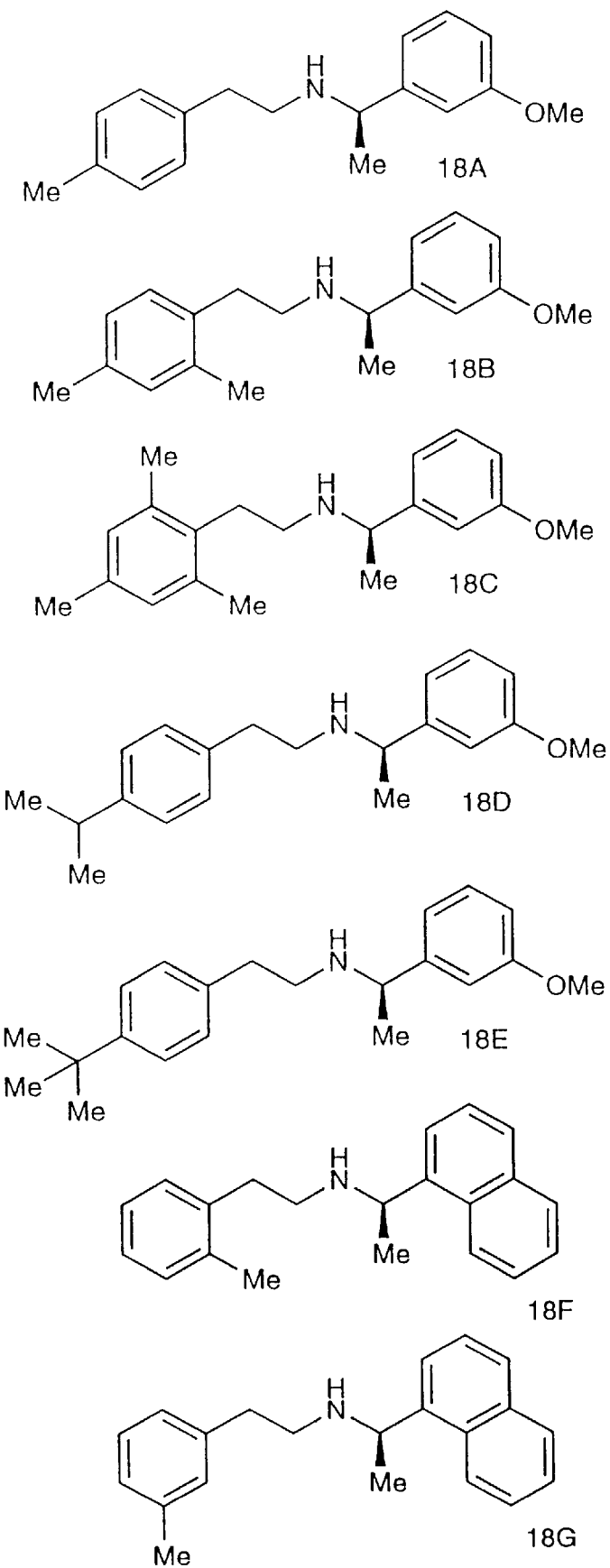
Figures 1, 84:
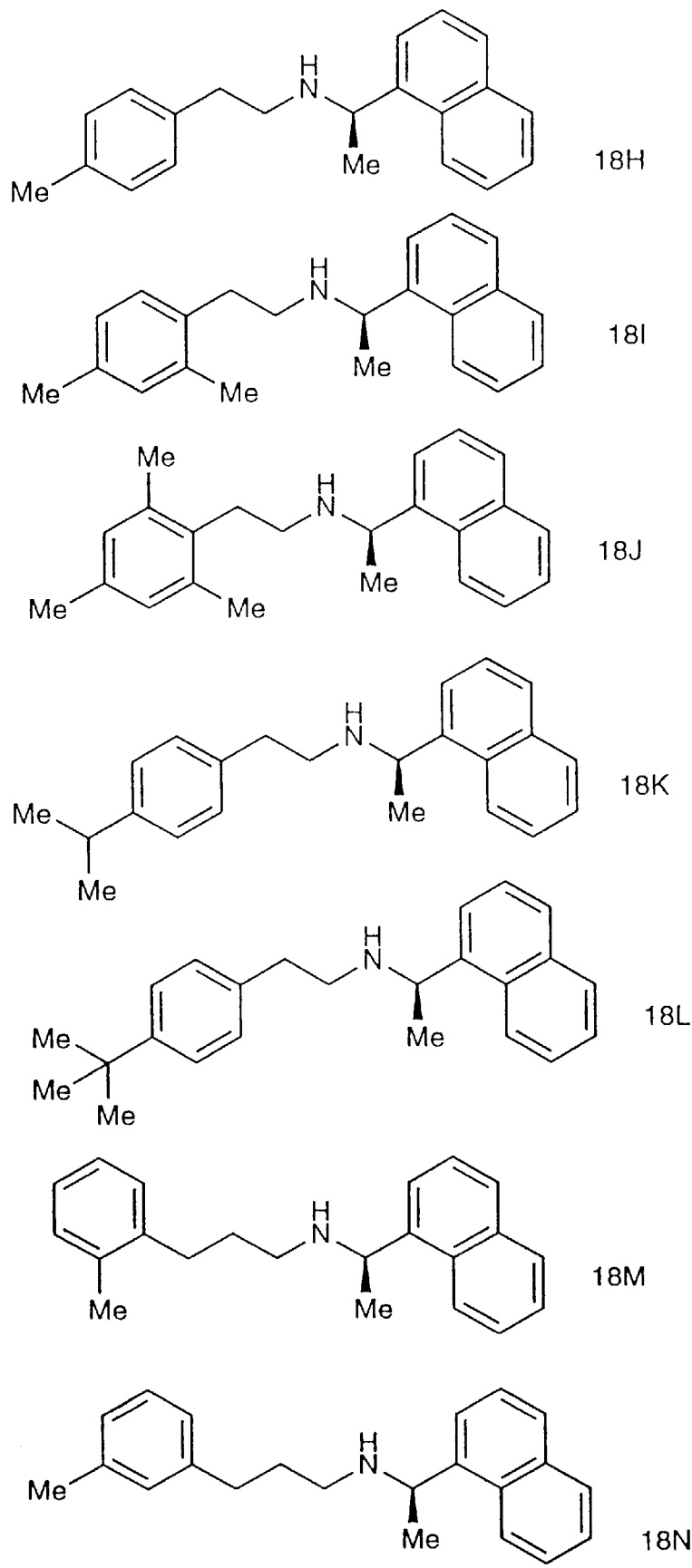
Figure 1:
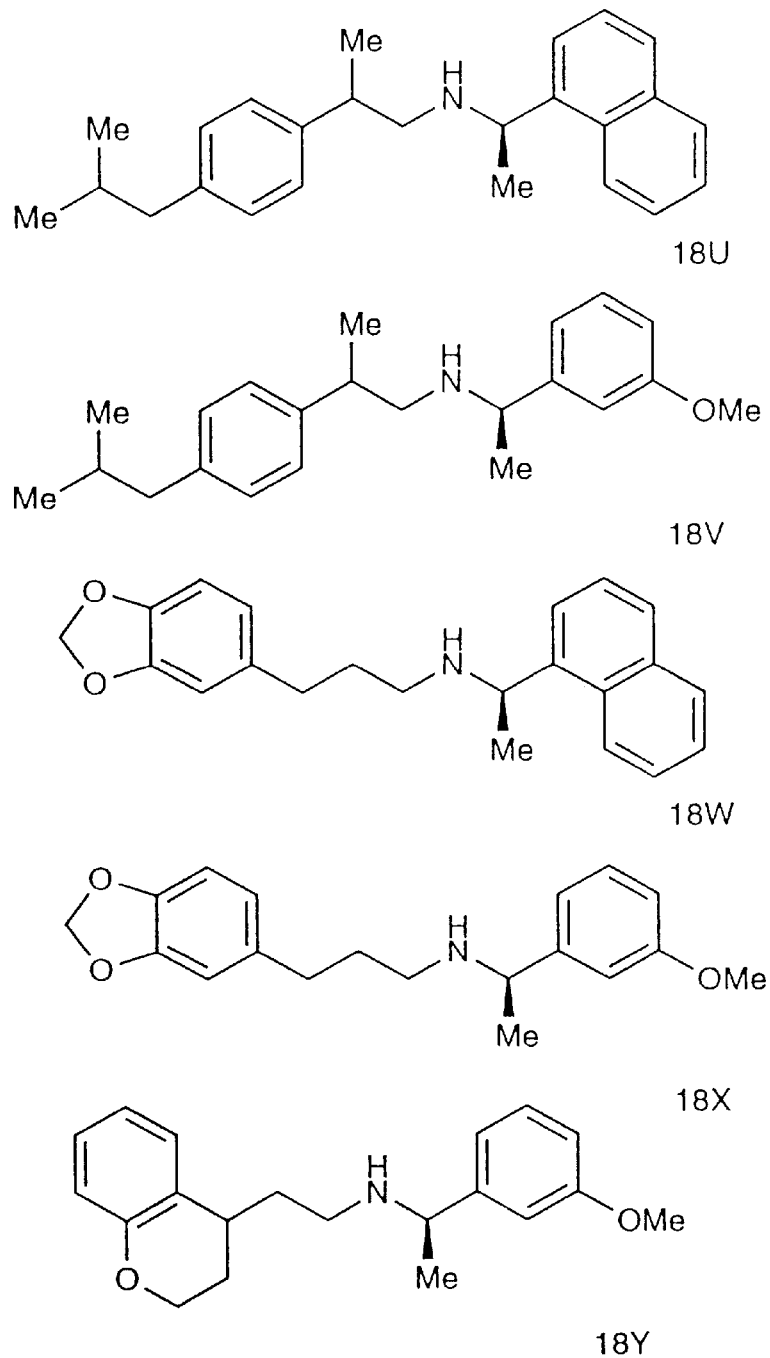
Figure 86:
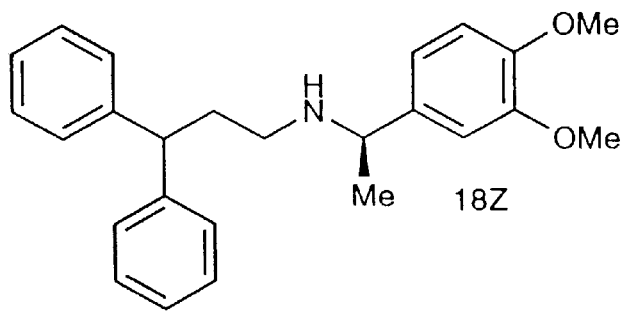
Figures 1, 89:
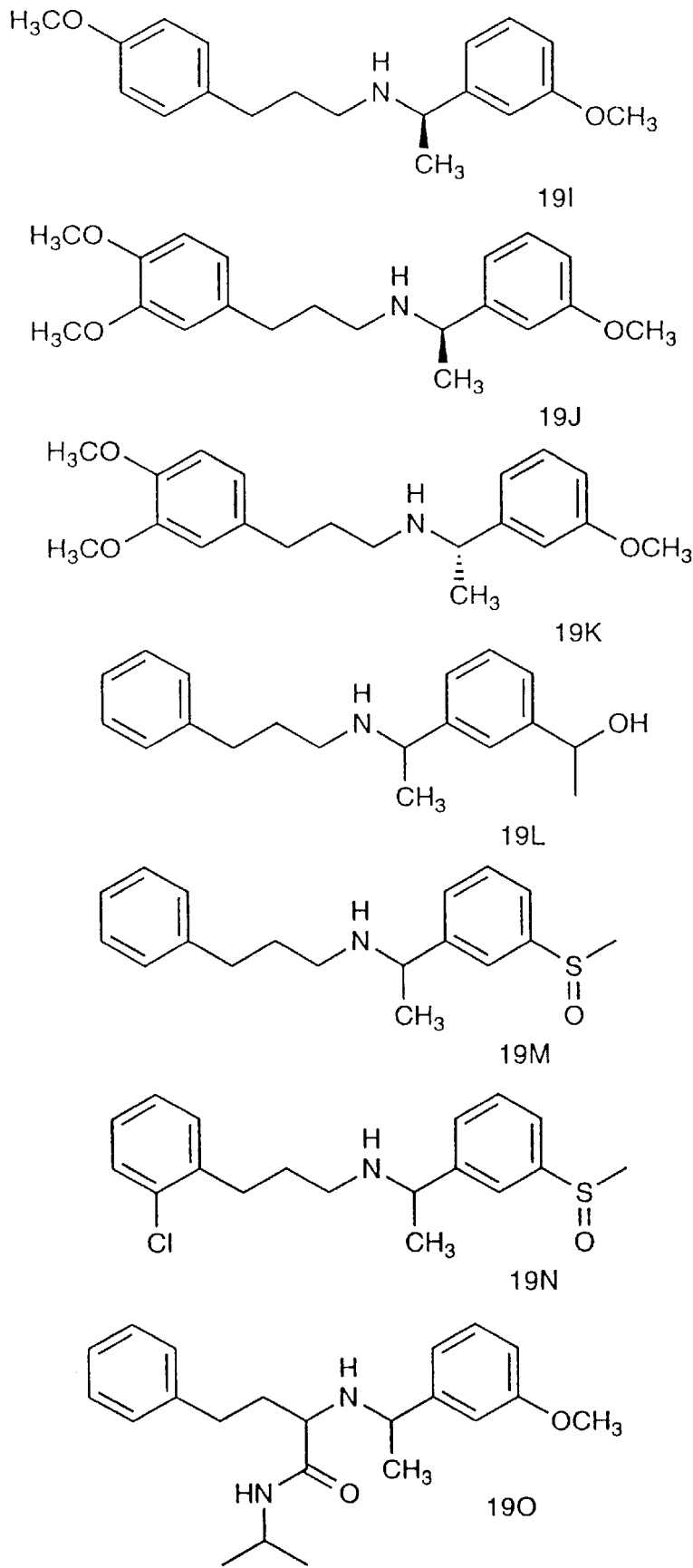

The present invention describes inorganic ion receptor modulating agents able to mimic or block an effect of an inorganic ion at an inorganic ion receptor. The preferred use of inorganic ion receptor modulating agents is to treat a disease or disorder by modulating inorganic ion receptor activity. Preferably, the molecules are used to treat diseases or disorders characterized by abnormal ion homeostasis, more preferably abnormal calcium homeostasis. Other uses of inorganic ion receptor modulating agents, such as diagnostics uses, are known in the art. Nemeth et al., PCT/US93/01642, International Publication Number WO 94/18959.

I. CALCIUM RECEPTORS

Calcium receptors and nucleic acid encoding calcium receptors are described by Nemeth et al., PCT/US93/01642, International Publication Number WO 94/18959. Calcium receptors are present on different cell types such as parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. The calcium receptor on these cell types may be different. It is also possible that a cell can have more than one type of calcium receptor.

Comparison of calcium receptor activities and amino acid sequences from different cells indicate that distinct calcium receptor types exist. For example, calcium receptors can respond to a variety of di- and trivalent cations. The parathyroid calcium receptor responds to calcium and $Gd^{3+}$, while osteoclasts respond to divalent cations such as calcium but does not respond to $Gd^{3+}$. Thus, the parathyroid calcium receptor is pharmacologically distinct from calcium receptor on the osteoclast.

On the other hand, the nucleic acid sequences encoding calcium receptors present in parathyroid cells and C-cells indicate that these receptors have a very similar amino acid structure. Nevertheless, calcimimetic compounds exhibit differential pharmacology and regulate different activities at parathyroid cells and C-cells. Thus, pharmacological properties of calcium receptors may vary significantly depending upon the cell type or organ in which they are expressed even though the calcium receptors may have similar structures.

Calcium receptors, in general, have a low affinity for extracellular $Ca^{2+}$ (apparent $K_d$ generally greater than about 0.5 mM). Calcium receptors may include a free or bound effector mechanism as defined by Cooper, Bloom and Roth, "The Biochemical Basis of Neuropharmacology", Ch. 4, and are thus distinct from intracellular calcium receptors, e.g., calmodulin and the troponins.

Calcium receptors respond to changes in extracellular calcium levels. The exact changes depend on the particular receptor and cell line containing the receptor. For example, the in vitro effect of calcium on the calcium receptor in a parathyroid cell include the following:

1. An increase in internal calcium. The increase is due to the influx of external calcium and/or mobilization of internal calcium. Characteristics of the increase in internal calcium include the following:
   (a) A rapid (time to peak <5 seconds) and transient increase in $[Ca^{2+}]$ that is refractory to inhibition by 1 μM $La^{3+}$ or 1 μM $Gd^{3+}$ and is abolished by pretreatment with ionomycin (in the absence of extracellular $Ca^{2+}$);
   (b) The increase is not inhibited by dihydropyridines;
   (c) The transient increase is abolished by pretreatment for 10 minutes with 10 mM sodium fluoride;
   (d) The transient increase is diminished by pretreatment with an activator of protein kinase C (PKC), such as phorbol myristate acetate (PMA), mezerein or (−)-indolactam V. The overall effect of the protein kinase C activator is to shift the concentration-response curve to calcium to the right without affecting the maximal response; and
   (e) Treatment with pertussis toxin (100 ng/ml for >4 hours) does not affect the increase.
2. A rapid (<30 seconds) increase in the formation of inositol-1,4,5-triphosphate or diacylglycerol. Treatment with pertussis toxin (100 ng/ml for >4 hours) does not affect this increase;

3. The inhibition of dopamine- and isopro-terenol-stimulated cyclic AMP formation. This effect is blocked by pretreatment with pertussis toxin (100 ng/ml for >4 hours); and
4. The inhibition of PTH secretion. Treatment with pertussis toxin (100 ng/ml for >4 hours) does not affect the inhibition in PTH secretion.

Using techniques known in the art, the effect of calcium on other calcium receptors in different cells can be readily determined. Such effects may be similar in regard to the increase in internal calcium observed in parathyroid cells. However, the effect is expected to differ in other aspects, such as causing or inhibiting the release of a hormone other than parathyroid hormone.

II. INORGANIC ION RECEPTOR MODULATING AGENTS

Inorganic ion receptor modulating agents either evokes one or more inorganic ion receptor activities, or blocks one or more inorganic ion receptor activities caused by an extracellular inorganic ion. Calcium receptor modulating agents can mimic or block an effect of extracellular $Ca^{2+}$ on a calcium receptor. Preferred calcium receptor modulating agents are calcimimetics and calcilytics. Generic and specific structures of inorganic ion receptor modulating agents are provided in the Summary supra, and in FIG. 1.

Inorganic ion receptor modulating agents can be identified by screening molecules which are modelled after a molecule shown to have a particular activity (i.e., a lead molecule). Nemeth et al., PCT/US93/01642, International Publication Number WO 94/18959.

Preferred inorganic ion receptor modulation agents described by the present invention are compounds are 8J, 8U, 9R, 11X, 12U, 12V, 12Z, 14U, 16M, and 16P. These compounds all have $EC_{50}$ values of less than 5 $\mu$M.

The $EC_{50}$ is the concentration of the molecule which evokes a half-maximal effect. The $IC_{50}$ is the concentration of molecule which causes a half-maximal blocking effect. The $EC_{50}$ or $IC_{50}$ can be determined by assaying one or more of the activities of an inorganic ion at an inorganic ion receptor. Preferably, such assays are specific to a particular calcium receptor. For example, assays which measure hormones whose production or secretion is modulated by a particular inorganic ion receptor are preferred.

Increases in $[Ca^{2+}]_i$ can be detected using standard techniques such as by using fluorimetric indicators or by measuring an increase in $Cl^-$ current in a Xenopus oocyte injected with nucleic acid coding for a calcium receptor. Nemeth et al., PCT/US93/01642, International Publication Number WO 94/18959. For example, poly(A)$^+$ mRNA can be obtained from cells expressing a calcium receptor, such as a parathyroid cell, bone osteoclast, juxtaglomerular kidney cell, proximal tubule kidney cell, distal tubule kidney cell, cell of the thick ascending limb of Henle's loop and/or collecting duct, keratinocyte in the epidermis, parafollicular cell in the thyroid (C-cell), intestinal cell, central nervous cell, peripheral nervous system cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. Preferably, the nucleic acid is from a parathyroid cell, C-cell, or osteoclast. More preferably, the nucleic acid encodes a calcium receptor and is present on a plasmid or vector.

Preferably, the molecule is either a calcimimetic or calcilytic having an $EC_{50}$ or $IC_{50}$ at a calcium receptor of less than or equal to 5 $\mu$M, and even more preferably less than or equal to 1 $\mu$M, 100 nmolar, 10 nmolar, or 1 nmolar. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness.

In preferred embodiments the calcium receptor modulating agent is a calcimimetic which inhibits parathyroid hormone secretion from a parathyroid cell in vitro and decreases PTH secretion in vivo; stimulates calcitonin secretion from a C-cell in vitro and elevates calcitonin levels in vivo; or blocks osteoclastic bone resorption in vitro and inhibits bone resorption in vivo.

In another preferred embodiment the calcium receptor modulating agent is a calcilytic which evokes the secretion of parathyroid hormone from parathyroid cells in vitro and elevates the level of parathyroid hormone in vivo.

Preferably, the agent selectively targets inorganic ion receptor activity, more preferably calcium receptor activity, in a particular cell. By "selectively" is meant that the molecule exerts a greater effect on inorganic ion receptor activity in one cell type than at another cell type for a given concentration of agent. Preferably, the differential effect is 10-fold or greater. Preferably, the concentration refers to blood plasma concentration and the measured effect is the production of extracellular messengers such as plasma calcitonin, parathyroid hormone or plasma calcium. For example, in a preferred embodiment, the agent selectively targets PTH secretion over calcitonin secretion.

In another preferred embodiment, the molecule has an $EC_{50}$ or $IC_{50}$ less than or equal to 5 $\mu$M at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, peripheral nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

Preferably, inorganic ion receptor modulating agents mimic or block all of the effects of extracellular ion in a cell having an inorganic ion receptor. For example, calcium receptor modulating agents preferably mimic or block all of the effects of extracellular ion in a cell having a calcium receptor. Calcimimetics need not possess all the biological activities of extracellular $Ca^{2+}$, but, rather, at least one such activity is mimicked. Similarly, calcilytics need not reduce or prevent all of the activities caused by extracellular calcium. Additionally, different calcimimetics and different calcilytics do not need to bind to the same site on the calcium receptor as does extracellular $Ca^{2+}$ to exert their effects.

A. Calcimimetics

The ability of molecules to mimic or block the activity of $Ca^{2+}$ at calcium receptors can be determined using procedures known in the art and described by Nemeth et al., PCT/US93/01642, International Publication Number WO 94/18959. For example, calcimimetics possess one or more and preferably all of the following activities when tested on parathyroid cells in vitro:

1. The molecule causes a rapid (time to peak <5 seconds) and transient increase in $[Ca^{2+}]_i$ that is refractory to inhibition by 1 μM $La^{3+}$ or 1 μM $Gd^{3+}$. The increase in $[Ca^{2+}]$ persists in the absence of extracellular $Ca^{2+}$ but is abolished by pretreatment with ionomycin (in the absence of extracellular $Ca^{2+}$);

2. The molecule potentiates increases in $[Ca^{2+}]_i$ elicited by submaximal concentrations of extracellular $Ca^{2+}$;
3. The increase in $[Ca^{2+}]_i$ elicited by extracellular $Ca^{2+}$ is not inhibited by dihydropyridines;
4. The transient increase in $[Ca^{2+}]_i$ caused by the molecule is abolished by pretreatment for 10 minutes with 10 mM sodium fluoride;
5. The transient increase in $[Ca^{2+}]_i$ caused by the molecule is diminished by pretreatment with an activator of protein kinase C (PKC), such as phorbol myristate acetate (PMA), mezerein or (−)-indolactam V. The overall effect of the protein kinase C activator is to shift the concentration-response curve of the molecule to the right without affecting the maximal response;
6. The molecule causes a rapid (<30 seconds) increase in the formation of inositol-1,4,5-triphosphate and/or diacylglycerol;
7. The molecule inhibits dopamine- or isopro-terenol-stimulated cyclic AMP formation;
8. The molecule inhibits PTH secretion;
9. Pretreatment with pertussis toxin (100 ng/ml for >4 hours) blocks the inhibitory effect of the molecule on cyclic AMP formation but does not effect increases in $[Ca^{2+}]_i$, inositol-1,4,5-triphosphate, or diacylglycerol, nor decreases in PTH secretion;
10. The molecule elicits increases in $Cl^-$ current in Xenopus oocytes injected with poly $(A)^+$-enriched mRNA from bovine or human parathyroid cells, but is without effect in Xenopus oocytes injected with water, or rat brain or liver mRNA; and
11. Similarly, using a cloned calcium receptor from a parathyroid cell, the molecule will elicit a response in Xenopus oocytes injected with the specific cDNA or mRNA encoding the receptor.

Different calcium activities can be measured using available techniques. Nemeth et al., PCT/US93/01642, International Publication Number WO 94/18959. Parallel definitions of molecules mimicking $Ca^{2+}$ activity on other calcium responsive cell, preferably at a calcium receptor, are evident from the examples provided herein and Nemeth et al., PCT/US93/01642, International Publication Number WO 94/18959.

Preferably, the agent as measured by the bioassays described herein, or by Nemeth et al., PCT/US93/01642, International Publication Number WO 94/18959, has one or more, more preferably all of the following activities: evokes a transient increase in internal calcium, having a duration of less that 30 seconds (preferably by mobilizing internal calcium); evokes a rapid increase in $[Ca^{2+}]_i$, occurring within thirty seconds; evokes a sustained increase (greater than thirty seconds) in $[Ca^{2+}]_i$ (preferably by causing an influx of external calcium); evokes an increase in inositol-1,4,5-triphosphate or diacylglycerol levels, preferably within less than 60 seconds; and inhibits dopamine- or isoproterenol-stimulated cyclic AMP formation.

The transient increase in $[Ca^{2+}]_i$ is preferably abolished by pretreatment of the cell for ten minutes with 10 mM sodium fluoride, or the transient increase is diminished by brief pretreatment (not more than ten minutes) of the cell with an activator of protein kinase C, preferably, phorbol myristate acetate (PMA), mezerein or (−) indolactam V.

B. Calcilytics

The ability of a molecule to block the activity of external calcium can be determined using standard techniques. Nemeth et al., PCT/US93/01642, International Publication Number WO 94/18959. For example, molecules which block the effect of external calcium, when used in reference to a parathyroid cell, possess one or more, and preferably all of the following characteristics when tested on parathyroid cells in vitro:

1. The molecule blocks, either partially or completely, the ability of increased concentrations of extracellular $Ca^{2+}$ to:
    (a) increase $[Ca^{2+}]_i$
    (b) mobilize intracellular $Ca^{2+}$,
    (c) increase the formation of inositol-1,4,5-triphosphate,
    (d) decrease dopamine- or isoproterenol-stimulated cyclic AMP formation, and
    (e) inhibit PTH secretion;
2. The molecule blocks increases in $Cl^-$ current in Xenopus oocytes injected with poly$(A)^+$ mRNA from bovine or human parathyroid cells elicited by extracellular $Ca^{2+}$ or calcimimetic compounds, but not in Xenopus oocytes injected with water or liver mRNA;
3. Similarly, using a cloned calcium receptor from a parathyroid cell, the molecule will block a response in Xenopus oocytes injected with the specific cDNA, mRNA or cRNA encoding the calcium receptor, elicited by extracellular $Ca^{2+}$ or a calcimimetic compound.

Parallel definitions of molecules blocking $Ca^{2+}$ activity on a calcium responsive cell, preferably at a calcium receptor, are evident from the examples provided herein and Nemeth et al., PCT/US93/01642, International Publication Number WO 94/18959.

III. TREATMENT OF DISEASES OR DISORDERS

A preferred use of the compounds described by the present invention is in the treatment or prevention of different diseases or disorders by modulating inorganic ion receptor activity. The inorganic ion receptor modulating agents of the present invention can exert an affect on a inorganic ion receptor causing one or more cellular effects ultimately producing a therapeutic effect.

Different diseases and disorders can be treated by the present invention by targeting cells having an inorganic ion receptor, such as a calcium receptor. For example, primary hyperparathyroidism (HPT) is characterized by hypercalcemia and elevated levels of circulating PTH. A defect associated with the major type of HPT is a diminished sensitivity of parathyroid cells to negative feedback regulation by extracellular $Ca^{2+}$. Thus, in tissue from patients with primary HPT, the "set-point" for extracellular $Ca^{2+}$ is shifted to the right so that higher than normal concentrations of extracellular $Ca^{2+}$ are required to depress PTH secretion. Moreover, in primary HPT, even high concentrations of extracellular $Ca^{2+}$ often depress PTH secretion only partially. In secondary (uremic) HPT, a similar increase in the set-point for extracellular $Ca^{2+}$ is observed even though the degree to which $Ca^{2+}$ suppresses PTH secretion is normal. The changes in PTH secretion are paralleled by changes in $[Ca^{2+}]_i$: the set-point for extracellular $Ca^{2+}$-induced increases in $[Ca^{2+}]_i$ is shifted to the right and the magnitude of such increases is reduced.

Molecules that mimic the action of extracellular $Ca^{2+}$ are beneficial in the long-term management of both primary and secondary HPT. Such molecules provide the added impetus required to suppress PTH secretion which the hypercalcemic condition alone cannot achieve and, thereby, help to relieve the hypercalcemic condition. Molecules with greater efficacy than extracellular $Ca^{2+}$ may overcome the apparent nonsuppressible component of PTH secretion which is particularly troublesome in adenomatous tissue. Alternatively or additionally, such molecules can depress synthesis of PTH, as prolonged hypercalcemia has been shown to depress the levels of preproPTH mRNA in bovine and human adenomatous parathyroid tissue. Prolonged hypercalcemia also depresses parathyroid cell proliferation in vitro, so calcimimetics can also be effective in limiting the parathyroid cell hyperplasia characteristic of secondary HPT.

Cells other than parathyroid cells can respond directly to physiological changes in the concentration of extracellular $Ca^{2+}$. For example, calcitonin secretion from parafollicular cells in the thyroid (C-cells) is regulated by changes in the concentration of extracellular $Ca^{2+}$.

Isolated osteoclasts respond to increases in the concentration of extracellular $Ca^{2+}$ with corresponding increases in $[Ca^{2+}]_i$ that arise partly from the mobilization of intracellular $Ca^{2+}$. Increases in $[Ca^{2+}]_i$ in osteoclasts are associated with the inhibition of bone resorption. Release of alkaline phosphatase from bone-forming osteoblasts is directly stimulated by calcium.

Renin secretion from juxtaglomerular cells in the kidney, like PTH secretion, is depressed by increased concentrations of extracellular $Ca^{2+}$. Extracellular $Ca^{2+}$ causes the mobilization of intracellular $Ca^{2+}$ in these cells. Other kidney cells respond to calcium as follows: elevated $Ca^{2+}$ inhibits formation of $1,25(OH)_2$-vitamin D by proximal tubular cells, stimulates production of calcium-binding protein in distal tubular cells, and inhibits tubular reabsorption of $Ca^{2+}$ and $Mg^{2+}$ and the action of vasopressin on the medullary thick ascending limb of Henle's loop (MTAL), reduces vasopressin action in the cortical collecting duct cells, and affects vascular smooth muscle cells in blood vessels of the renal glomerulus.

Calcium also promotes the differentiation of intestinal goblet cells, mammary cells, and skin cells; inhibits atrial natriuretic peptide secretion from cardiac atria; reduces CAMP accumulation in platelets; alters gastrin and glucagon secretion; acts on vascular smooth muscle cells to modify cell secretion of vasoactive factors; and affects cells of the central nervous system and peripheral nervous system.

Thus, there are sufficient indications to suggest that $Ca^{2+}$, in addition to its ubiquitous role as an intracellular signal, also functions as an extracellular signal to regulate the responses of certain specialized cells. Molecules of this invention can be used in the treatment of diseases or disorders associated with disrupted $Ca^{2+}$ responses in these cells.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIAH), cirrhosis, heart failure, and nephrosis; hypertension; preventing and/or decreasing renal toxicity from cationic antibiotics (e.g., aminoglycoside antibiotics); gut motility disorders such as diarrhea, and spastic colon; GI ulcer diseases; GI absorption diseases such as sarcoidosis; and autoimmune diseases and organ transplant rejection.

While inorganic ion receptor modulating agents of the present invention will typically be used in therapy for human patients, they may be used to treat similar or identical diseases or disorders in other warm-blooded animal species such as other primates, farm animals such as swine, cattle, and poultry; and sports animals and pets such as horses, dogs and cats.

IV. ADMINISTRATION

The molecules of the invention can be formulated for a variety of modes of administration to treat patients by modulating inorganic ion receptor activity. Techniques and formulations for administration of compounds generally may be found in *Remington's Pharmaceutical Sciences,* Mack Publishing Co., Easton, PA. Administration of ionmimetics and ionlytics is discussed by Nemeth et al., PCT/US93/01642, International Publication Number WO 94/18959.

Suitable forms, in part, depend upon the use or the route of entry, for example oral, transdermal, or by injection. Such forms should allow the agent to reach a target cell whether the target cell is present in a multicellular host or in culture. For example, pharmacological agents or compositions injected into the blood stream should be soluble in the concentrations used. Other factors are known in the art, and include considerations such as toxicity and forms which prevent the agent or composition from exerting its effect.

Agents can also be formulated as pharmaceutically acceptable salts (e.g., acid addition salts,) and complexes thereof. The preparation of such salts can facilitate the pharmacological use by altering the physical characteristics of the agent without preventing it from exerting its physiological effect. Examples of useful alterations in physical properties include lowering the melting point to facilitate transmucosal administration and increasing the solubility to facilitate administering higher concentrations of the drug.

For systemic administration, oral administration is preferred. Alternatively, injection may be used, e.g., intramuscular, intravenous, intraperitoneal, and subcutaneous. For injection, the molecules of the invention are formulated in liquid solutions, preferably in physiologically compatible buffers such as Hank's solution or Ringer's solution. In addition, the molecules may be formulated in solid form and redissolved or suspended immediately prior to use. Lyophilized forms can also be produced.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays, for example, or using suppositories. For oral administration, the molecules are formulated into conventional oral administration dosage forms such as capsules, tablets, and tonics.

For topical administration, the molecules of the invention are formulated into ointments, salves, gels, or creams, as is generally known in the art.

Generally, a therapeutically effective amount is between about 1 nmole and 3 μmole of the molecule, preferably 0.1 nmole and 1 μmole depending on its $EC_{50}$ or $IC_{50}$ and on the age and size of the patient, and the disease or disorder associated with the patient. Generally it is an amount between about 0.1 and 50 mg/kg, preferably 0.01 and 20 mg/kg, animal to be treated.

V. EXAMPLES

The compounds described herein can be synthesized using standard techniques such as those described by Nemeth et al., PCT/US93/01642, International Publication Number WO 94/18959. Examples describing the syntheses of compounds 4L, 8J, 8U, 9R, 11X, 12U, 12V, 12Z, 14U, 16M and 16P are provided below. Compounds 4L, 8J, 8U, 11X and 16M were prepared from the condensation of a primary amine with an aldehyde or ketone in the presence of titanium (IV) isopropoxide. The resulting intermediate imines were then reduced in situ by the action of sodium cyanoborohydride, sodium borohydride, or sodium triacetoxyborohydride. The intermediate enamine for the synthesis of compound 8U was catalytically reduced using palladium hydroxide.

Synthesis of compounds 9R, 14U, and 16P were prepared by reductive amination of a commercially available aldehyde or ketone with a primary amine in the presence of sodium cyanoborohydride or sodium triacetoxyborohydride. It was found for the syntheses of these three compounds (9R, 14U, and 16P) that sodium triacetoxyborohydride afforded the desired diastereomers with greater diastereoselectivity than using sodium cyanoborohydride. The enriched mixtures were further purified to a single diastereomer by normal-phase HPLC or by recystallization from organic solvents.

Compounds 12U, 12V and 12Z were prepared by a diisobutylaluminum hydride (DIBAL-H) mediated condensation of an amine with a nitrile. The resulting intermediate imine is reduced in situ by the action of sodium cyanoborohydride or sodium borohydride. The intermediate alkenes (compounds 12U and 12V) were reduced by catalytic hydrogenation in EtOH using palladium on carbon. Compounds which were converted to their corresponding hydrochloride were done so by treatment of the free base with ethereal HCl to afford white solids.

The amines in these syntheses were (1) purchased from Aldrich Chemical Co., Milwaukee, Wis., (2) purchased from Celgene Corp., Warren, N.J., or (3) prepared synthetically using standard techniques. All other reagent chemicals were purchased from Aldrich Chemical Co.

Example 1

Synthesis of Compound 4L

N-3-Phenyl-1-propyl-1-(1-naphthyl)ethylamine

A mixture of 3-phenyl-1-propylamine (135 mg, 1 mmol), 1'-acetonaphthone (170 mg, 1 mmol), and titanium (IV) isopropoxide (355 mg, 1.3 mmol) was stirred at room temperature for 1 hour. The reaction was treated with 1 M ethanolic sodium cyanoborohydride (1 mL) and stirred at room temperature for 16 hours. The reaction was diluted with ether and treated with water (0.1 mL). The reaction was centrifuged and the ether layer removed and concentrated to a milky oil. A small portion of this material (10 mg) was purified by HPLC (Phenomenex, 1.0×25 cm, 5 μM silica) using a gradient of dichloromethane to 10% methanol in dichloromethane containing 0.1% isopropylamine. This afforded the product (free base) as a single component by GC/EI-MS ($R_t$=10.48 min) m/z (rel. int.) 289 ($M^+$,11), 274 (63), 184 (5), 162 (5), 155 (100), 141 (18), 115 (8), 91 (45), 77(5).

Example 2

Synthesis of Compound 8J

N-(3-phenylpropyl)-1-(3-thiomethylphenyl)ethylamine hydrochloride

3'-Aminoacetophenone (2.7 g, 20 mmol) was dissolved in 4 mL of concentrated HCl, 4 g of ice and 8 mL of water. The solution was cooled to 0° C., and sodium nitrite (1.45 g, 21 mmol) dissolved in 3–5 mL of water was added over 5 minutes while maintaining the temperature below 6° C. Sodium thiomethoxide (1.75 g, 25 mmol) was dissolved in 5 mL of water and cooled to 0° C. To this solution was added the diazonium salt over 10 minutes while maintaining the temperature below 10° C. The reaction was stirred for an additional hour while allowing the temperature to rise to ambient. The reaction mixture was partitioned between ether and water. The ether layer was separated and washed with sodium bicarbonate and sodium chloride, and dried over sodium sulfate. The ether was evaporated to give a 74% yield of 3'-thiomethylacetophenone. The crude material was purified by distillation at reduced pressure.

3-Phenylpropylamine (0.13 g, 1 mmol), 3'-thiomethylacetophenone (0.17 g, 1 mmol), and titanium (IV) isopropoxide (0.36 g, 1.25 mmol) were mixed together and allowed to stand for 4 hours. Ethanol (1 mL) and sodium cyanoborohydride (0.063 g, 1 mmol) were added and the reaction was stirred overnight. The reaction was worked up by the addition of 4 mL of ether and 200 μL of water. The mixture was vortexed and then spun in a centrifuge to separate the solids. The ether layer was separated from the precipitate, and the solvent removed in vacuo. The oil was redissolved in dichloromethane and the compound purified by preparative TLC on silica gel eluted with 3% methanol/dichloromethane to yield the title compound as a pure oil: GC/EI-MS($R_t$=7.64 min) m/z (rel. int.)285 ($M^+$, 18), 270 (90), 180(17), 151(100), 136(32), 104(17), 91(54), 77(13).

Example 3

Synthesis of Compound 8U

N-3-(2-methoxyphenyl)-1-propyl-(R)-3-methoxy-α-methylbenzylamine hydrochloride

A mixture of (R)-(+)-3-methoxy-α-methylbenzylamine (3.02 g, 20 mmol), 2-methoxycinnamaldehyde (3.24 g, 20 mmol), and titanium (IV) isopropoxide (8.53 g, 30 mmol, 1.5 Eq.) was stirred 2 hours at room temperature and treated with 1 M (20 mL) ethanolic sodium cyanoborohydride. The reaction was stirred overnight (16 hours), diluted with diethylether, and treated with water (1.44 mL, 80 mmol, 4 Eq.). After mixing for 1 hour the reaction mixture was centrifuged and the ether layer removed and concentrated to an oil. This material was dissolved in glacial acetic acid, shaken with palladium hydroxide and hydrogenated under 60 p.s.i. hydrogen for 2 hours at room temperature. The catalyst was removed by filtration and the resulting solution concentrated to a thick oil. This material was dissolved in dichloromethane and neutralized with 1 N NaOH. The dichloromethane solution was separated from the aqueous phase, dried over anhydrous potassium carbonate and concentrated to an oil. This material was dissolved in ether and treated with 1 M HCl in diethylether. The resulting precipitate (white solid) was collected, washed with diethylether, and air dried. GC/El-MS ($R_t$=9.69 min) of this material (free base) showed a single component: m/z (rel. int.) 299 ($M^+$, 21), 284 (100), 164 (17), 150 (8), 135 (81), 121 (40), 102 (17), 91 (43), 77 (18).

Example 4

Synthesis of Compound 9R
(R)-N-(1-(2-naphthyl)ethyl)-(R)-1-(1-naphthyl)ethylamine hydrochloride A mixture of (R)-(+)-1-(1-naphthyl)ethylamine (10.0 g, 58 mmol), 2'-acetonaphthone (9.4 g, 56 mmol), titanium (IV) isopropoxide (20.7 g, 73.0 mmol), and EtOH (abs.) (100 mL) was heated to 60° C. for 3 hours. Sodium cyanoborohydride ($NaCNBH_3$) (3.67 g, 58.4 mmol) was then added. The reaction mixture was stirred at room temperature for 18 hours. Ether (1 L) and $H_2O$ (10 mL) were added to the reaction mixture and the resulting precipitate was then removed by centrifugation. The supernatant was evaporated under vacuum and the crude product was recrystallized four times from hot hexane, to provide 1.5 g of pure (98+ %) diastereomer. The free base was dissolved in hexane, filtered, and then ethereal HCl was added to precipitate the product as a white solid (1.1 g, 6% yield), m.p.: softens 200–240° C. (dec.).

Example 5

Synthesis of Compound 11X
N-(4-Isopropylbenzyl)-(R)-1-(1-naphthyl)ethylamine hydrochloride A mixture of (R)-(+)-1-(1-naphthyl)ethylamine (1.06 g, 6.2 mmol), 4-isopropylbenzaldehyde (0.92 g, 6.2 mmol), and titanium (IV) isopropoxide (2.2 g, 7.7 mmol) was heated to 100° C. for 5 min then allowed to stir at room temperature for 4 hours. Sodium cyanoborohydride ($NaCNBH_3$) (0.39 g, 6.2 mmol) was then added followed by EtOH (1 mL). The reaction mixture was stirred at room temperature for 18 hours. Ether (100 mL) and $H_2O$ (1 mL) were added to the reaction mixture and the resulting precipitate was then removed by centrifugation. The supernatant was evaporated under vacuum and the crude product was chromatographed on silica gel (50 mm×30 cm column) (elution with 1% $MeOH/CHCl_3$). The chromatographed material was then dissolved in hexane and ethereal HCl was added to precipitate the product as a white solid (0.67 g, 35% yield), m.p.; 257–259° C.

Example 6

Synthesis of Compound 12U
N-3-(2-methylphenyl)-1-propyl-(R)-3-methoxy-α-methylbenzylamine hydrochloride A solution of 2-methylcinnamonitrile (1.43 g, 10 mmol) in dichloromethane (10 mL) was cooled to 0° C. and treated dropwise (15 minutes) with 1 M diisobutylaluminum hydride (10 mL, dichloromethane). The reaction was stirred at 0° C. for 15 minutes and treated dropwise (15 minutes) with a 1 M solution of (R)-(+)-3-methoxy-α-methylbenzylamine (1.51 g, 10 mmol) in dichloromethane (10 mL). The reaction was stirred 1 hours at 0° C. and poured into a solution of ethanol (100 mL) containing sodium cyanoborohydride (1 g, 16 mmol). The reaction mixture was stirred 48 hour at room temperature. The reaction was diluted with ether and neutralized with 1 N NaOH. The ether layer was removed, dried over anhydrous potassium carbonate and concentrated to an oil. This material was chromatographed through silica using a gradient of dichloromethane to 5% methanol in dichloromethane to afford the unsaturated intermediate, a single component by GC/El-MS ($R_t$=10.06 min) m/z (rel. int.) 281 ($M^+$,17), 266 (59), 176 (19), 146 (65), 135 (73), 131 (100), 91 (21), 77 (13).

The unsaturated intermediate in ethanol was hydrogenated (1 atm $H_2$) in the presence of palladium on carbon for 16 hours at room temperature. The product from this reaction was converted to the hydrochloride salt by treatment with 1 M HCl in diethylether. GC/El-MS ($R_t$=9.31 min) of this material (free base) showed a single component: m/z (rel. int.) 283 ($M_+$, 21), 268 (100), 164 (12), 148 (8), 135 (85), 121 (12), 105 (49), 91 (23), 77 (21).

Example 7

Synthesis of Compound 12V
N-3-(3-methylphenyl)-1-propyl-(R)-3-methoxy-α-methylbenzylamine hydrochloride The compound was prepared following the procedure described in Example 6, but using 2-methylcinnamonitrile. The unsaturated intermediate was a single component by GC/EI-MS ($R_t$=10.21 min) m/z (rel. int.) 281 ($M^+$, 57), 266 (86), 146 (98), 135 (88), 131 (100), 115 (43), 102 (26), 91 (43), 77 (18). Reduction of this material and hydrochloride formation using the procedure described Example 6 afforded the product. GC/EI-MS ($R_t$=9.18 min) of this material (free base) showed a single component; m/z (rel. int.) 283 ($M^+$, 19), 268 (100), 164 (11), 148 (8), 135 (76), 121 (16), 105 (45), 91 (23), 77 (21).

Example 8

Synthesis of Compound 12Z
N-3-(2-chlorophenyl)-1-propyl-(R)-1-(1-naphthyl)ethylamine hydrochloride The compound was prepared following the procedures described in Example 6, but using 2-chlorohydrocinnamonitrile and (R)-(+)-1-(1-naphthyl)ethylamine on a 10 mmol scale. Chromatography through silica using a gradient of dichloromethane to 5% methanol in dichloromethane afforded the product as a single component by TLC analysis (5% methanol in dichloromethane). The hydrochloride was prepared by treatment with 1 M HCl in diethylether.

Example 9

Synthesis of Compound 14U
(R)-N-(1-(4-methoxyphenyl)ethyl)-(R)-1-(1-naphthyl)ethylamine hydrochloride A mixture of (R)-(+)-1-(1-naphthyl)ethylamine (1.1 g, 6.2 mmol), 4'-methoxyacetophenone (0.93 g, 6.2 mmol), titanium (IV) isopropoxide (2.2 g, 7.7 mmol), and EtOH (abs.) (1 mL) was heated to 60° C. for 3 hours. Sodium cyanoborohydride ($NaCNBH_3$) (0.39 g, 6.2 mmol) was then added, and the reaction mixture was stirred at room temperature for 18 hours. Ether (200 mL) and $H_2O$ (2 mL) were added to the reaction mixture and the resulting precipitate was then removed by centrifugation. The supernatant was evaporated under vacuum and the crude product was chromatographed on silica gel (25 mm×25 cm column) (elution with 1% $MeOH/CHCl_3$). A portion of this material was HPLC chromatographed [Selectosil, 5 μM silica gel; 25 cm×10.0 mm (Phenomenex, Torrance, Calif.), 4 mL per minute; UV det. 275 nM; 12% ethyl acetate-88% hexane (elution time 12.0 min)]. The HPLC purified diastereomer was then dissolved in hexanes and ethereal HCl was added to precipitate the product as a white solid (20 mg), m.p.: 209–210° C.(dec.).

Example 10

Synthesis of Compound 16M
N-(3-chloro-4-methoxybenzyl)-(R)-1-(1-naphthyl)ethylamine hydrochloride A mixture of (R)-(+)-1-(1-naphthyl)ethylamine (6.6 g, 39 mmol), 3'-chloro-4'-methoxybenzaldehyde (6.6 g, 39 mmol), and titanium (IV) isopropoxide (13.8 g, 48.8 mmol), and EtOH (abs.) (30 mL) was heated to 80° C. for 30 minutes then allowed to stir at room temperature for 3 hours. Sodium cyanoborohydride (NaCNBH$_3$) (2.45 g, 39 mmol) was then added. The reaction mixture was stirred at room temperature for 18 hours. Ether (100 mL) and H$_2$O (2 mL) were added to the reaction mixture and the resulting precipitate was then removed by centrifugation. The supernatant was evaporated under vacuum and the crude product was chromatographed on silica gel (50 mm×30 cm column) (elution with CH$_2$Cl$_2$). The chromatographed material was then dissolved in hexane (500 mL), decolorized with Norit® filtered (0.2 μM), and then ethereal HCl was added to precipitate the product as a while solid (10.2 g, 56% yield), m.p.: 241–242° C. (dec.).

Example 11

Synthesis of Compound 16P
4-Methoxy-3-methylacetophenone [16P Precursor]

A mixture of 4'-hydroxy-3'-methylacetophenone (5.0 g, 33.3 mmol), iodomethane (5.7 g, 40.0 mmol), K$_2$CO$_3$ (granular, anhydrous) (23.0 g, 167 mmol), and acetone (250 mL) was refluxed for 3 hours. The reaction mixture was then cooled to room temperature, filtered to remove the inorganic salts, and evaporated under vacuum. The crude product was dissolved in ether (100 mL) and washed with H$_2$O (2×20 mL). The organic layer was dried (Na$_2$SO$_4$) and evaporated to yield 4.5 g, 82.4% yield. The ketone was used in the following reaction without further purification.
(R)-N-(1-(4-Methoxy-3-methylphenyl)ethyl)-(R)-1-(1-naphthyl)ethylamine hydrochloride [Compound 16P]

A mixture of (R)-(+)-1-(1-naphthyl)ethylamine (4.24 g, 24.8 mmol), 4'-methoxy-3'-methylacetophenone (4.06 g, 24.8 mmol), and titanium (IV) isopropoxide(8.8 g, 30.9 mmol), and EtOH (abs.) (1 mL) was heated to 100° C. for 2 hours. Isopropanol (45 mL) was added and the reaction was then cooled to 10° C. in an ice bath. Sodium triacetoxyborohydride (NaHB(O$_2$CCH$_3$)$_3$) (10.5 g, 49.5 mmol) was then added in portions over 15 minutes. The reaction mixture was then heated to 70° C. for 18 hours. The mixture was cooled to room temperature and poured into ether (400 mL). The suspension was centrifuged, the supernatant was collected and the pellet was washed with ether (400 mL). The combined organic washings were evaporated under vacuum. The residue was dissolved in ether (400 mL) and washed with 1 N NaOH (4×50 mL) and H$_2$O (2×50 mL). The organic layer was dried (Na$_2$SO$_4$), filtered and evaporated under vacuum. EtOH (abs.) was added to the wet residue which was then dried thoroughly on a rotary evaporator to provide an oil. The mixture was then chromatographed on silica gel (50 mm×30 cm) [elution with (1% MeOH:1% IPA:CHCl$_3$) to give 4.8 g of an oil].

The desired diastereomer was further purified by HPLC chromatography [SUPELCOSIL™ PLC-Si, 18 μM silica gel; 25 cm×21.2 mm (Supelco, Inc., Bellefonte, Pa.), 7 mL per minute; UV det. 275 nM: 20% EtOAc-80% hexane (elution time 9.5–11.0 min)]. Injections (800 μL aliquots) of the mixture (100 mg/mL solution in eluent) provided 65 mg of the desired isomer. Multiple HPLC injections provided 1.0 g of purified material. The HPLC chromatographed material was dissolved in hexane (50 mL) and the hydrochloride salt was precipitated with ethereal HCl. The salt was collected on fritted glass and washed with hexane to provide 1.0 g of a white solid, mp 204–205° C.

Other embodiments are within the following claims.

We claim:

1. A compound having the formula:

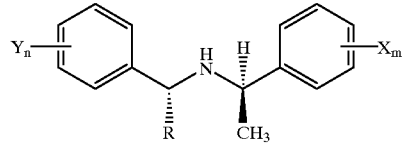

wherein each X and Y independently is selected from the group consisting of CH$_3$, CH$_3$O, CH$_3$CH$_2$O, methylene dioxy made up of two X or two Y, Br, Cl, F, CF$_3$, CHF$_2$, CH$_2$F, CF$_3$O, CH$_3$S, OH, CH$_2$OH, CONH$_2$, CN, NO$_2$, CH$_3$CH$_2$, propyl, isopropyl, butyl, isobutyl, t-butyl, acetoxy, an aliphatic ring, a fused aliphatic ring made up of two X or two Y, an attached aromatic ring, and a fused aromatic ring made up of two X or two Y;

R is selected from the group consisting of hydrogen, methyl, ethyl, propyl, isopropyl, butyl, allyl, isobutyl, t-butyl, cyclopentyl, cyclohexyl, cycloheptyl, cyclooctyl, indenyl, indanyl, dihydroindolyl, thiodihydroindolyl, and 2-, 3-, or 4-piperid(in)yl; and each m and n is independently between 0 and 5 inclusive; provided that two of X together make up a fused phenyl to form a naphthyl which may be substituted;

provided that if R is hydrogen, then Y$_n$ is not 2-hydroxy-3-CH$_3$O, 2-hydroxy-3-CH$_3$CH$_2$O, or 4-hydroxy;

or a pharmaceutically acceptable salt thereof.

2. The compound of claim 1 wherein each X and Y independently is selected from the group consisting of CH$_3$, CH$_3$O, CH$_3$CH$_2$O, methylene dioxy made up of two X or two Y, Br, Cl, F, CF$_3$, CHF$_2$, CH$_2$F, CF$_3$O, CH$_3$S, OH, CH$_2$OH, CONH$_2$, CN, NO$_2$, CH$_3$CH$_2$, propyl, isopropyl, butyl, isobutyl, t-butyl, acetoxy, an aliphatic ring, an attached aromatic ring, and a fused aromatic ring made up of two X or two Y; provided that if n is 1 then Y is a substituent other than hydroxy, alkyl or halogen.

3. The compound of claim 2 wherein R is selected from the group consisting of H, CH$_3$, ethyl, and isopropyl.

4. The compound of claim 3 wherein each Y is independently selected from the group consisting of isopropyl, CH$_3$O, CH$_3$S, CF$_3$O, an aliphatic ring, an attached aromatic ring and a fused aromatic ring made up of two Y.

5. The compound of claim 4, wherein n is 1–5.

6. The compound of claim 5, wherein R is either H or CH$_3$, and n is 2–5.

7. A compound having the chemical formula of either,

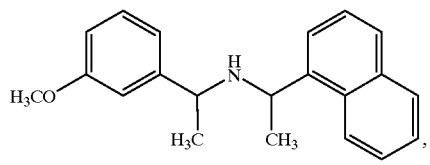

-continued
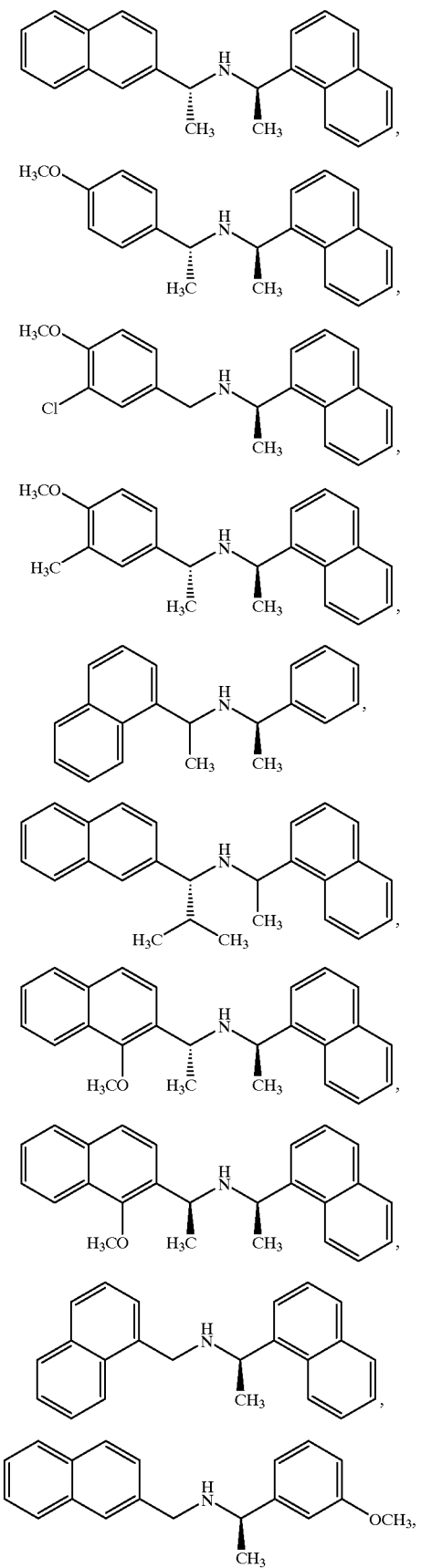
-continued
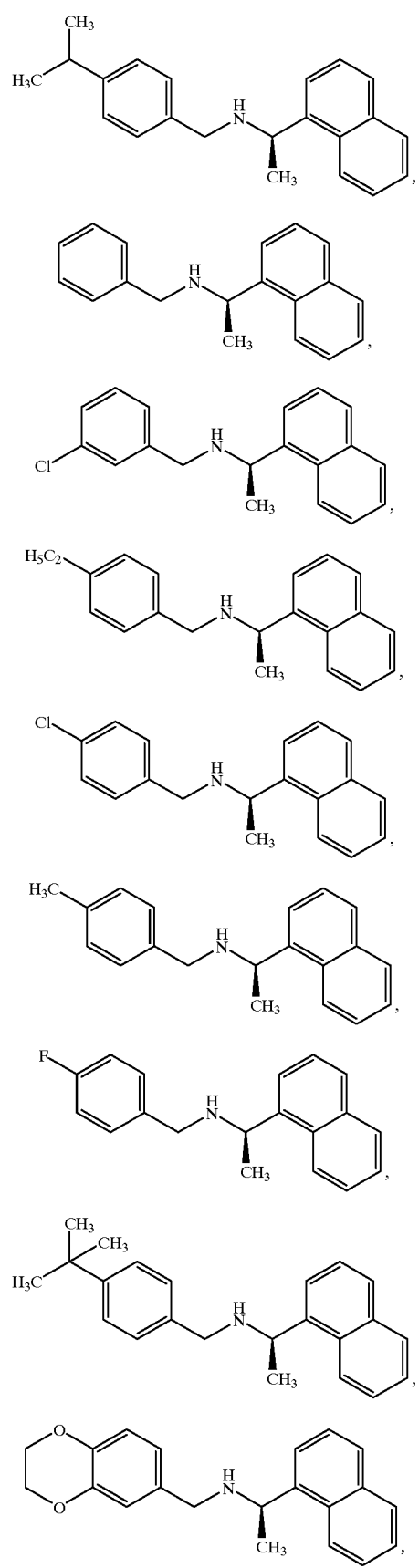

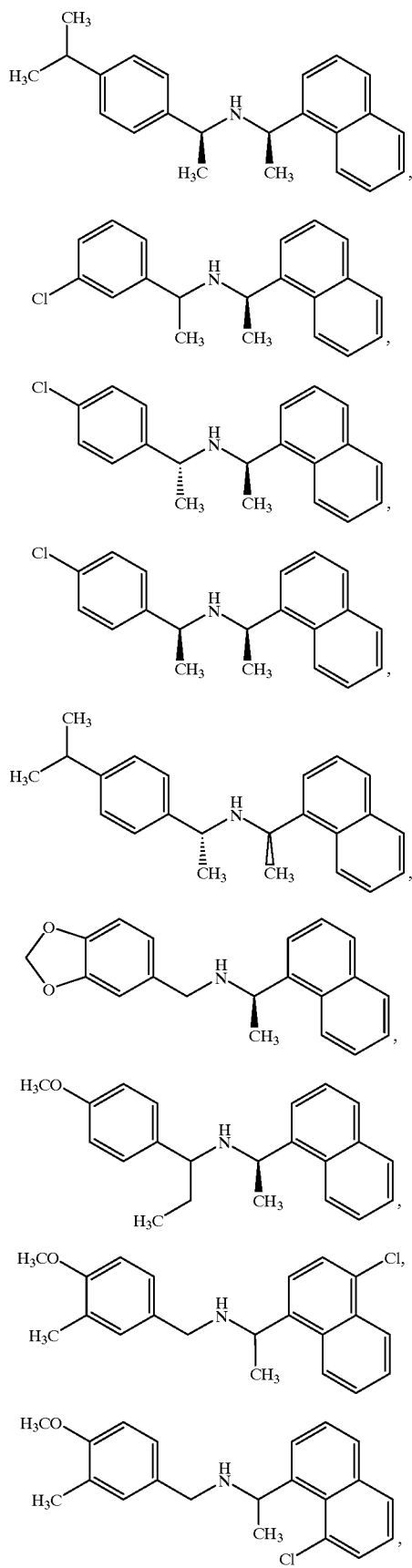
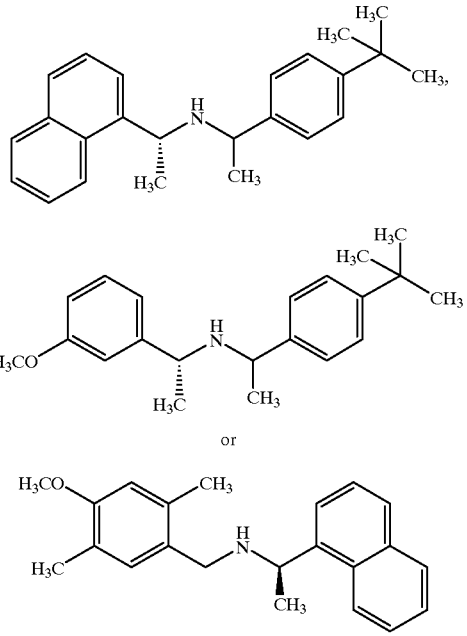
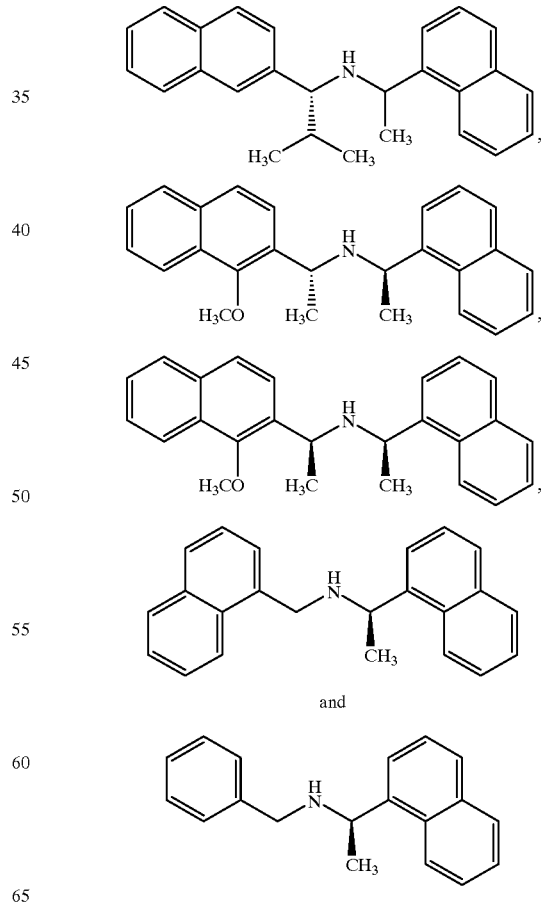
or a pharmaceutically acceptable salt thereof.
8. The compound of claim 7, wherein said compound is selected from the group consisting of
or a pharmaceutically acceptable salt thereof.

9. The compound of claim 7, wherein said compound is

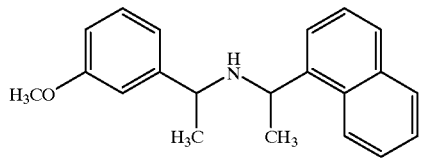

or a pharmaceutically acceptable salt thereof.

10. The compound of claim 7, wherein said compound is

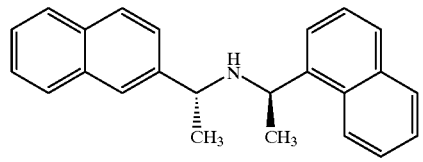

or a pharmaceutically acceptable salt thereof.

11. The compound of claim 7, wherein said compound is

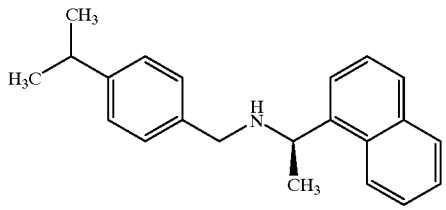

or a pharmaceutically acceptable salt thereof.

12. The compound of claim 7, wherein said compound is

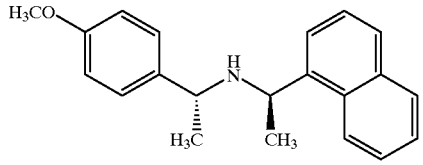

or a pharmaceutically acceptable salt thereof.

13. The compound of claim 7, wherein said compound is

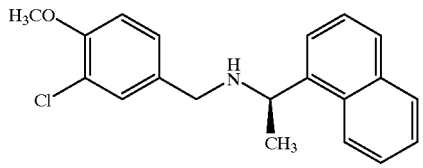

or a pharmaceutically acceptable salt thereof.

14. The compound of claim 7, wherein said compound is

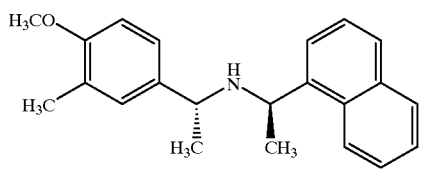

or a pharmaceutically acceptable salt thereof.

15. A pharmaceutical composition comprising a pharmaceutically acceptable carrier and a compound having the formula:

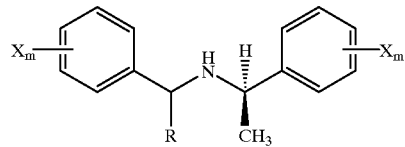

wherein each X independently is selected from the group consisting of $CH_3$, $CH_3O$, $CH_3CH_2O$, methylene dioxy made up of two X, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, an aliphatic ring, a fused aliphatic ring, an attached aromatic ring, and a fused aromatic ring made up of two X together; provided that a fused phenyl made up of two of X together is present to form an optionally substituted naphthyl;

R is selected from the group consisting of hydrogen, methyl, ethyl, propyl, isopropyl, butyl, allyl, isobutyl, t-butyl, cyclopentyl, cyclohexyl, cycloheptyl, cyclooctyl, indenyl, indanyl, dihydroindolyl, thiodihydroindolyl, and 2-, 3-, or 4-piperid(in)yl; and each m is independently between 0 and 5 inclusive; or a pharmaceutically acceptable salt thereof.

16. The composition of claim 15 wherein each X independently is selected from the group consisting of $CH_3$, $CH_3O$, $CH_3CH_2O$, methylene dioxy made up of two X, Br, Cl, F, $CF_3$, $CHF_2$, $CH_2F$ $CF_3O$, $CH_3S$, OH, $CH_2OH$, $CONH_2$, CN, $NO_2$, $CH_3CH_2$, propyl, isopropyl, butyl, isobutyl, t-butyl, acetoxy, an aliphatic ring, an attached aromatic ring, and a fused aromatic ring made up of two X; and R is selected from the group consisting of H, $CH_3$, ethyl, and isopropyl.

17. The composition of claim 16, wherein each X is independently selected from the group consisting of isopropyl, $CH_3O$, $CH_3S$, $CF_3O$, an aliphatic ring, an attached aromatic ring, and a fused aromatic ring made up of two X together; and each m is 2–5.

18. The composition of claim 17, wherein R is either H or $CH_3$.

19. The composition of claim 15, wherein said compound is either

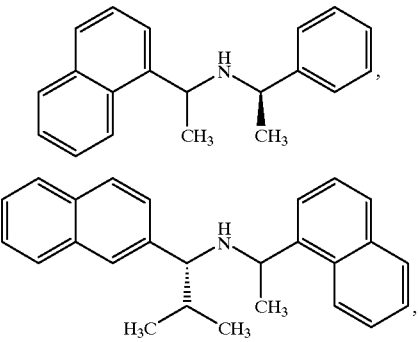

-continued
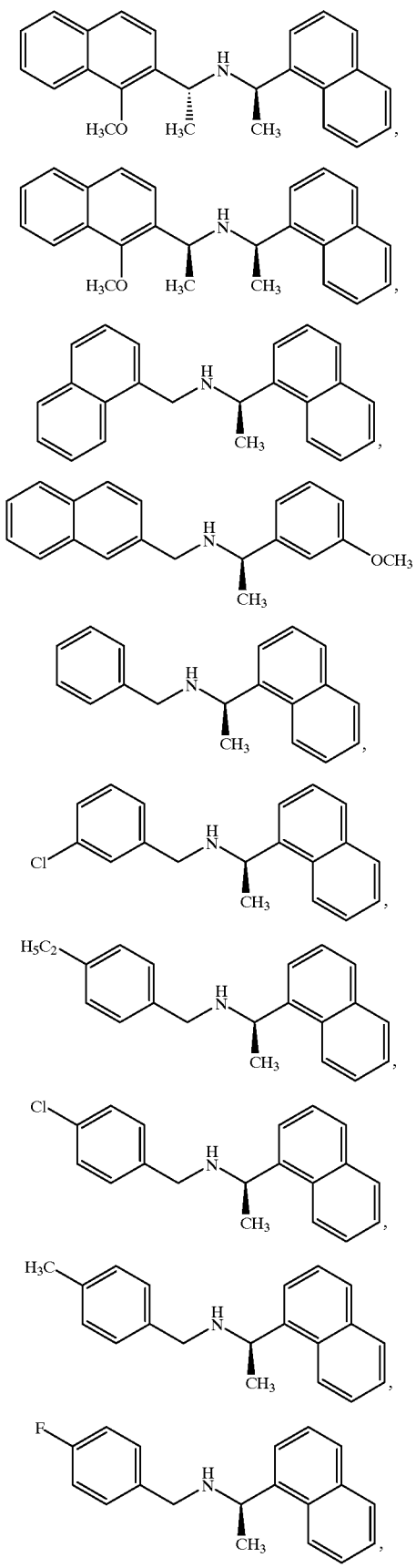
-continued
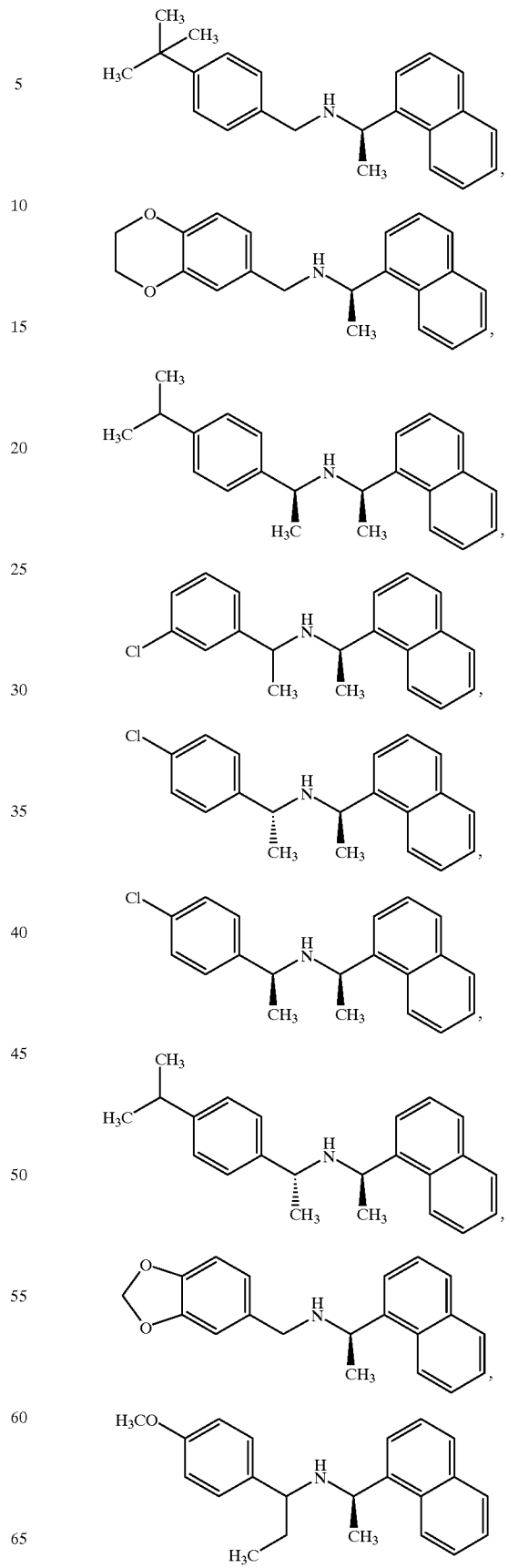

-continued

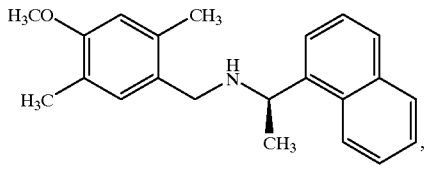

or a pharmaceutically acceptable salt thereof.

20. The composition of claim 15, wherein said compound is

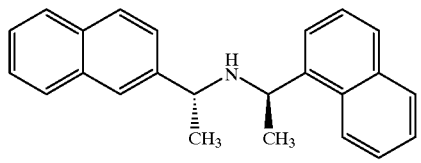

or a pharmaceutically acceptable salt thereof.

21. The composition of claim 15, wherein said compound is

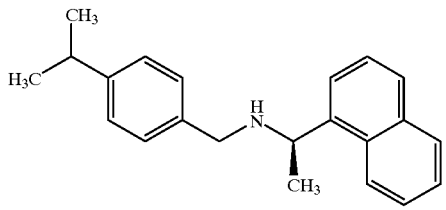

or a pharmaceutically acceptable salt thereof.

22. The composition of claim 15, wherein said compound is

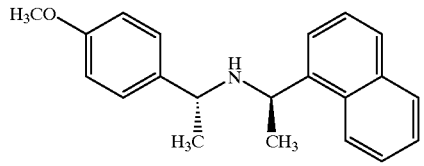

or a pharmaceutically acceptable salt thereof.

23. The composition of claim 15, wherein said compound is

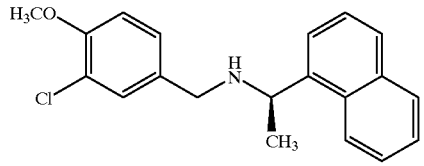

or a pharmaceutically acceptable salt thereof.

24. The composition of claim 15, wherein said compound is

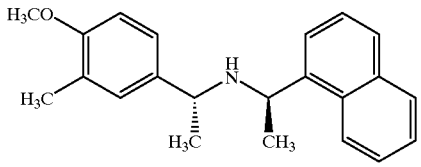

or a pharmaceutically acceptable salt thereof.

25. A method for treating a patient having a disease or disorder characterized by abnormal calcium homeostasis comprising the step of administering to said patient a therapeutically effective amount of a compound having the formula:

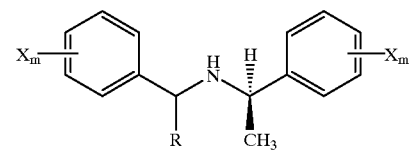

wherein each X independently is selected from the group consisting of $CH_3$, $CH_3O$, $CH_3CH_2O$, methylene dioxy made up of two X, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, an aliphatic ring, an attached aromatic ring, and a fused aromatic ring made up of two X together; provided that a fused phenyl made up of two of X together is present to form an optionally substituted naphthyl;

R is selected from the group consisting of hydrogen, methyl, ethyl, propyl, isopropyl, butyl, allyl, isobutyl, t-butyl, cyclopentyl, cyclohexyl, cycloheptyl, cyclooctyl, indenyl, indanyl, dihydroindolyl, thiodihydroindolyl, and 2-, 3-, or 4-piperid(in)yl; and each m is independently between 0 and 5 inclusive; or a pharmaceutically acceptable salt thereof.

26. The method of claim 25, wherein each X independently is selected from the group consisting of $CH_3$, $CH_3O$, $CH_3CH_2O$, methylene dioxy made up of two X, Br, Cl, F, $CF_3$, $CHF_2$, $CH_2F$, $CF_3O$, $CH_3S$, OH, $CH_2OH$, $CONH_2$, CN, $NO_2$, $CH_3CH_2$, propyl, isopropyl, butyl, isobutyl, t-butyl, acetoxy, an aliphatic ring, an attached aromatic ring, and a fused aromatic ring made up of two X; R is selected from the group consisting of H, $CH_3$, ethyl, and isopropyl.

27. The method of claim 26, wherein each X is independently selected from the group consisting of isopropyl, $CH_3O$, $CH_3S$, $CF_3O$, an aliphatic ring, an attached aromatic ring, and a fused aromatic ring made up of two X together.

28. The method of claim 27, wherein R is either H or $CH_3$, and each m is 2–5.

29. The method of claim 25, wherein said compound is either

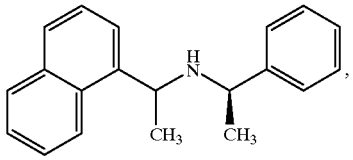

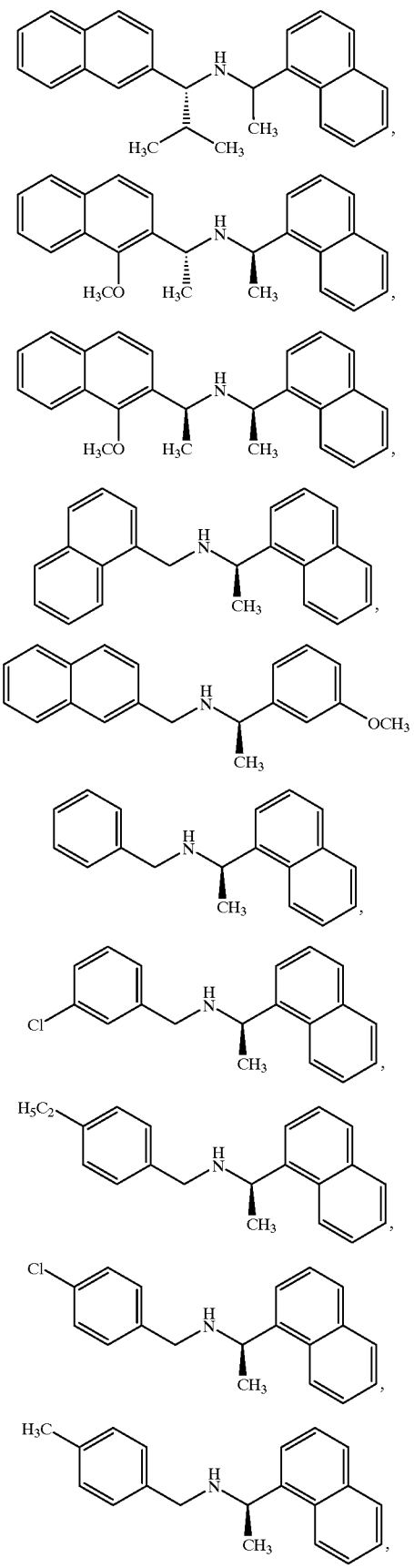
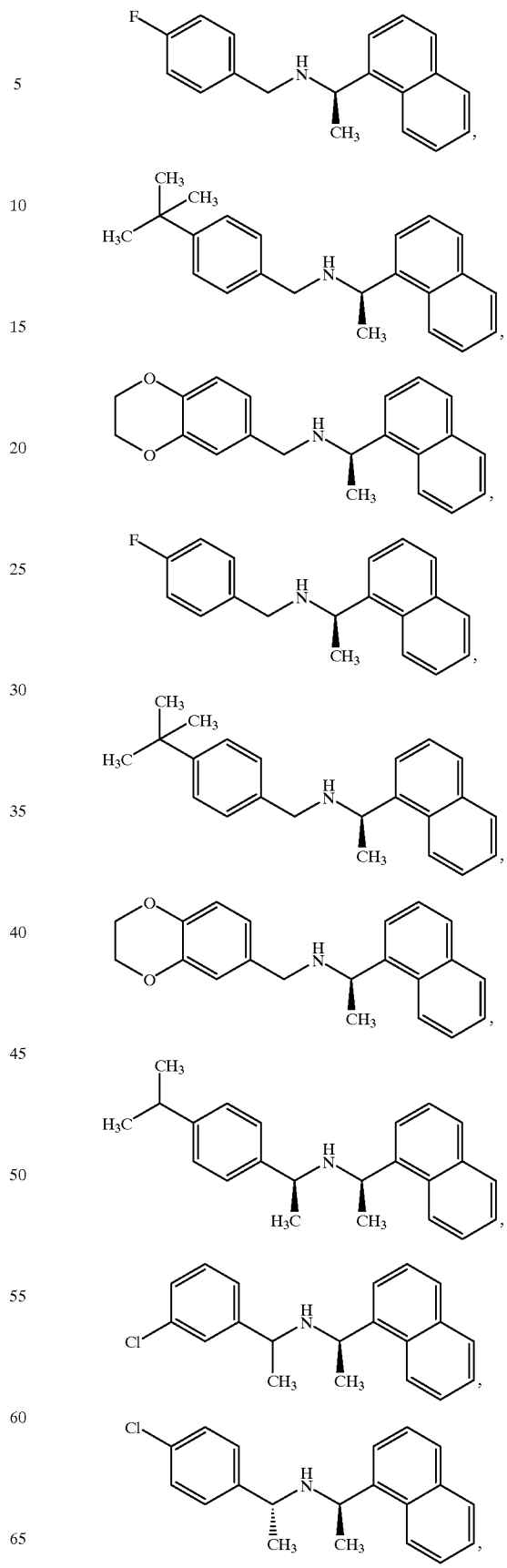

-continued

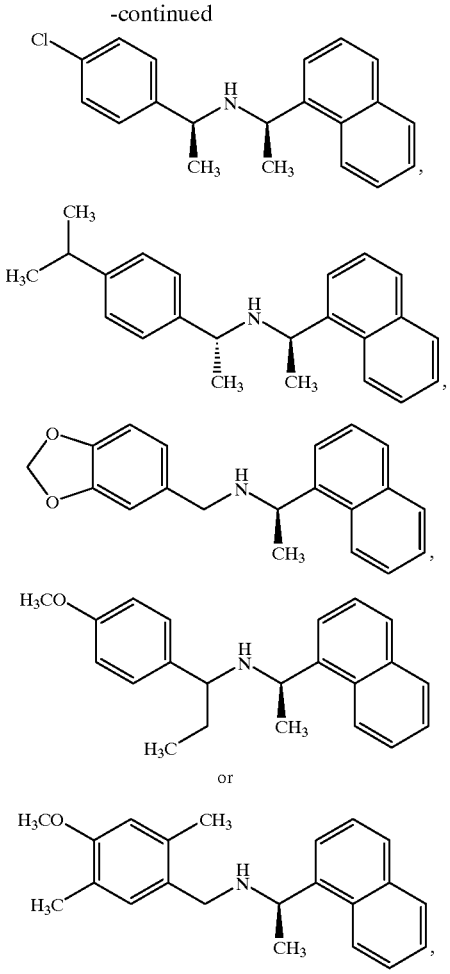

or a pharmaceutically acceptable salt thereof.

30. The method of claim 25, wherein said compound is

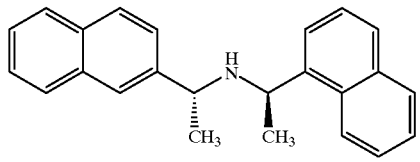

or a pharmaceutically acceptable salt thereof.

31. The method of claim 25, wherein said compound is

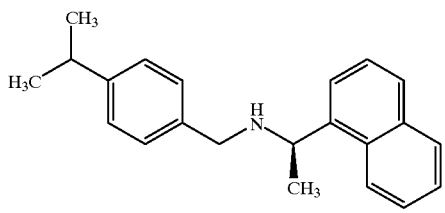

or a pharmaceutically acceptable salt thereof.

32. The method of claim 25, wherein said compound is

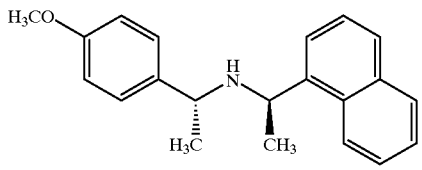

or a pharmaceutically acceptable salt thereof.

33. The method of claim 25, wherein said compound is

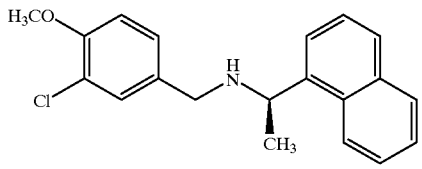

or a pharmaceutically acceptable salt thereof.

34. The method of claim 25, wherein said compound is

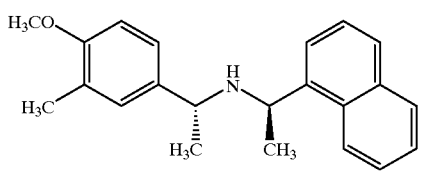

or a pharmaceutically acceptable salt thereof.

35. The method of any of one of claims 25–34, wherein said method is used to treat primary or secondary hyperparathyroidism.

36. The method of any of one of claims 25–34, wherein said method is used to treat Paget's disease.

37. The method of any of one of claims 25–34, wherein said method is used to decrease parathyroid hormone level in said patient to achieve a beneficial effect.

38. The method of any of one of claims 25–34, wherein said method is used to treat hypertension.

39. The method of any of one of claims 25–34, wherein said method is used to treat osteoporosis.

40. A method of treating a patient having a disease or disorder characterized by abnormal calcium homeostasis comprising the step of administering to said patient an effective amount of the compound of claim 15.

41. A method according to claim 40 wherein said disease or disorder is selected from the group consisting of hyperparathyroidism, osteoporosis, gut motility disorders, diarrhea, GI ulcer diseases, GI absorption diseases, sarcoidosis, and autoimmune diseases.

42. A method according to claim 40 wherein said disease or disorder is selected from the group consisting of seizures, stroke, head trauma, spinal cord injury, hypoxia-induced nerve cell damage caused by cardiac arrest or neonatal distress, hypertension, and epilepsy.

43. A method according to claim 40 wherein said disease or disorder is selected from the group consisting of syndrome of inappropriate ADH secretion, cirrhosis, nephrosis, and heart failure.

44. A method according to claim 40 wherein said disease or disorder is selected from the group consisting of Alzheimer's disease, Huntington's disease, Parkinson's disease, dementia, muscle tension, depression, anxiety, panic disorder, obsessive-compulsive disorder, post-traumatic stress disorder, schizophrenia, neuroleptic malignant syndrome, and Tourette's syndrome.

* * * * *